United States Patent
Clark et al.

(10) Patent No.: US 10,160,742 B2
(45) Date of Patent: Dec. 25, 2018

(54) PYRIDYL REVERSE SULFONAMIDES FOR HBV TREATMENT

(71) Applicant: Novira Therapeutics, Inc., Doylestown, PA (US)

(72) Inventors: Ryan C. Clark, San Diego, CA (US); Yen Truong, San Diego, CA (US); Nicholas Stock, Encinitas, CA (US); Jason Jacintho, San Diego, CA (US)

(73) Assignee: NOVIRA THERAPEUTICS, INC., Doylestown, PA (US)

( * ) Notice: Subject to any disclaimer, the term of this patent is extended or adjusted under 35 U.S.C. 154(b) by 0 days.

(21) Appl. No.: 15/676,236

(22) Filed: Aug. 14, 2017

(65) Prior Publication Data
US 2018/0051000 A1    Feb. 22, 2018

Related U.S. Application Data

(62) Division of application No. 14/957,008, filed on Dec. 2, 2015, now Pat. No. 9,765,050.

(60) Provisional application No. 62/097,854, filed on Dec. 30, 2014.

(51) Int. Cl.
C07D 333/26 (2006.01)
A61K 45/06 (2006.01)
C07D 213/81 (2006.01)
C07D 231/18 (2006.01)

(52) U.S. Cl.
CPC ............ *C07D 333/26* (2013.01); *A61K 45/06* (2013.01); *C07D 213/81* (2013.01); *C07D 231/18* (2013.01)

(58) Field of Classification Search
CPC .. C07D 333/26; C07D 213/81; C07D 231/18; A61K 45/06
USPC ........................................................ 546/304
See application file for complete search history.

(56) References Cited

U.S. PATENT DOCUMENTS

| 4,595,780 A * | 6/1986 | Ogata .................. C07D 213/75 564/79 |
| 6,699,891 B1 | 3/2004 | Kawanishi et al. |
| 9,061,008 B2 | 6/2015 | Hartman et al. |
| 9,066,932 B2 | 6/2015 | Hartman et al. |
| 2006/0063779 A1 | 3/2006 | Gunzner et al. |
| 2011/0123489 A1 | 5/2011 | Taygerly et al. |
| 2014/0178337 A1 | 6/2014 | Hartman et al. |
| 2014/0179665 A1 | 6/2014 | Hartman et al. |
| 2015/0152073 A1 | 6/2015 | Hartman et al. |
| 2015/0259324 A1 | 9/2015 | Hartman et al. |
| 2016/0052870 A1 | 2/2016 | Schiltz et al. |
| 2016/0151375 A1 | 6/2016 | Chen et al. |
| 2016/0185748 A1 | 6/2016 | Clark et al. |

FOREIGN PATENT DOCUMENTS

| EP | 0 148 725 A1 | 7/1985 |
| WO | 1999/032433 A1 | 7/1999 |
| WO | 2001/087294 A1 | 11/2001 |
| WO | 2011/018170 A2 | 2/2011 |
| WO | 2012/106534 A2 | 8/2012 |
| WO | WO2013006394 * | 1/2013 |
| WO | 2013/096744 A1 | 6/2013 |
| WO | 2014/033170 A1 | 3/2014 |
| WO | 2014/106019 A2 | 7/2014 |
| WO | 2016/016370 A1 | 2/2016 |
| WO | 2016/089990 A1 | 6/2016 |

OTHER PUBLICATIONS

Chemical Abstracts STN Registry Database record for RN 1280388-44-4, Entered on Apr. 15, 2011. (Year: 2011).*
Chemical Abstracts STN Registry Database record for RN 1097573-34-6, Entered on Jan. 29, 2009. (Year: 2009).*
Campagna; J. Virol. 2013, 87, 6931-6942. (Year: 2013).*
Gane (Nov. 2014) "Phase la Safety and Pharmacokinetics of NVR 3-778, a Potential First-In-Class HBV Core Inhibitor," In; The Annual Meeting of the American Association for the Study of Liver Diseases, LB-19.
Ogata et al. (1986) "Synthesis and Antiviral Activity of Sulfonamidobenzophenone Oximes and Sulfonamidobenzamides," J. Med. Chem. 29:417-423.
Tang (May 2014) "Management of chronic hepatitis B infection: Current treatment guidelines, challenges, and new developments," World J. Gastroenterol. 20:6262-6278.
International Search Report corresponding to International Patent Application No. PCT/US2015/063417, dated Mar. 2, 2016.
Written Opinion corresponding to International Patent Application No. PCT/US2015/063417, dated Feb. 11, 2016.

* cited by examiner

*Primary Examiner* — Daniel R Carcanague
(74) *Attorney, Agent, or Firm* — Brian C. Trinque; Benjamin A. Vaughan; Lathrop Gage LLP

(57) ABSTRACT

The present invention includes a method of inhibiting, suppressing or preventing HBV infection in an individual in need thereof, comprising administering to the individual a therapeutically effective amount of at least one compound of the invention.

8 Claims, 3 Drawing Sheets

PYRIDYL REVERSE SULFONAMIDES FOR HBV TREATMENT

RELATED APPLICATIONS

This application is a Divisional of U.S. application Ser. No. 14/957,008 filed Dec. 2, 2015, which claims priority to U.S. Provisional Patent Application No. 62/097,854, filed Dec. 30, 2014. The contents of these applications are herein incorporated by reference in their entireties.

BACKGROUND OF THE INVENTION

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, or enhanced seroconversion rates.

SUMMARY OF THE INVENTION

Provided herein are compounds useful for the treatment of HBV infection in a subject in need thereof.

In one aspect, provided herein are compounds of Formula I:

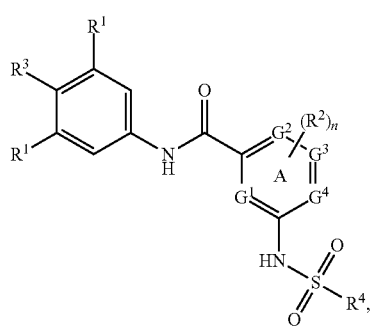

I or a pharmaceutically acceptable salt thereof.

In another aspect, provided herein are compounds of Formula II:

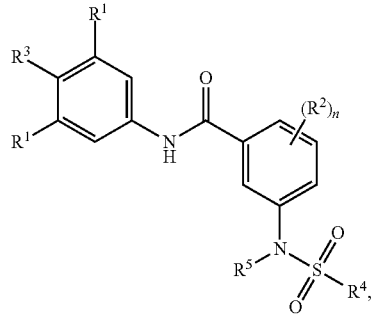

II or a pharmaceutically acceptable salt thereof.

In another aspect, provided herein are compounds of Formula III:

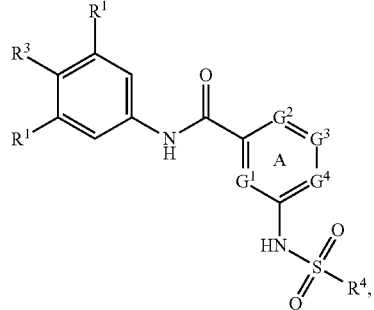

III or a pharmaceutically acceptable salt thereof.

Also provided herein are compositions comprising a compound provided herein (also referred to herein as "a compound of the invention"), or a salt, solvate, or N-oxide thereof. In one embodiment, the composition is pharmaceutical and further comprises at least one pharmaceutically acceptable carrier.

In another aspect, provided herein is a method of treating an HBV infection in an individual in need thereof, comprising administering to the individual a therapeutically effective amount of a compound of the invention.

In still another aspect, provided herein is a method of reducing the viral load associated with an HBV infection in an individual in need thereof, comprising administering to the individual a therapeutically effective amount of a compound of the invention.

In yet another aspect, provided herein is a method of reducing reoccurrence of an HBV infection in an individual in need thereof, comprising administering to the individual a therapeutically effective amount of a compound of the invention.

Also provided herein are methods of reducing an adverse physiological impact of an HBV infection in an individual in need thereof, comprising administering to the individual a therapeutically effective amount of a compound of the invention.

In another aspect, provided herein is a method of inducing remission of hepatic injury from an HBV infection in an individual in need thereof, comprising administering to the individual a therapeutically effective amount of a compound of the invention.

In yet another aspect, provided herein is a method of reducing the physiological impact of long-term antiviral therapy for HBV infection in an individual in need thereof, comprising administering to the individual a therapeutically effective amount of a compound of the invention.

In still another aspect, provided herein is a method of prophylactically treating an HBV infection in an individual in need thereof, wherein the individual is afflicted with a latent HBV infection, comprising administering to the individual a therapeutically effective amount of a compound of the invention.

Any of the above methods may further comprise administration to the individual at least one additional therapeutic agent. In an embodiment, the additional therapeutic agent may be selected from, but not limited to, the group consisting of a HBV polymerase inhibitor, immunomodulatory agents, pegylated interferon, viral entry inhibitor, viral maturation inhibitor, capsid assembly modulator, reverse transcriptase inhibitor, a cyclophilin/TNF inhibitor, a TLR-agonist, an HBV vaccine, and agents of distinct or unknown mechanism, and a combination thereof.

In another embodiment, the at least one additional therapeutic agent is selected from the group consisting of an HBV vaccine, HBV polymerase inhibitor, interferon, pegylated interferon, viral entry inhibitor, viral maturation inhibitor, capsid assembly modulator, reverse transcriptase inhibitor, a TLR-agonist, and agents of distinct or unknown mechanism, and a combination thereof.

In still another embodiment, the additional therapeutic agent is selected from the group consisting of a HBV polymerase inhibitor, interferon, viral entry inhibitor, viral maturation inhibitor, capsid assembly modulator, reverse transcriptase inhibitor, a TLR-agonist, and agents of distinct or unknown mechanism, and a combination thereof.

In another embodiment, the pegylated interferon is pegylated interferon alpha (IFN-$\alpha$), pegylated interferon lambda (IFN-$\lambda$), or pegylated interferon gamma (IFN-$\gamma$).

In yet another embodiment, the reverse transcriptase inhibitor is at least one of Zidovudine, Didanosine, Zalcitabine, ddA (2',3'-dideoxyadenosine), Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

In still another embodiment, the compound and the at least one additional therapeutic agent are co-formulated.

In yet another embodiment, the compound and the at least one additional therapeutic agent are co-administered.

DETAILED DESCRIPTION OF THE INVENTION

Figure 1:
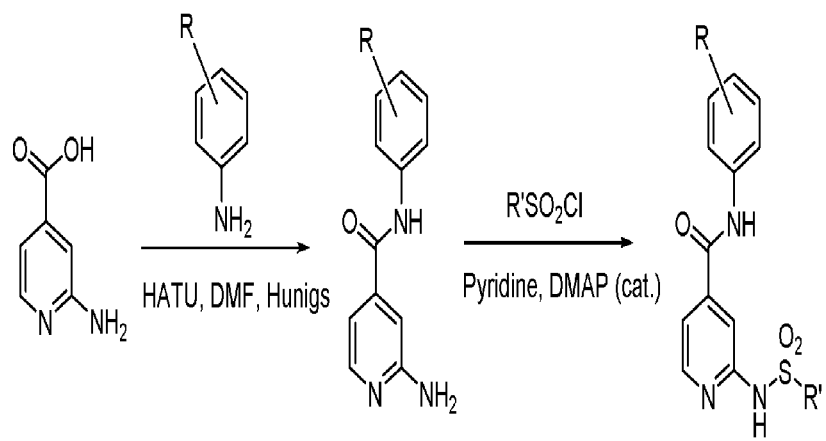
FIG. 1 shows a general scheme used to prepare selected compounds of the invention.

Provided herein are compounds that are useful in the treatment and prevention of HBV infection in man. In a non-limiting aspect, these compounds modulate or disrupt HBV viral replication to afford defective virion with greatly reduced virulence. The compounds of the invention have potent antiviral activity, exhibit favorable metabolic, tissue distribution, safety and pharmaceutical profiles, and are suitable for use in man.

HBV, a causative agent of acute/chronic hepatitis, consists of a partially double-stranded 3.2 kb circular DNA from which four proteins are synthesized: the core, polymerase, surface antigen, and X-gene product.

Four promoters with unique functions have been identified in the HBV genome. The pregenomic/core promoter directs the synthesis of 3.6 kb mRNA which contains all the genetic information encoded by the virus. This RNA serves as a replication intermediate and as a template for the synthesis of core and polymerase. The S promoter and the pre-S promoter direct the synthesis of 2.1 and 2.4 kb RNAs utilized for the generation of pre-S1, pre-S2, and S proteins. X promoter directs the transcription of 0.9 kb RNA specific for the synthesis of X gene product. Liver-specific and differentiation state-specific utilization of these promoters are regulated by the two enhancer elements, i.e., enhancer I (ENI) and enhancer II (ENII). These enhancers along with HNF-1 (hepatocyte nuclear factor-1) binding element are largely responsible for the restricted tropism of HBV to hepatocytes.

The mechanism of HBV replication differs from that of other DNA viruses in that, like retroviruses, the reverse transcription step is involved. Upon infection of the hepatocytes, a partially double-stranded genome is converted to a complete double-stranded circular, supercoiled DNA. Employing this as a template, 3.6 kb RNA, which is called the pregenome, is transcribed. The pregenome is packaged into a nucleocapsid and is reverse-transcribed using polymerase as an initiation primer to generate the minus-strand, single-stranded DNA. The polymerization of the second strand follows until approximately half of the genome is synthesized, resulting in the generation of partially double-stranded circular genome, which is coated and secreted by the infected cells.

In one aspect, the compounds of the invention are useful in HBV treatment by disrupting, accelerating, reducing, delaying or inhibiting normal viral replication, thereby inducing aberrant viral replication and leading to antiviral effects such as disruption of virion assembly or disassembly, virion maturation, or virus egress.

In one embodiment, the compounds of the invention disrupt viral replication when the virion is immature. In another embodiment, the compounds of the invention disrupt viral replication when the virion is mature. In yet another embodiment, the compounds of the invention disrupt viral replication during viral infectivity. In yet another embodiment, the disruption of viral replication attenuates HBV viral infectivity or reduces viral load. In yet another embodiment, disruption, inhibition, delay or reduction of viral replication eradicates the virus from the host organism. In yet another embodiment, eradication of the HBV from a host advantageously obviates the need for chronic long-term therapy or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity, stability, function, and viral replication properties of HBV cccDNA. In yet another embodiment, the compounds of the invention can be used in methods of diminishing or preventing the formation of HBV cccDNA.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "capsid assembly modulator" refers to a compound that disrupts and/or accelerates and/or inhibits and/or hinders and/or delays and or reduces and/or modifies normal capsid assembly (e.g., during maturation) and/or normal capsid disassembly (e.g., during infectivity) and/or perturbs capsid stability, thereby inducing aberrant capsid morphology and function. In one embodiment, a capsid assembly modulator accelerates capsid assembly and/or disassembly, thereby inducing aberrant capsid morphology. In another embodiment, a capsid assembly modulator interacts (e.g. binds at an active site, binds at an allosteric site, modifies and/or hinders folding and the like) with the major capsid assembly protein (CA), thereby disrupting capsid assembly and/or disassembly. In yet another embodiment, a capsid assembly modulator causes a perturbation in structure and/or function of CA (e.g., ability of CA to assemble, disassemble, bind to a substrate, fold into a suitable conformation, or the like), which attenuates viral infectivity and/or is lethal to the virus.

As used herein, the term "literature-described capsid assembly modulator" refers a capsid assembly modulator that is not a compound of the present invention.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has HBV infection, a symptom of HBV infection or the potential to develop HBV infection, with the purpose to heal, alleviate, relieve, alter, remedy, ameliorate, improve or affect HBV infection, the symptoms of HBV infection or the potential to develop HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The term "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$. Preferred heteroalkyl groups have 1-10 carbons.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

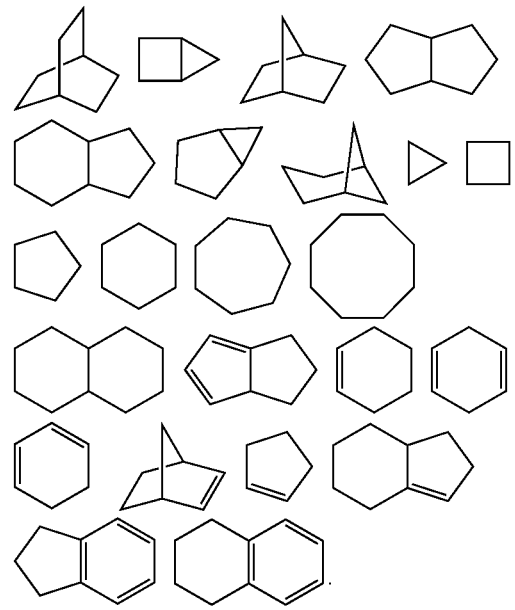

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

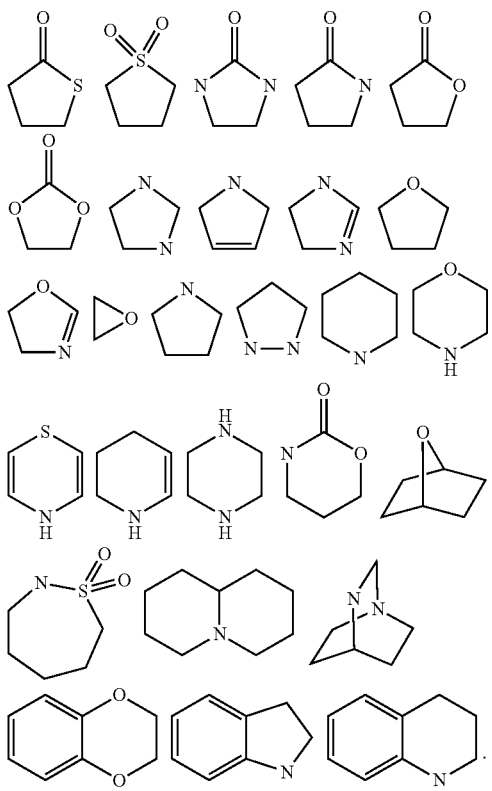

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "heteroaryl" or "heteroaromatic" refers to a heterocycle having aromatic character. A polycyclic heteroaryl may include one or more rings that are partially saturated. Examples include the following moieties:

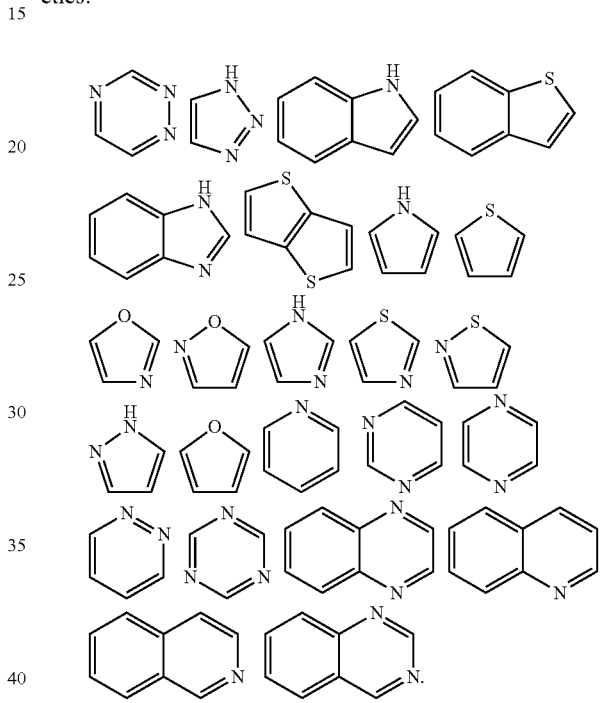

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

Compounds of the Invention

The present invention relates to the discovery of compounds that are useful in the treatment and prevention of HBV infection in man. In one aspect, the compounds of the invention are useful in HBV treatment by disrupting, accelerating, reducing, delaying or inhibiting normal HBV viral replication, thereby inducing aberrant viral replication and leading to antiviral effects such as disruption of virion assembly or disassembly, or virion maturation, or virus egress.

The viral replication disruptors disclosed herein may be used as monotherapy or in novel cross-class combination regimens for treating HBV infection in man. Combination therapy with drugs exhibiting different mechanism of action (MOA) that act at different steps in the virus life cycle may deliver greater efficacy due to additive or synergistic antiviral effects. Clinically evaluated HIV treatment regimens have shown that combination therapy improves the efficacy of viral load reduction, and dramatically reduces emergence of antiviral resistance. Combination therapy for the treatment of Hepatitis C (HCV) virus infection has also resulted in significant improvement in sustained antiviral response and eradication rates. Thus, use of the HBV viral replication inhibitors of the present invention in combination with, for example, NA drugs, is likely to deliver a more profound antiviral effect and greater disease eradication rates than current standards of care.

In one aspect, drug resistance poses a major threat to current therapies for chronic HBV infection, and cross-class combination therapy is a proven strategy for delaying emergence of drug resistance strains. The viral replication disruptors of the present invention can, when administered alone or in combination with other HBV therapy, offer enhanced drug resistant profiles and improved management of chronic HBV.

The compounds useful within the invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of Formula I:

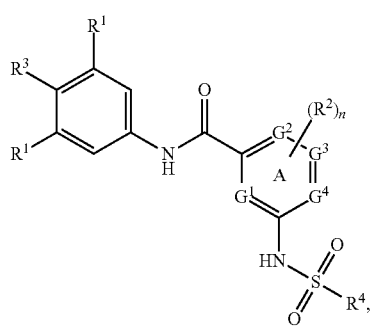

or a pharmaceutically acceptable salt thereof;
wherein three of $G^{1-4}$ are independently selected from C and CH, and one of $G^{1-4}$ is N;

each $R^1$ is independently selected from H, halo, and CN;

each $R^2$ is, independently for each occurrence, selected from halo, $C_{1-6}$-alkyl, $C_{1-6}$-alkoxy, halo-($C_{1-6}$-alkyl), di-halo-($C_{1-6}$-alkyl), and tri-halo-($C_{1-6}$-alkyl);

$R^3$ is halo;

$R^4$ is selected from $C_{1-6}$-alkyl, $C_{1-6}$-heteroalkyl, $C_{3-7}$-cycloalkyl, ($C_{1-6}$-alkyl)-($C_{3-7}$-cycloalkyl), aryl, ($C_{1-6}$-alkyl)-aryl, $C_{3-7}$-heterocycloalkyl, ($C_{1-6}$-alkyl)-($C_{3-7}$-heterocycloalkyl), heteroaryl, ($C_{1-6}$-alkyl)-C(O)O—($C_{1-6}$-alkyl), and ($C_{1-6}$-alkyl)-heteroaryl, all of which may be optionally substituted with halo, OH, CN, $C_{1-6}$-alkyl, O—($C_{1-6}$-alkyl), $CF_3$, benzyl, C(O)OH, ($C_{1-6}$-alkyl)-C(O)OH, or C(O)O—($C_{1-6}$-alkyl); and n is 0, 1, or 2.

In one embodiment, ring A is

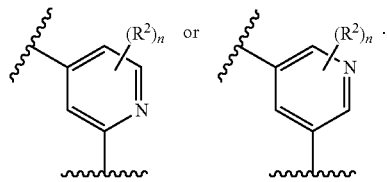

In another embodiment, ring A is

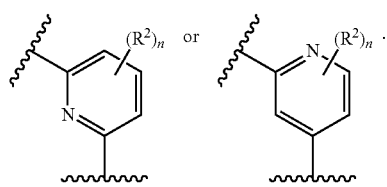

In still another embodiment, $R^4$ is selected from $C_{1-6}$-alkyl, $C_{3-7}$-cycloalkyl, ($C_{1-6}$-alkyl)-($C_{3-7}$-cycloalkyl), $C_{3-7}$-heterocycloalkyl, and ($C_{1-6}$-alkyl)-($C_{3-7}$-heterocycloalkyl), all of which may be optionally substituted with OH or $C_{1-6}$-alkyl.

In an embodiment, the compound of Formula I is a compound of Formula Ia:

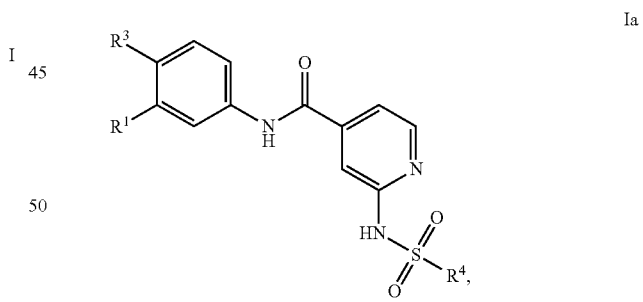

or a pharmaceutically acceptable salt thereof;
wherein
$R^1$ is selected from halo, and CN;
$R^3$ is halo; and
$R^4$ is selected from $C_{1-6}$-alkyl, $C_{1-6}$-heteroalkyl, $C_{3-7}$-cycloalkyl, ($C_{1-6}$-alkyl)-($C_{3-7}$-cycloalkyl), aryl, ($C_{1-6}$-alkyl)-aryl, $C_{3-7}$-heterocycloalkyl, ($C_{1-6}$-alkyl)-($C_{3-7}$-heterocycloalkyl), heteroaryl, ($C_{1-6}$-alkyl)-C(O)O—($C_{1-6}$-alkyl), and ($C_{1-6}$-alkyl)-heteroaryl, all of which may be optionally substituted with halo, OH, CN, $C_{1-6}$-alkyl, O—($C_{1-6}$-alkyl), $CF_3$, benzyl, C(O)OH, ($C_{1-6}$-alkyl)-C(O)OH, or C(O)O—($C_{1-6}$-alkyl).

In an embodiment of Formula Ia, $R^3$ is F.

In another embodiment, $R^4$ is selected from $C_{1-6}$-alkyl, $C_{3-7}$-cycloalkyl, ($C_{1-6}$-alkyl)-($C_{3-7}$-cycloalkyl), ($C_{1-6}$-alkyl)-aryl, $C_{3-7}$-heterocycloalkyl, and ($C_{1-6}$-alkyl)-($C_{3-7}$-heterocycloalkyl), all of which may be optionally substituted with OH or $C_{1-6}$-alkyl.

In yet another embodiment, $R^4$ is selected from $C_{1-6}$-alkyl, $C_{3-7}$-cycloalkyl, ($C_{1-6}$-alkyl)-($C_{3-7}$-cycloalkyl), and ($C_{1-6}$-alkyl)-aryl, all of which may be optionally substituted with $C_{1-6}$-alkyl.

In still another embodiment, $R^4$ is selected from $C_{1-6}$-alkyl, $C_{3-7}$-cycloalkyl, ($C_{1-6}$-alkyl)-($C_{3-7}$-cycloalkyl), and ($C_{1-6}$-alkyl)-aryl, wherein the $C_{3-7}$-cycloalkyl and ($C_{1-6}$-alkyl)-aryl are substituted with $C_{1-6}$-alkyl.

In another embodiment of Formula Ia, or a pharmaceutically acceptable salt thereof, $R^1$ is halo; $R^3$ is halo; and $R^4$ is selected from $C_{1-6}$-alkyl, $C_{1-6}$-heteroalkyl, $C_{3-7}$-cycloalkyl, ($C_{1-6}$-alkyl)-($C_{3-7}$-cyclo alkyl), ($C_{1-6}$-alkyl)-aryl, $C_{3-7}$-heterocycloalkyl, ($C_{1-6}$-alkyl)-($C_{3-7}$-heterocycloalkyl), heteroaryl, all of which may be substituted with OH or $C_{1-6}$-alkyl.

In another embodiment of Formula Ia, or a pharmaceutically acceptable salt thereof, $R^1$ is halo; $R^3$ is halo; and $R^4$ is selected from $C_{1-6}$-alkyl, $C_{3-7}$-cycloalkyl, ($C_{1-6}$-alkyl)-($C_{3-7}$-cycloalkyl), and ($C_{1-6}$-alkyl)-aryl, wherein the $C_{3-7}$-cycloalkyl and ($C_{1-6}$-alkyl)-aryl groups are optionally substituted with $C_{1-6}$-alkyl.

In another embodiment, $R^4$ is selected from $C_{2-6}$-alkyl, $C_{3-7}$-cycloalkyl, ($C_{1-6}$-alkyl)-($C_{3-7}$-cycloalkyl), and ($C_{1-6}$-alkyl)-aryl, wherein the $C_{3-7}$-cycloalkyl and ($C_{1-6}$-alkyl)-aryl groups are optionally substituted with $C_{1-6}$-alkyl.

In another embodiment, $R^4$ is selected from $C_{1-6}$-alkyl, $C_{3-7}$-cycloalkyl, ($C_{1-6}$-alkyl)-($C_{3-7}$-cycloalkyl), and ($C_{1-6}$-alkyl)-aryl, wherein the $C_{3-7}$-cycloalkyl and ($C_{1-6}$-alkyl)-aryl groups are substituted with $C_{1-6}$-alkyl.

In another embodiment, $R^4$ is selected from $C_{2-6}$-alkyl, $C_{3-7}$-cycloalkyl, ($C_{1-6}$-alkyl)-($C_{3-7}$-cycloalkyl), and ($C_{1-6}$-alkyl)-aryl, wherein the $C_{3-7}$-cycloalkyl and ($C_{1-6}$-alkyl)-aryl groups are substituted with $C_{1-6}$-alkyl.

In another embodiment of Formula Ia, or a pharmaceutically acceptable salt thereof, the compound is selected from the group consisting of:

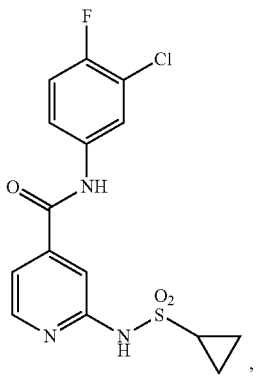

(124)

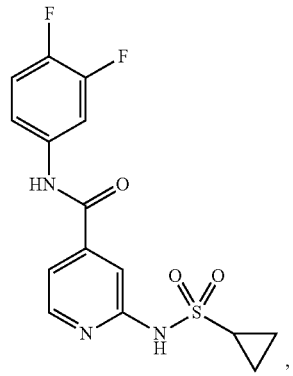

(128)

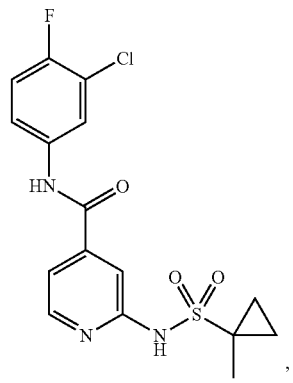

(130)

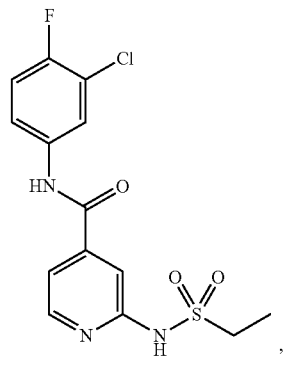

(131)

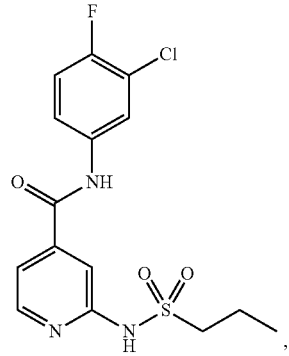

(133)

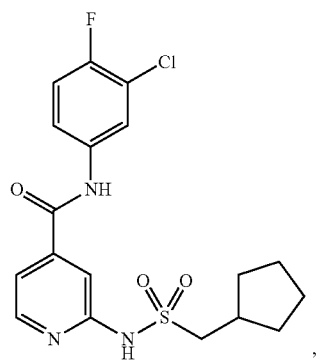
(150)
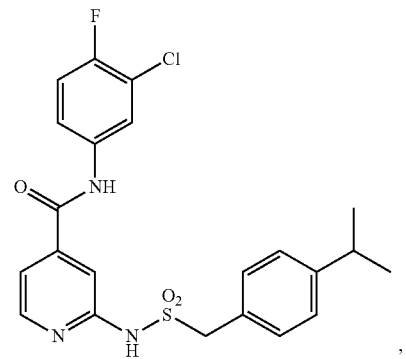
(188)
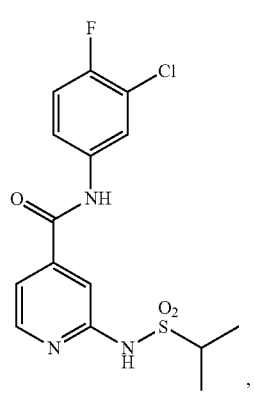
(163)
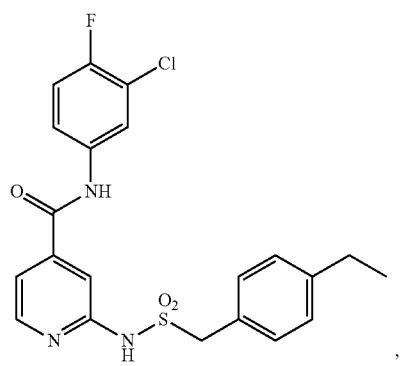
(189)
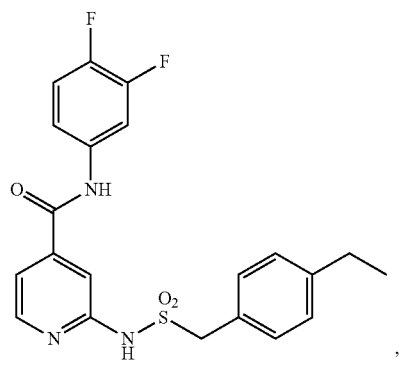
(180)
(194)
and
(181)
(195)
In another aspect, the compound of the invention is a compound of Formula II:

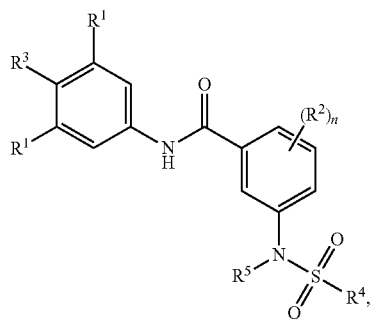

wherein each R¹ is independently selected from H, halo, CN, $C_{1-6}$-alkyl, $C_{1-6}$-alkoxy, halo-($C_{1-6}$-alkyl), di-halo-($C_{1-6}$-alkyl), tri-halo-($C_{1-6}$-alkyl), $OCF_3$, $N(H)S(O)_2$—($C_{1-6}$-alkyl), $S(O)_2$—($C_{1-6}$-alkyl), $C(H)(C_{1-6}$-alkyl)OH, $C(C_{1-6}$-alkyl)$_2$OH, C(O)—($C_{1-6}$-alkyl), and $C_{3-7}$-cycloalkyl;

R² is selected from halo, $C_{1-6}$-alkyl, $C_{1-6}$-alkoxy, halo-($C_{1-6}$-alkyl), di-halo-($C_{1-6}$-alkyl), tri-halo-($C_{1-6}$-alkyl), ($C_{1-6}$-alkyl)-OH, C(O)OH, $OCF_3$, and $C(O)O(C_{1-6}$-alkyl);

R³ is halo;

or R³ and one R¹, together with the atoms to which they are attached, form an isobenzofuranone;

R⁴ is selected from $C_{1-6}$-heteroalkyl, $C_{3-7}$-heterocycloalkyl, ($C_{1-6}$-alkyl)-($C_{3-7}$-heterocycloalkyl), heteroaryl, and ($C_{1-6}$-alkyl)-heteroaryl, all of which may be optionally independently substituted with one or two of OH and $C_{1-6}$-alkyl;

or R⁴ is $C_{3-7}$-heterocycloalkyl optionally substituted with OH, wherein the heteroatom is the group $S(O)_2$;

R⁵ is selected from H and $C_{1-6}$-alkyl; and n is 0 or 1.

In one embodiment of Formula II, each R¹ is independently selected from H, halo, CN, $C_{1-6}$-alkyl, $CH_2F$, $CHF_2$, $CF_3$, and $C_{3-7}$-cycloalkyl. In another embodiment, R² is selected from halo, $C_{1-6}$-alkyl, ($C_{1-6}$-alkyl)-OH, C(O)OH, and $OCF_3$. In still another embodiment, R⁴ is selected from $C_{1-6}$-heteroalkyl, $C_{3-7}$-heterocycloalkyl, and heteroaryl, all of which may be optionally independently substituted with one or two of $C_{1-6}$-alkyl.

In another embodiment, R³ is F.

In another embodiment of Formula II, each R¹ is independently selected from H, halo, and $C_{1-6}$-alkyl.

In yet another embodiment, one R¹ is H, and one R¹ is selected from H, halo, and $C_{1-6}$-alkyl.

In still another embodiment, R² is halo.

In another embodiment, R⁴ is selected from $C_{1-6}$-heteroalkyl, and heteroaryl, each of which may be optionally independently substituted with one or two of $C_{1-6}$-alkyl.

In yet another embodiment, n is 1.

In another embodiment of Formula II, or a pharmaceutically acceptable salt thereof, each R¹ is independently selected from H, halo, and $C_{1-6}$-alkyl; R² is halo; R³ is halo; R⁴ is $C_{1-6}$-heteroalkyl or heteroaryl, each of which may be independently substituted with one or two of $C_{1-6}$-alkyl; R⁵ is H; and n is 0 or 1.

In another embodiment of Formula II, or a pharmaceutically acceptable salt thereof, the compound is selected from the group consisting of:

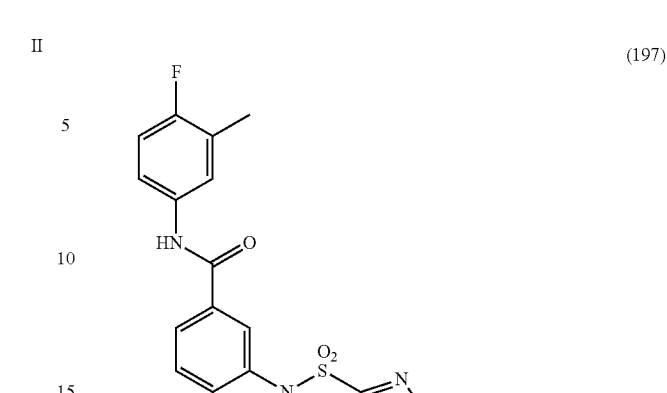

-continued (201)

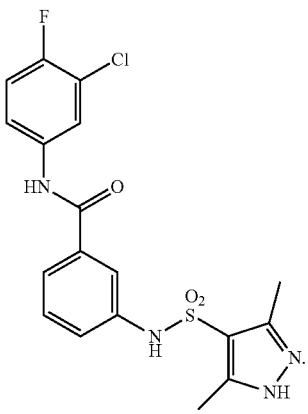

In still another aspect, the compound of the invention is a compound of Formula III:

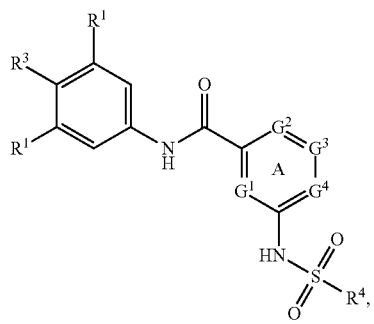

III wherein
ring A is heteroaryl;
two of $G^{1-4}$ are N and two of $G^{1-4}$ are CH;
each $R^1$ is independently selected from H and halo;
$R^3$ is halo; and
$R^4$ is $C_{3-7}$-cycloalkyl.
In one embodiment, ring A is

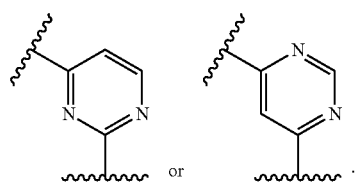 [SMILES: *c1ccnc(*)n1 ; "or" ; *c1cc(*)ncn1 ; "."]

or

It will be appreciated that the description of the present invention herein should be construed in congruity with the laws and principals of chemical bonding. In some instances it may be necessary to remove a hydrogen atom in order to accommodate a substituent at any given location.

Preferred embodiments of Formula I, Formula Ia, Formula II, and Formula III, including pharmaceutically acceptable salts thereof, are shown below in Table 1 and are also considered to be "compounds of the invention." Some compounds of Table 1 do not include hydrogens on hydroxyl groups; it is understood that "—O" indicates a hydroxyl substituent at these positions.

TABLE 1

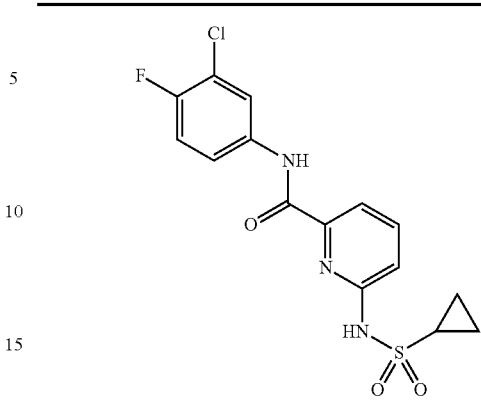

1

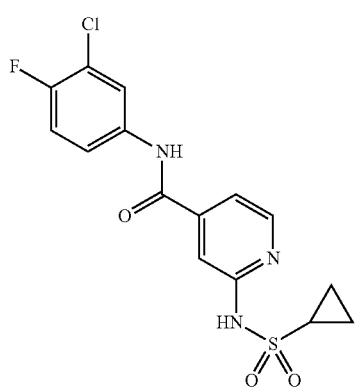 [SMILES: O=C(Nc1ccc(F)c(Cl)c1)c1ccnc(NS(=O)(=O)C2CC2)c1]

2

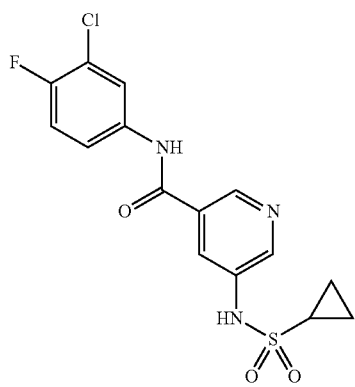 [SMILES: O=C(Nc1ccc(F)c(Cl)c1)c1cncc(NS(=O)(=O)C2CC2)c1]

3

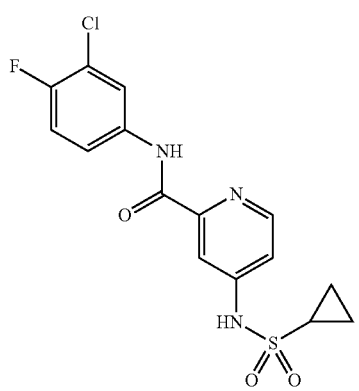 [SMILES: O=C(Nc1ccc(F)c(Cl)c1)c1cc(NS(=O)(=O)C2CC2)ccn1]

4

TABLE 1-continued
| | |
|---|---|
| 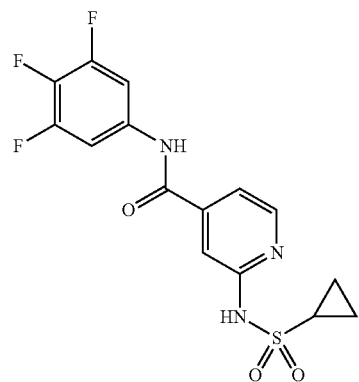 [SMILES: O=C(Nc1cc(F)c(F)c(F)c1)c1ccnc(NS(=O)(=O)C2CC2)c1] 5 | 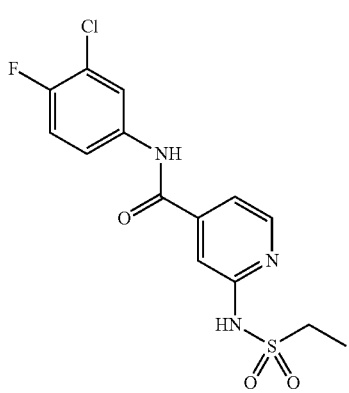 9 |
| 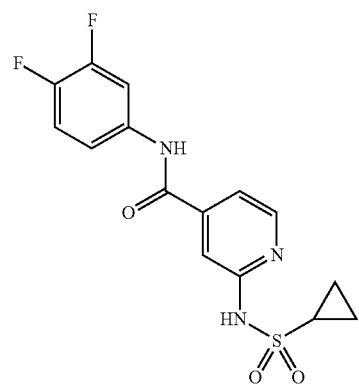 [SMILES: O=C(Nc1ccc(F)c(F)c1)c1ccnc(NS(=O)(=O)C2CC2)c1] 6 | 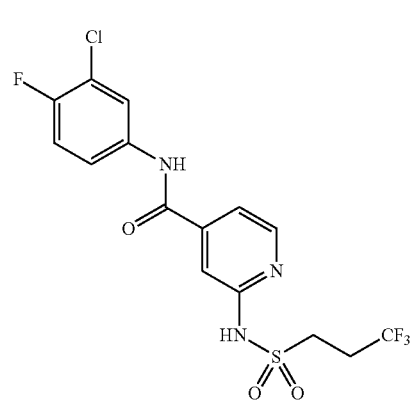 10 |
| 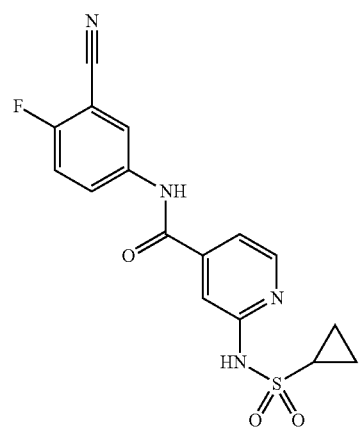 [SMILES: N#Cc1cc(NC(=O)c2ccnc(NS(=O)(=O)C3CC3)c2)ccc1F] 7 | 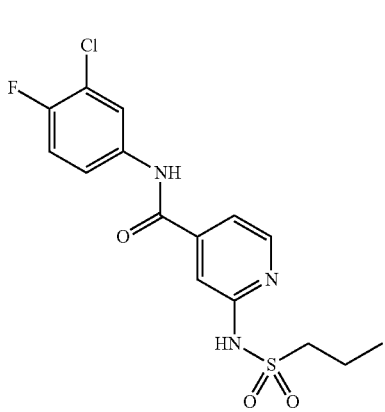 11 |
| 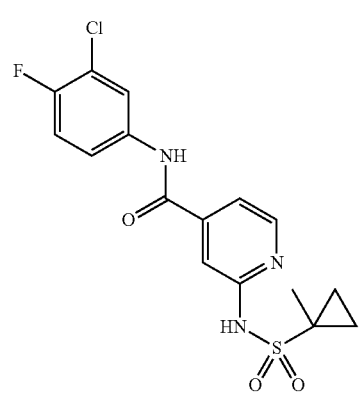 [SMILES: CC1(S(=O)(=O)Nc2cc(C(=O)Nc3ccc(F)c(Cl)c3)ccn2)CC1] 8 | 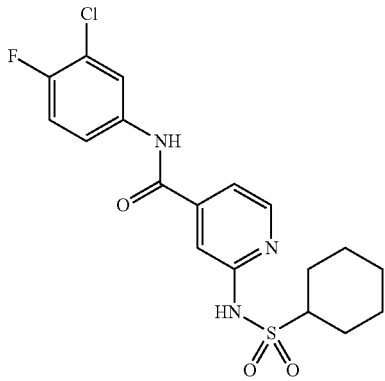 [SMILES: O=C(Nc1ccc(F)c(Cl)c1)c1ccnc(NS(=O)(=O)C2CCCCC2)c1] 12 |

TABLE 1-continued
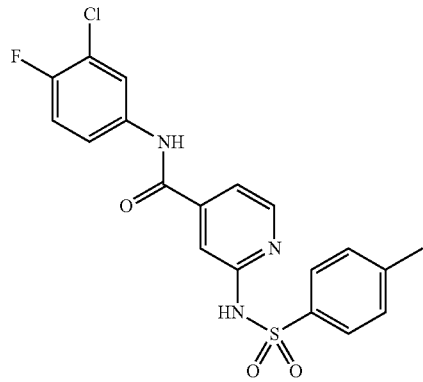 [SMILES: Cc1ccc(S(=O)(=O)Nc2cc(C(=O)Nc3ccc(F)c(Cl)c3)ccn2)cc1]
13
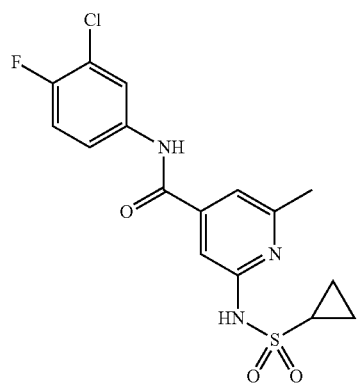 [SMILES: Cc1cc(C(=O)Nc2ccc(F)c(Cl)c2)cc(NS(=O)(=O)C2CC2)n1]
14
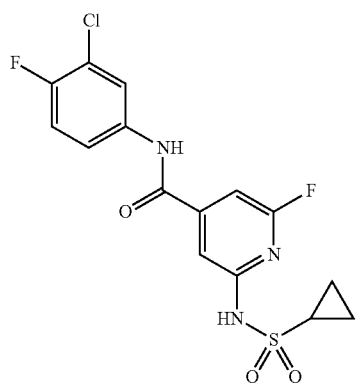 [SMILES: O=C(Nc1ccc(F)c(Cl)c1)c1cc(F)nc(NS(=O)(=O)C2CC2)c1]
15
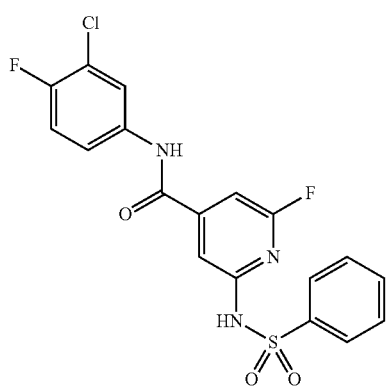 [SMILES: O=C(Nc1ccc(F)c(Cl)c1)c1cc(F)nc(NS(=O)(=O)c2ccccc2)c1]
16
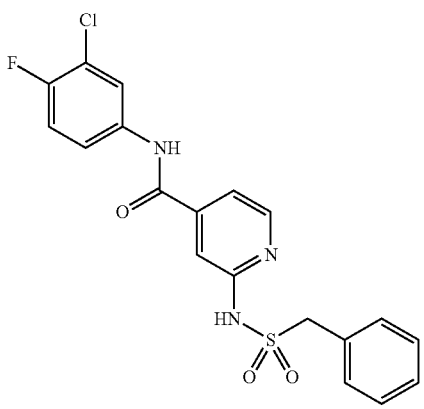 [SMILES: O=C(Nc1ccc(F)c(Cl)c1)c1ccnc(NS(=O)(=O)Cc2ccccc2)c1]
17
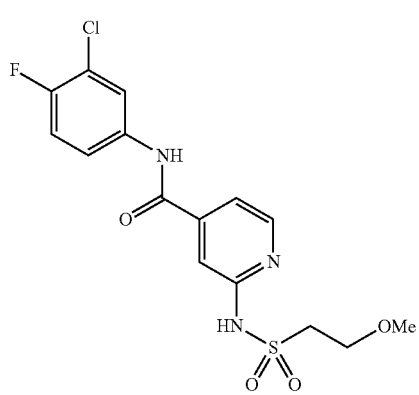 [SMILES: COCCS(=O)(=O)Nc1cc(C(=O)Nc2ccc(F)c(Cl)c2)ccn1]
18
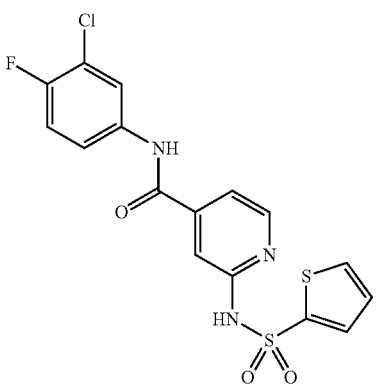 [SMILES: O=C(Nc1ccc(F)c(Cl)c1)c1ccnc(NS(=O)(=O)c2cccs2)c1]
19
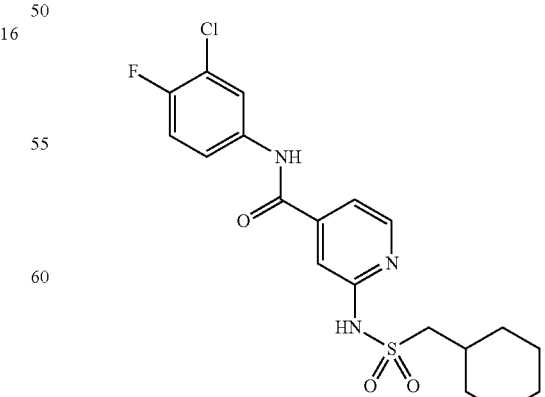
20

TABLE 1-continued
| | |
|---|---|
| 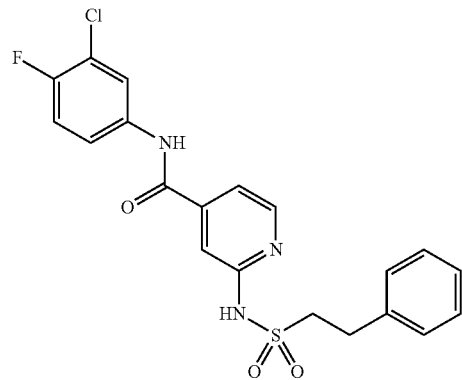 21 | 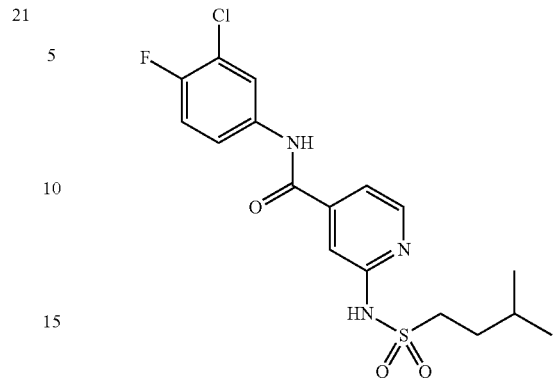 25 |
| 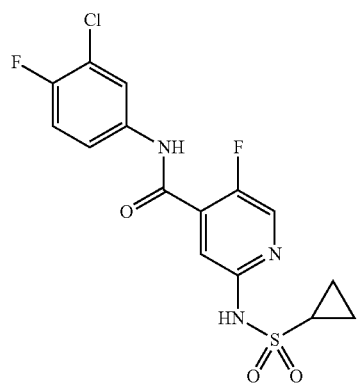 [SMILES: O=C(Nc1ccc(F)c(Cl)c1)c1cc(NS(=O)(=O)C2CC2)ncc1F] 22 | 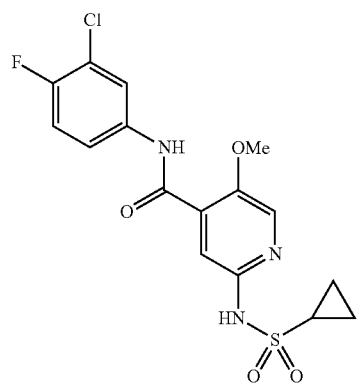 26 |
| 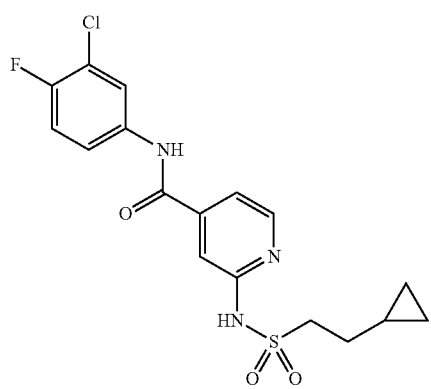 [SMILES: O=C(Nc1ccc(F)c(Cl)c1)c1ccnc(NS(=O)(=O)CCC2CC2)c1] 23 | 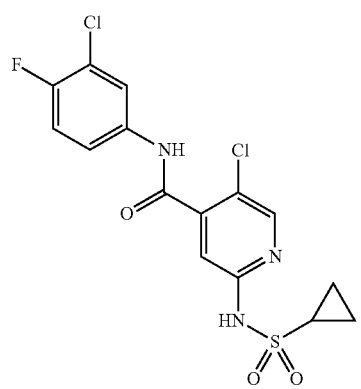 27 |
| 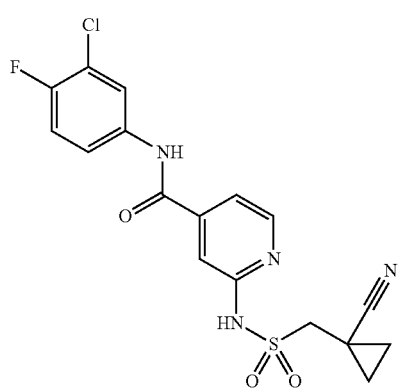 [SMILES: N#CC1(CS(=O)(=O)Nc2cc(C(=O)Nc3ccc(F)c(Cl)c3)ccn2)CC1] 24 | 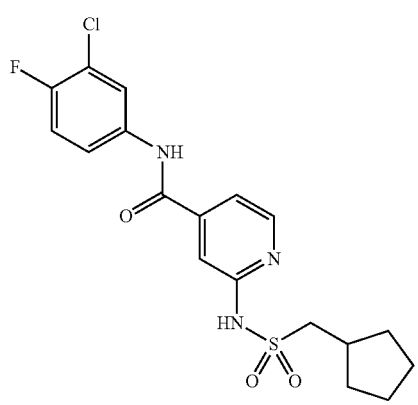 [SMILES: O=C(Nc1ccc(F)c(Cl)c1)c1ccnc(NS(=O)(=O)CC2CCCC2)c1] 28 |

TABLE 1-continued
29
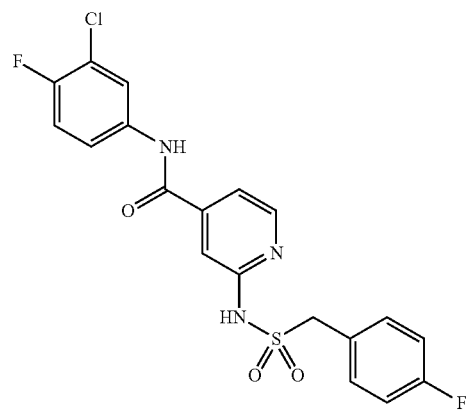 [SMILES: O=C(Nc1ccc(F)c(Cl)c1)c1ccnc(NS(=O)(=O)Cc2ccc(F)cc2)c1]
30
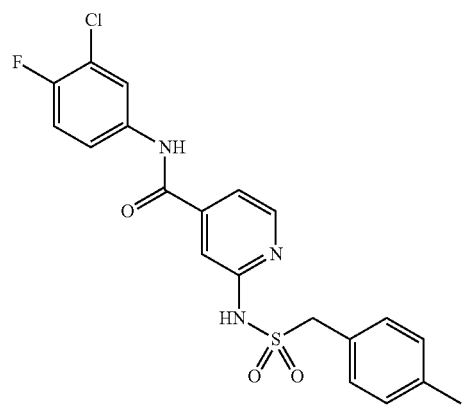 [SMILES: Cc1ccc(CS(=O)(=O)Nc2cc(C(=O)Nc3ccc(F)c(Cl)c3)ccn2)cc1]
31
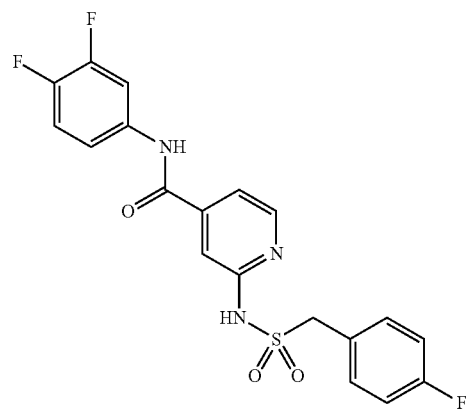
32
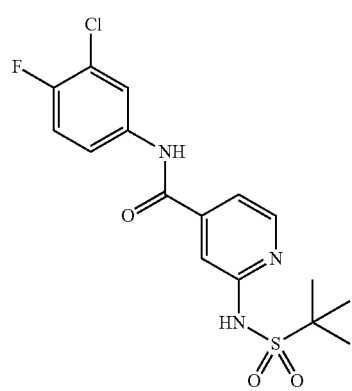 [SMILES: CC(C)(C)S(=O)(=O)Nc1cc(C(=O)Nc2ccc(F)c(Cl)c2)ccn1]
TABLE 1-continued
33
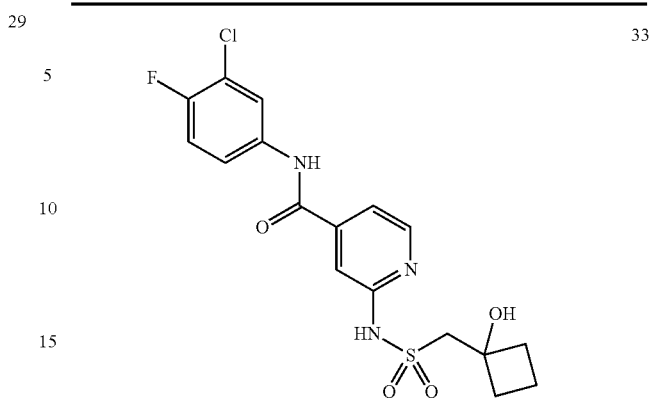
34
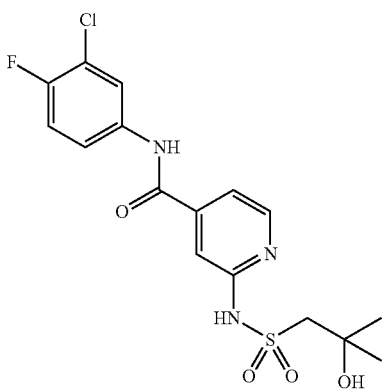 [SMILES: CC(C)(O)CS(=O)(=O)Nc1cc(C(=O)Nc2ccc(F)c(Cl)c2)ccn1]
35
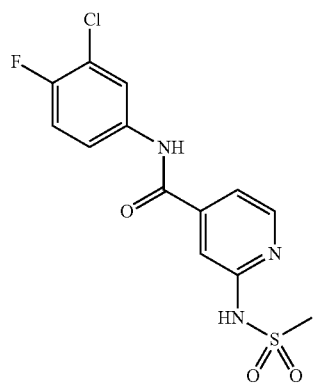 [SMILES: CS(=O)(=O)Nc1cc(C(=O)Nc2ccc(F)c(Cl)c2)ccn1]
36
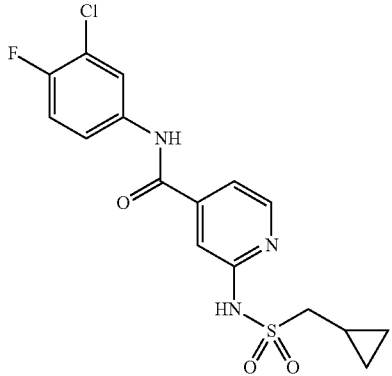 [SMILES: O=C(Nc1ccc(F)c(Cl)c1)c1ccnc(NS(=O)(=O)CC2CC2)c1]

TABLE 1-continued
37 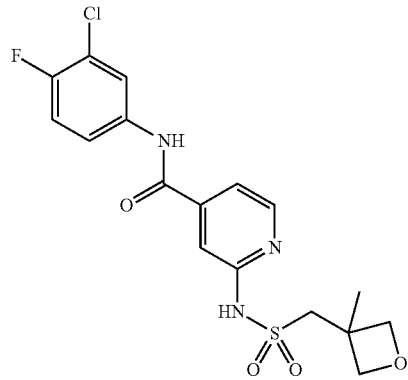 [SMILES: CC1(CS(=O)(=O)Nc2cc(C(=O)Nc3ccc(F)c(Cl)c3)ccn2)COC1]
38 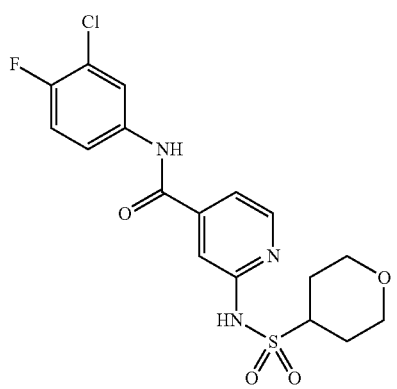 [SMILES: O=C(Nc1ccc(F)c(Cl)c1)c1ccnc(NS(=O)(=O)C2CCOCC2)c1]
39 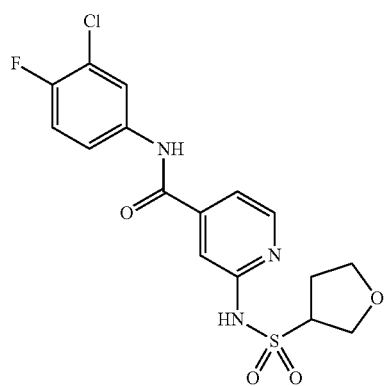 [SMILES: O=C(Nc1ccc(F)c(Cl)c1)c1ccnc(NS(=O)(=O)C2CCOC2)c1]
40 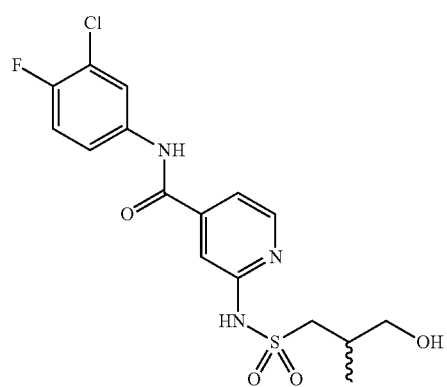 [SMILES: CC(CO)CS(=O)(=O)Nc1cc(C(=O)Nc2ccc(F)c(Cl)c2)ccn1]
TABLE 1-continued
41 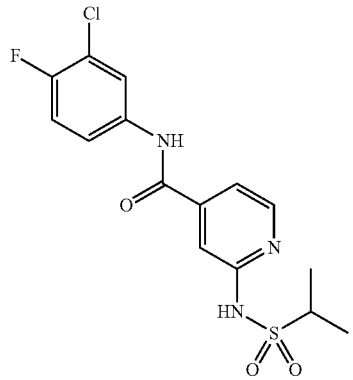 [SMILES: CC(C)S(=O)(=O)Nc1cc(C(=O)Nc2ccc(F)c(Cl)c2)ccn1]
42 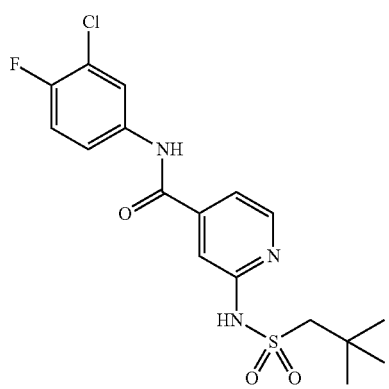 [SMILES: CC(C)(C)CS(=O)(=O)Nc1cc(C(=O)Nc2ccc(F)c(Cl)c2)ccn1]
43 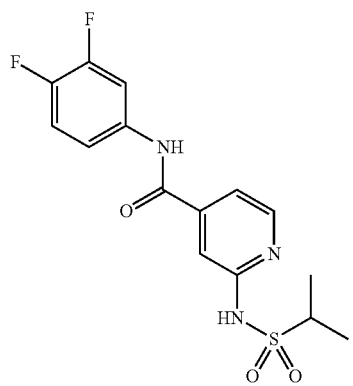
44 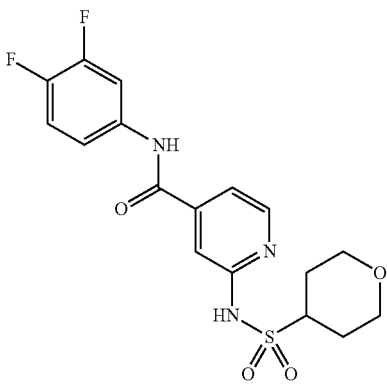 [SMILES: O=C(Nc1ccc(F)c(F)c1)c1ccnc(NS(=O)(=O)C2CCOCC2)c1]

TABLE 1-continued
| 45 | 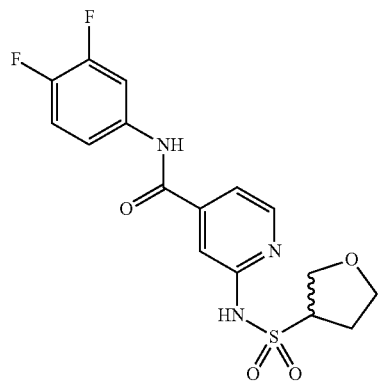 [SMILES: O=C(Nc1ccc(F)c(F)c1)c1ccnc(NS(=O)(=O)C2CCOC2)c1] |
| 46 | 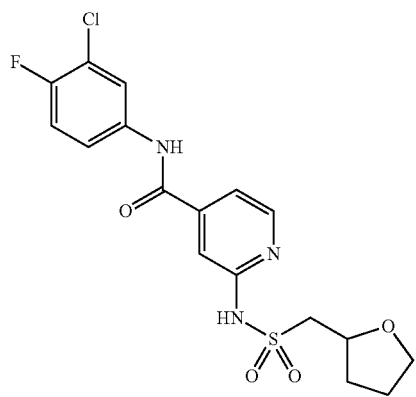 [SMILES: O=C(Nc1ccc(F)c(Cl)c1)c1ccnc(NS(=O)(=O)CC2CCCO2)c1] |
| 47 | 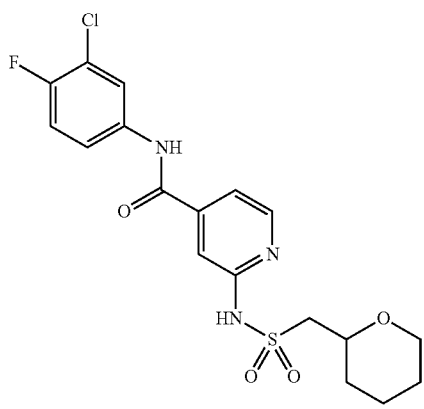 [SMILES: O=C(Nc1ccc(F)c(Cl)c1)c1ccnc(NS(=O)(=O)CC2CCCCO2)c1] |
| 48 | 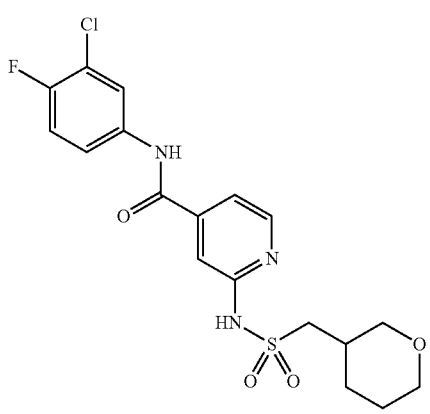 [SMILES: O=C(Nc1ccc(F)c(Cl)c1)c1ccnc(NS(=O)(=O)CC2CCCOC2)c1] |
| 49 | 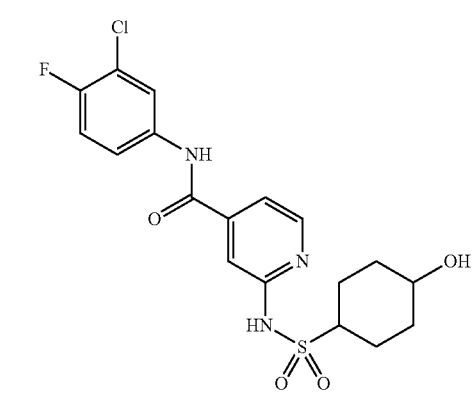 [SMILES: O=C(Nc1ccc(F)c(Cl)c1)c1ccnc(NS(=O)(=O)C2CCC(O)CC2)c1] |
| 50 | 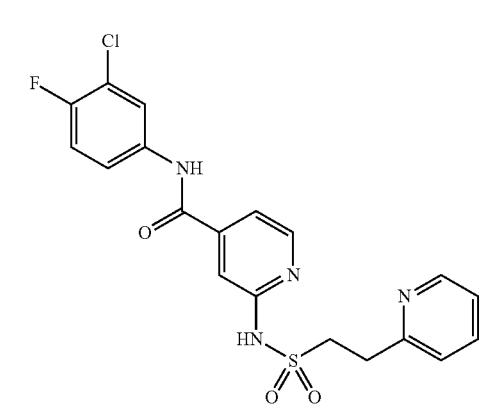 |
| 51 | 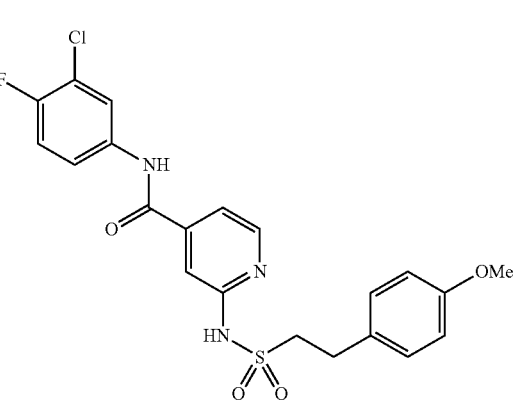 |
| 52 | 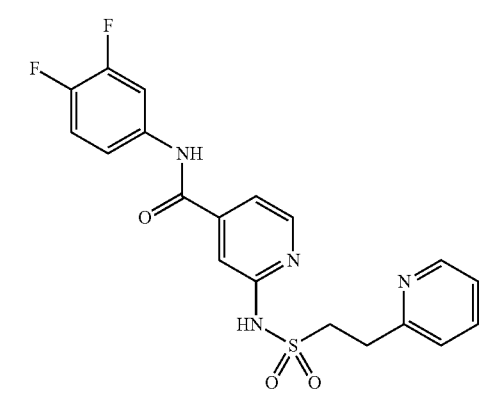 [SMILES: O=C(Nc1ccc(F)c(F)c1)c1ccnc(NS(=O)(=O)CCc2ccccn2)c1] |

TABLE 1-continued
53
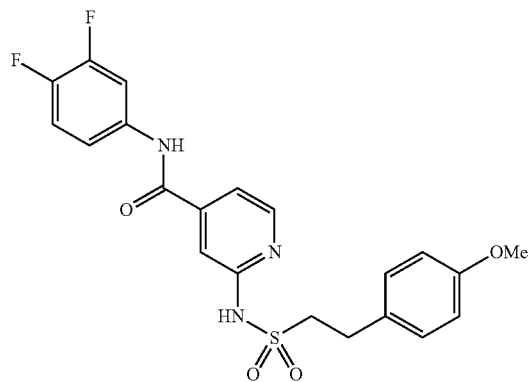 [SMILES: COc1ccc(CCS(=O)(=O)Nc2cc(C(=O)Nc3ccc(F)c(F)c3)ccn2)cc1]
54
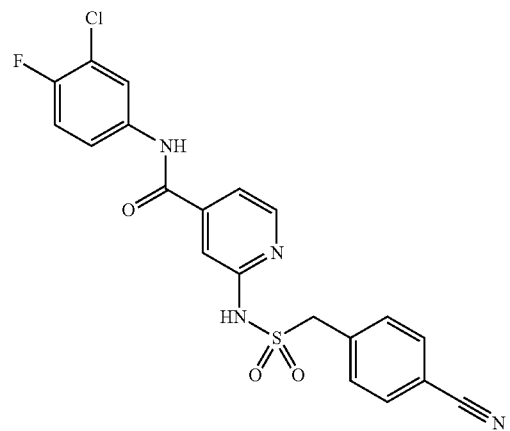 [SMILES: N#Cc1ccc(CS(=O)(=O)Nc2cc(C(=O)Nc3ccc(F)c(Cl)c3)ccn2)cc1]
55
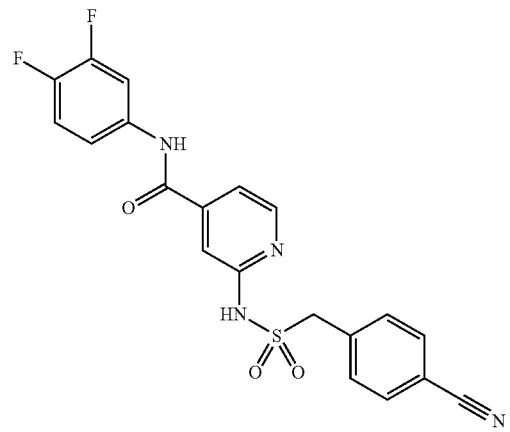 [SMILES: N#Cc1ccc(CS(=O)(=O)Nc2cc(C(=O)Nc3ccc(F)c(F)c3)ccn2)cc1]
56
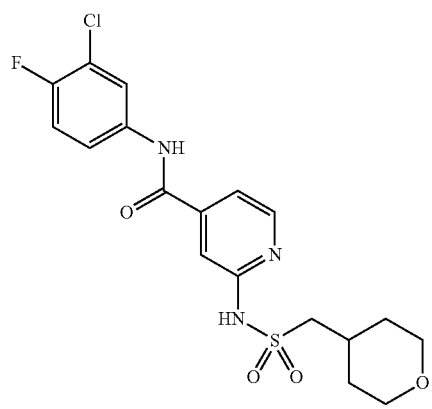 [SMILES: O=C(Nc1ccc(F)c(Cl)c1)c1ccnc(NS(=O)(=O)CC2CCOCC2)c1]
TABLE 1-continued
57
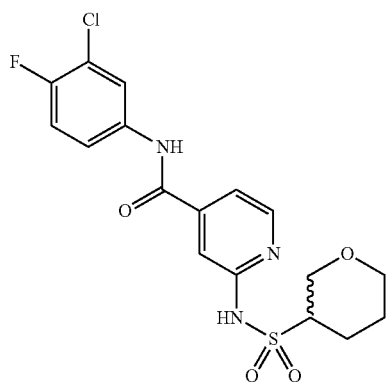 [SMILES: O=C(Nc1ccc(F)c(Cl)c1)c1ccnc(NS(=O)(=O)C2CCCOC2)c1]
58
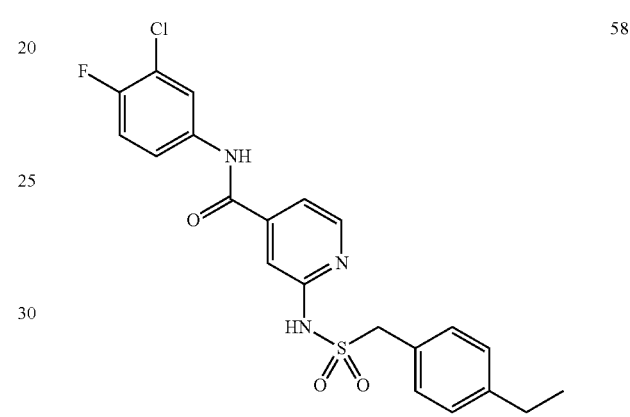
59
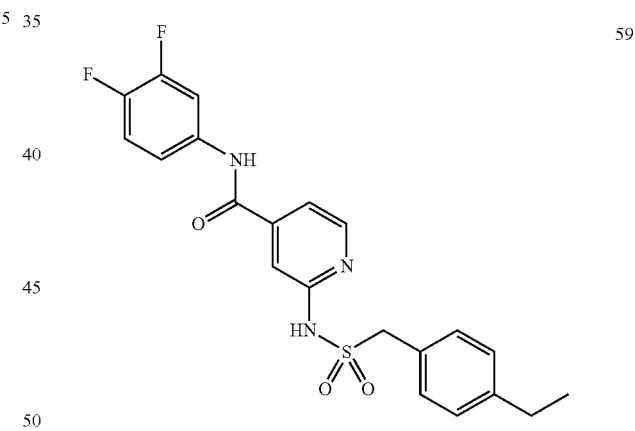
60
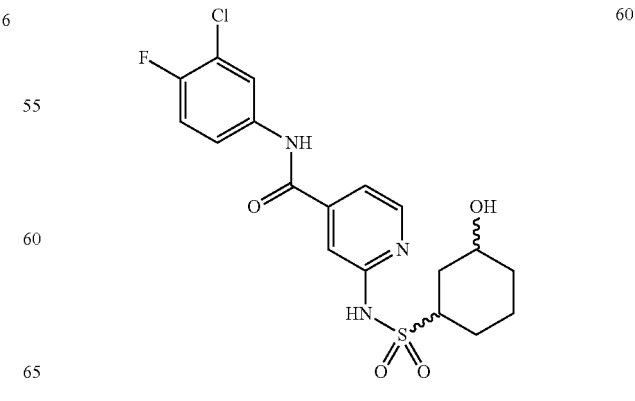

TABLE 1-continued
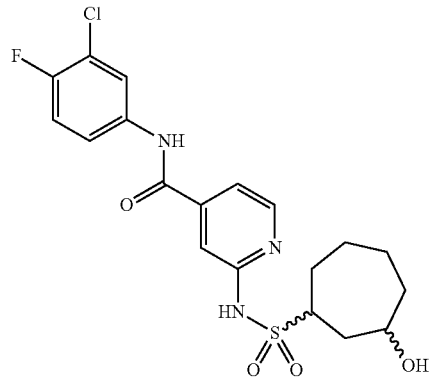 [SMILES: O=C(Nc1ccc(F)c(Cl)c1)c1ccnc(NS(=O)(=O)C2CCCCC(O)C2)c1]
61
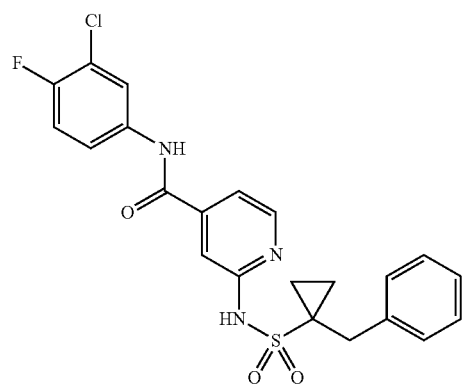 [SMILES: O=C(Nc1ccc(F)c(F)c1)c1ccnc(NS(=O)(=O)C2(Cc3ccccc3)CC2)c1]
62
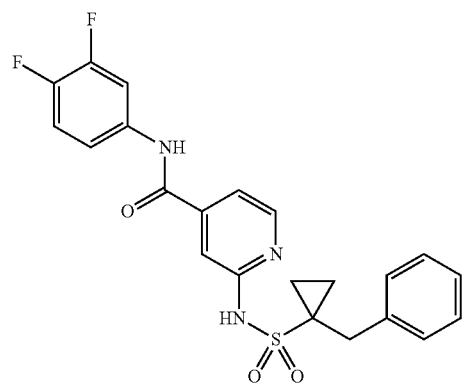
63
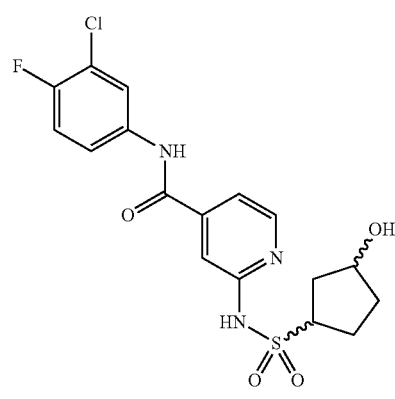 [SMILES: O=C(Nc1ccc(F)c(Cl)c1)c1ccnc(NS(=O)(=O)C2CCC(O)C2)c1]
64
TABLE 1-continued
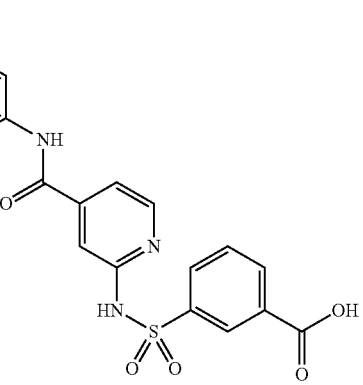
65
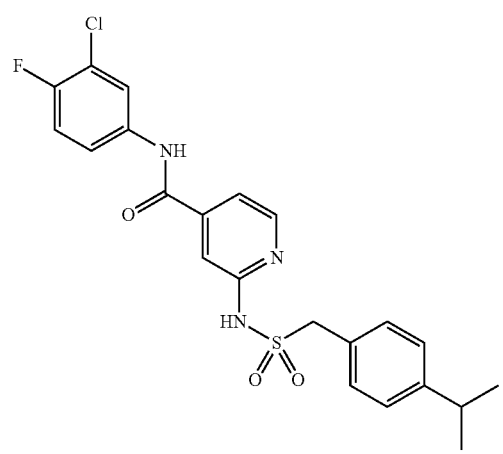
66
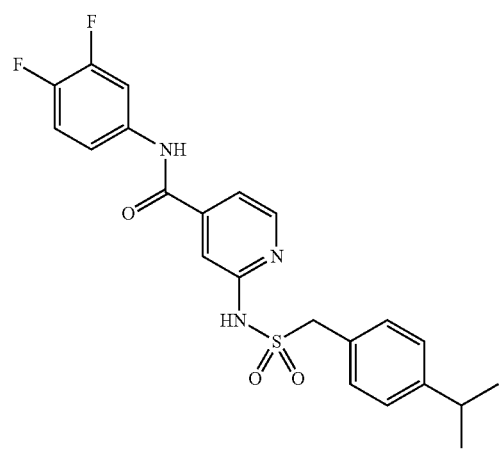 [SMILES: CC(C)c1ccc(CS(=O)(=O)Nc2cc(C(=O)Nc3ccc(F)c(F)c3)ccn2)cc1]
67

TABLE 1-continued
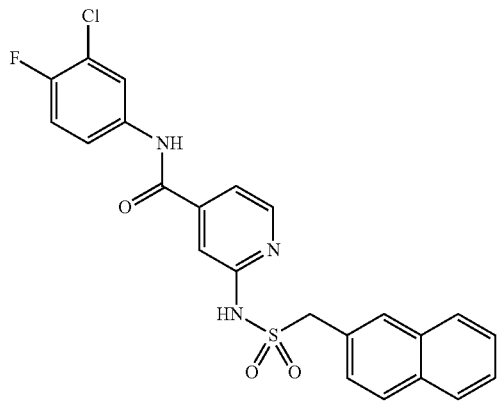 [SMILES: O=C(Nc1ccc(F)c(Cl)c1)c1ccnc(NS(=O)(=O)Cc2ccc3ccccc3c2)c1]
68
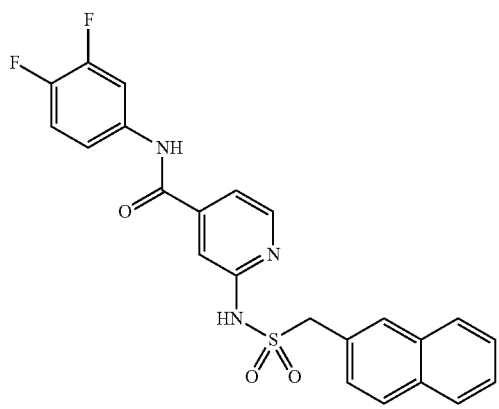 [SMILES: O=C(Nc1ccc(F)c(F)c1)c1ccnc(NS(=O)(=O)Cc2ccc3ccccc3c2)c1]
69
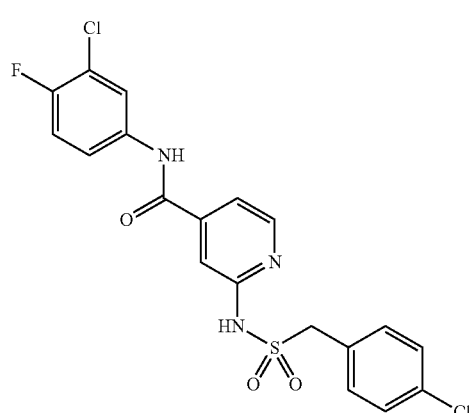
70
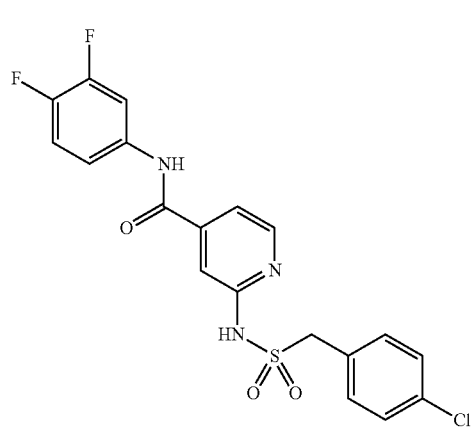 [SMILES: O=C(Nc1ccc(F)c(F)c1)c1ccnc(NS(=O)(=O)Cc2ccc(Cl)cc2)c1]
71
TABLE 1-continued
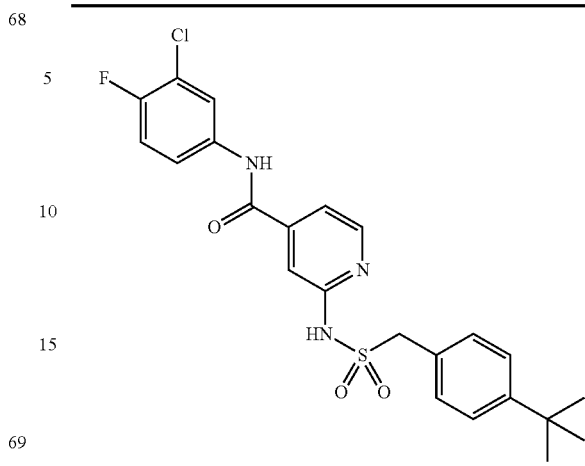
72
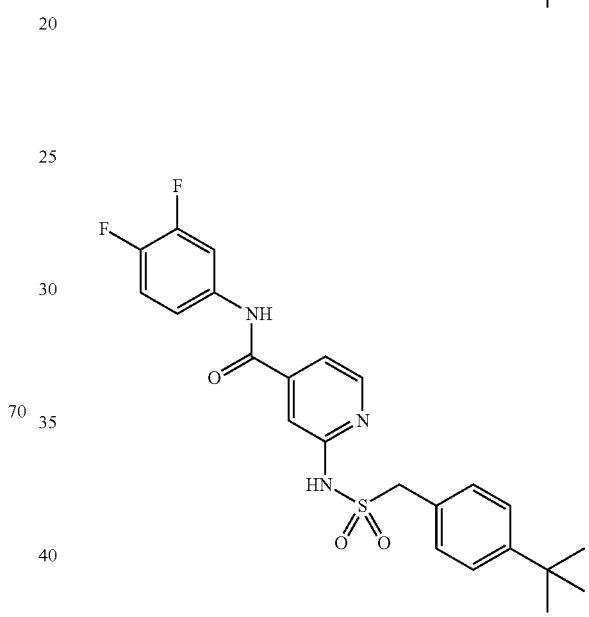
73
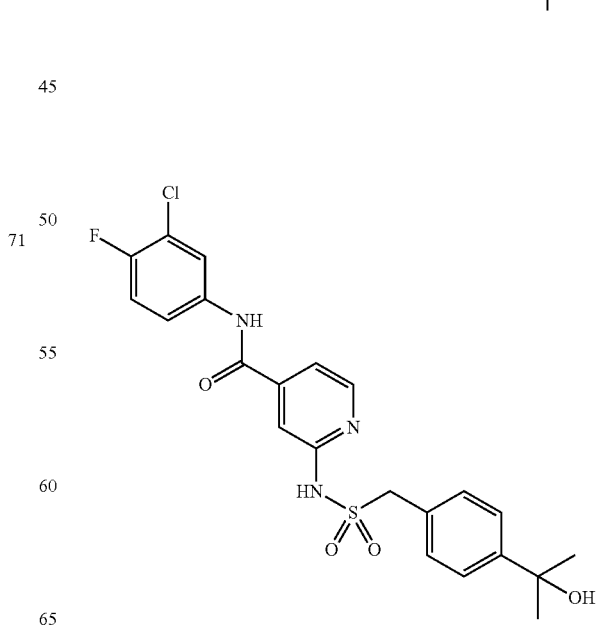
74

TABLE 1-continued
| 75 | 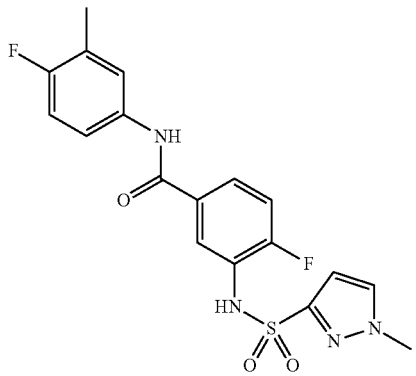 [SMILES: Cc1cc(NC(=O)c2ccc(F)c(NS(=O)(=O)c3ccn(C)n3)c2)ccc1F] |
| --- | --- |
| 76 | 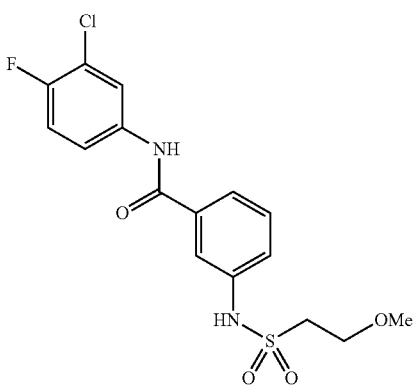 [SMILES: COCCS(=O)(=O)Nc1cccc(C(=O)Nc2ccc(F)c(Cl)c2)c1] |
| 77 | 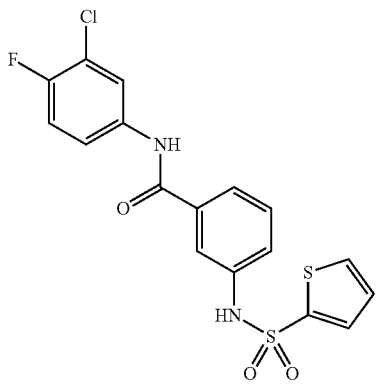 [SMILES: O=C(Nc1ccc(F)c(Cl)c1)c1cccc(NS(=O)(=O)c2cccs2)c1] |
| 78 | 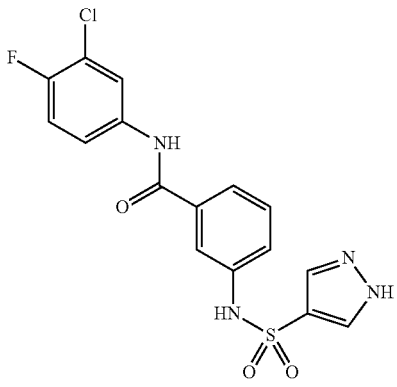 [SMILES: O=C(Nc1ccc(F)c(Cl)c1)c1cccc(NS(=O)(=O)c2cn[nH]c2)c1] |
TABLE 1-continued
| 79 | 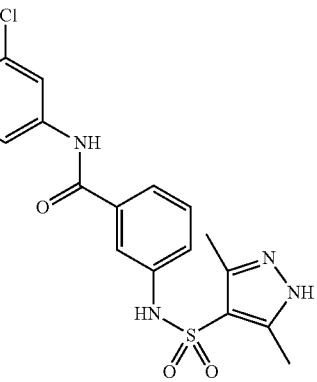 |
| --- | --- |
| 80 | 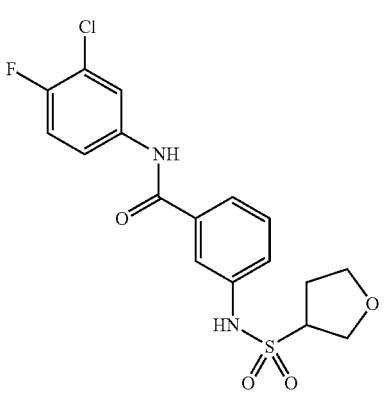 [SMILES: O=C(Nc1ccc(F)c(Cl)c1)c1cccc(NS(=O)(=O)C2CCOC2)c1] |
| 81 | 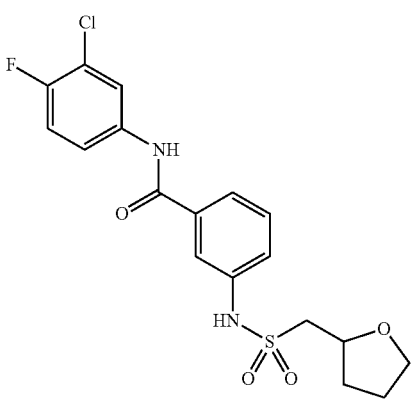 [SMILES: O=C(Nc1ccc(F)c(Cl)c1)c1cccc(NS(=O)(=O)CC2CCCO2)c1] |
| 82 | 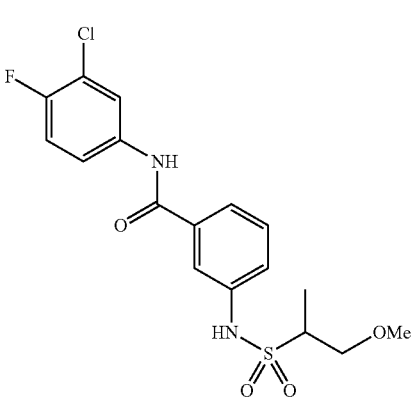 [SMILES: COCC(C)S(=O)(=O)Nc1cccc(C(=O)Nc2ccc(F)c(Cl)c2)c1] |

TABLE 1-continued

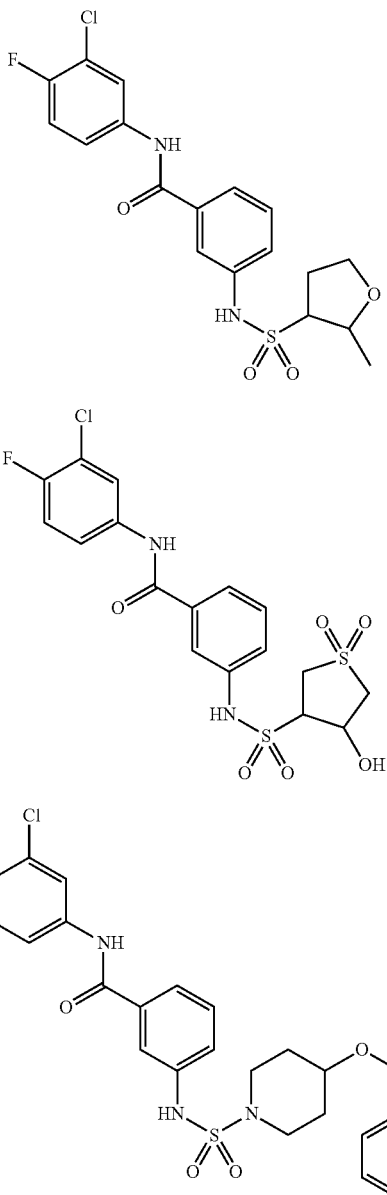

| | |
|---|---|
| 83 | |
| 84 | |
| 85 | |

The invention further includes a composition comprising a compound according to Formula I, Formula Ia, Formula II, or Formula III, or a salt, solvate, or N-oxide thereof. In one embodiment, the composition is pharmaceutical and further comprises at least one pharmaceutically acceptable carrier.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements).

In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

Methods of Treatment

The invention includes a method of treating an HBV infection in an individual in need thereof, comprising administering to the individual a therapeutically effective amount of a compound of the invention.

The invention also includes a method of reducing the viral load associated with an HBV infection in an individual in need thereof, comprising administering to the individual a therapeutically effective amount of a compound of the invention.

The invention further includes a method of reducing reoccurrence of an HBV infection in an individual in need thereof, comprising administering to the individual a therapeutically effective amount of a compound of the invention.

The invention also includes a method of reducing an adverse physiological impact of an HBV infection in an individual in need thereof, comprising administering to the individual a therapeutically effective amount of a compound of the invention.

The invention further includes a method of inducing remission of hepatic injury from an HBV infection in an individual in need thereof, comprising administering to the individual a therapeutically effective amount of a compound of the invention.

The invention also includes a method of reducing the physiological impact of long-term antiviral therapy for HBV infection in an individual in need thereof, comprising administering to the individual a therapeutically effective amount of a compound of the invention.

The invention further includes a method of prophylactically treating an HBV infection in an individual in need thereof, wherein the individual is afflicted with a latent HBV infection, comprising administering to the individual a therapeutically effective amount of a compound of the invention.

In one embodiment, the methods described herein comprise administering to the individual at least one additional therapeutic agent selected from the group consisting of an HBV vaccine, HBV polymerase inhibitor, interferon, pegylated interferon, viral entry inhibitor, viral maturation inhibitor, capsid assembly modulator, reverse transcriptase inhibitor, a TLR-agonist, and agents of distinct or unknown mechanism, and a combination thereof. In another embodiment, the pegylated interferon is pegylated interferon alpha (IFN-α), pegylated interferon lambda (IFN-λ), or pegylated interferon gamma (IFN-γ). In still another embodiment, the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine. In yet another embodiment, the compound and the at least one additional therapeutic agent are co-formulated. In still another embodiment, the compound and the at least one additional therapeutic agent are co-administered.

In another embodiment, provided herein is a method of treating an HBV infection in an individual in need thereof, comprising administering to the individual a therapeutically effective amount of compound of Formula I, or a pharmaceutically acceptable salt thereof. In another embodiment, provided herein is a method of treating an HBV infection in an individual in need thereof, comprising administering to the individual a therapeutically effective amount of compound of Formula Ia, or a pharmaceutically acceptable salt thereof. In another embodiment, provided herein is a method of treating an HBV infection in an individual in need thereof, comprising administering to the individual a therapeutically effective amount of compound of Formula II, or a pharmaceutically acceptable salt thereof. In another embodiment, provided herein is a method of treating an HBV infection in an individual in need thereof, comprising administering to the individual a therapeutically effective amount of compound of Formula III, or a pharmaceutically acceptable salt thereof.

In another embodiment, provided herein is a method of treating an HBV infection in an individual in need thereof, comprising administering to the individual a therapeutically effective amount of compound 2, or a pharmaceutically acceptable salt thereof.

In another embodiment, provided herein is a method of treating an HBV infection in an individual in need thereof, comprising administering to the individual a therapeutically effective amount of compound 6, or a pharmaceutically acceptable salt thereof.

In another embodiment, provided herein is a method of treating an HBV infection in an individual in need thereof, comprising administering to the individual a therapeutically effective amount of compound 8, or a pharmaceutically acceptable salt thereof.

In another embodiment, provided herein is a method of treating an HBV infection in an individual in need thereof, comprising administering to the individual a therapeutically effective amount of compound 9, or a pharmaceutically acceptable salt thereof.

In another embodiment, provided herein is a method of treating an HBV infection in an individual in need thereof, comprising administering to the individual a therapeutically effective amount of compound 11, or a pharmaceutically acceptable salt thereof.

In another embodiment, provided herein is a method of treating an HBV infection in an individual in need thereof, comprising administering to the individual a therapeutically effective amount of compound 28, or a pharmaceutically acceptable salt thereof.

In another embodiment, provided herein is a method of treating an HBV infection in an individual in need thereof, comprising administering to the individual a therapeutically effective amount of compound 41, or a pharmaceutically acceptable salt thereof.

In another embodiment, provided herein is a method of treating an HBV infection in an individual in need thereof, comprising administering to the individual a therapeutically effective amount of compound 58, or a pharmaceutically acceptable salt thereof.

In another embodiment, provided herein is a method of treating an HBV infection in an individual in need thereof, comprising administering to the individual a therapeutically effective amount of compound 59, or a pharmaceutically acceptable salt thereof.

In another embodiment, provided herein is a method of treating an HBV infection in an individual in need thereof, comprising administering to the individual a therapeutically effective amount of compound 66, or a pharmaceutically acceptable salt thereof.

In another embodiment, provided herein is a method of treating an HBV infection in an individual in need thereof, comprising administering to the individual a therapeutically effective amount of compound 67, or a pharmaceutically acceptable salt thereof.

In another embodiment, provided herein is a method of treating an HBV infection in an individual in need thereof, comprising administering to the individual a therapeutically effective amount of compound 72, or a pharmaceutically acceptable salt thereof.

In another embodiment, provided herein is a method of treating an HBV infection in an individual in need thereof, comprising administering to the individual a therapeutically effective amount of compound 73, or a pharmaceutically acceptable salt thereof.

In another embodiment, provided herein is a method of treating an HBV infection in an individual in need thereof, comprising administering to the individual a therapeutically effective amount of compound 75, or a pharmaceutically acceptable salt thereof.

In another embodiment, provided herein is a method of treating an HBV infection in an individual in need thereof, comprising administering to the individual a therapeutically effective amount of compound 76, or a pharmaceutically acceptable salt thereof.

In another embodiment, provided herein is a method of treating an HBV infection in an individual in need thereof, comprising administering to the individual a therapeutically effective amount of compound 77, or a pharmaceutically acceptable salt thereof.

In another embodiment, provided herein is a method of treating an HBV infection in an individual in need thereof, comprising administering to the individual a therapeutically effective amount of compound 78, or a pharmaceutically acceptable salt thereof.

In another embodiment, provided herein is a method of treating an HBV infection in an individual in need thereof, comprising administering to the individual a therapeutically effective amount of compound 79, or a pharmaceutically acceptable salt thereof.

In another embodiment, provided herein is a method of treating an HBV infection in an individual in need thereof, comprising administering to the individual a therapeutically effective amount of compound 80, or a pharmaceutically acceptable salt thereof.

In another embodiment, provided herein is a method of treating an HBV infection in an individual in need thereof, comprising administering to the individual a therapeutically effective amount of compound 81, or a pharmaceutically acceptable salt thereof.

In another embodiment, provided herein is a method of treating an HBV infection in an individual in need thereof, comprising administering to the individual a therapeutically effective amount of compound 82, or a pharmaceutically acceptable salt thereof.

In another embodiment, provided herein is a method of treating an HBV infection in an individual in need thereof, comprising administering to the individual a therapeutically effective amount of compound 83, or a pharmaceutically acceptable salt thereof.

In another embodiment, provided herein is a method of treating an HBV infection in an individual in need thereof, comprising administering to the individual a therapeutically effective amount of compound 84, or a pharmaceutically acceptable salt thereof.

In another embodiment, provided herein is a method of treating an HBV infection in an individual in need thereof, comprising administering to the individual a therapeutically effective amount of compound 85, or a pharmaceutically acceptable salt thereof.

Combination Therapies

The compounds of the present invention are intended to be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, viral entry inhibitors, viral maturation inhibitors, literature-described capsid assembly modulators, and other agents with distinct or unknown mechanisms that affect the HBV life cycle and/or affect the consequences of HBV infection.

In non-limiting examples, the compounds of the invention may be used in combination with one or more drugs (or a salt, solvate or prodrug thereof) selected from the group consisting of:

HBV reverse transcriptase inhibitors, and DNA and RNA polymerase inhibitors, including but are not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons, including but not limited to interferon alpha (IFN-α), interferon lambda (IFN-λ), and interferon gamma (IFN-γ);

viral entry inhibitors;

viral maturation inhibitors;

literature-described capsid assembly modulators, such as but not limited to BAY 41-4109;

compounds of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In another embodiment, the additional therapeutic agent selected from immune modulator or immune stimulator therapies, which includes biological agents belonging to the interferon class, such as interferon alpha 2a or 2b or modified interferons such as pegylated interferon, alpha 2a, alpha 2b, lamda; or TLR modulators such as TLR-7 agonists or TLR-9 agonists, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence.

In an embodiment of the combination therapy, the reverse transcriptase inhibitor and/or DNA and/or RNA polymerase inhibitor Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl]acetate).

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a HBV infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat HBV infection in the patient. An effective amount of the therapeutic compound necessary to achieve a therapeutic effect may vary according to factors such as the state of the disease or disorder in the patient; the age, sex, and weight of the patient; and the ability of the therapeutic compound to treat HBV infection in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating Parkinson's Disease) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HBV infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Dosing

The therapeutically effective amount or dose of a compound of the present invention will depend on the age, sex and weight of the patient, the current medical condition of the patient and the progression of HBV infection in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

Once improvement of the patient's conditions has occurred, a maintenance dose is administered if necessary. Subsequently, the dosage or the frequency of administration, or both, is reduced, as a function of the viral load, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. Capsid assembly inhibitors exhibiting high therapeutic indices are preferred. The data obtained from cell culture assays and animal studies is optionally used in formulating a range of dosage for use in human. The dosage of such capsid assembly inhibitors lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example: Preparation of the Compounds of the Invention

Figure 2:
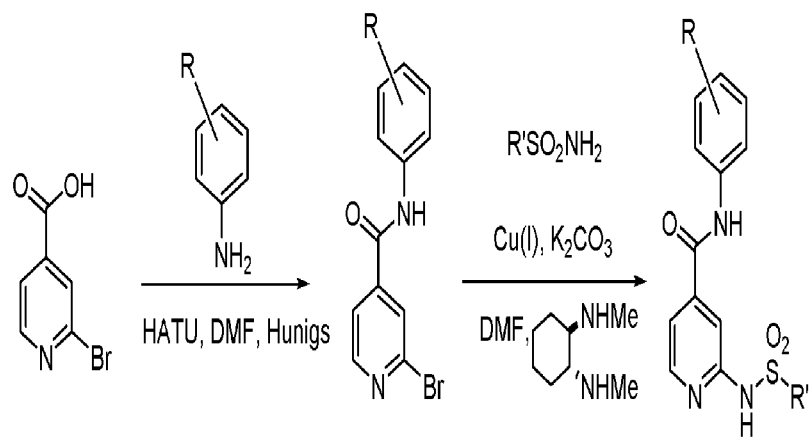
FIG. 2 shows a second general scheme used to prepare selected compounds of the invention.
Figure 3:
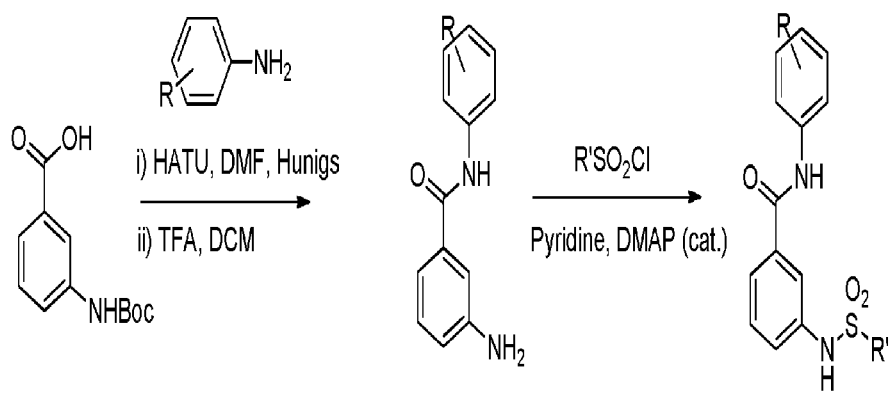
FIG. 3 shows a third general scheme used to prepare selected compounds of the invention.

FIGS. 1-3 show general schemes used to prepare selected compounds of the invention.

Intermediate A

2-Bromo-N-(3-chloro-4-fluorophenyl)isonicotinamide

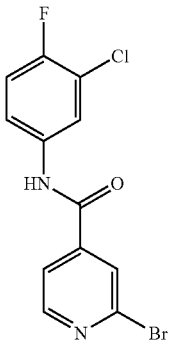

To a stirring solution of 2-bromoisonicotinic acid (6.00 g, 29.70 mmol) in anhydrous DMF (100 mL) was added HATU (13.55 g, 35.64 mmol), 3-chloro-4-fluoroaniline (4.54 g, 31.19 mmol), Hünigs base (15.56 mL, 89.10 mmol) and a catalytic amount of DMAP. The resulting mixture was stirred at rt for 16 h. The reaction was diluted with EtOAc and brine. The organic phase was then washed once more with brine, 0.5M HCl (2×), water and concentrated in vacuo. The resulting crude solid was suspended in DCM, stirred for 20 min, and filtered. The subsequent solid afforded the title compound in pure form. LC-MS: 330 (M+H)$^+$.

Intermediate B

2-Bromo-N-(3,4,5-trifluorophenyl)isonicotinamide

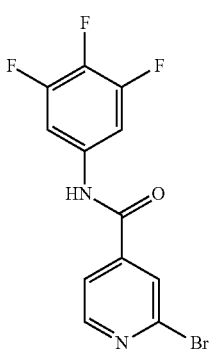

The title compound was prepared in an analogous manner to Intermediate A using 3,4,5-trifluoroaniline. LC-MS: 332 (M+H)$^+$.

Intermediate C

2-Bromo-N-(3,4-difluorophenyl)isonicotinamide

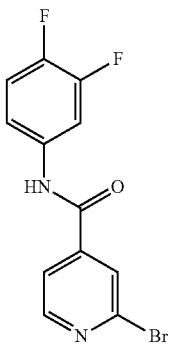 [SMILES: O=C(Nc1ccc(F)c(F)c1)c1ccnc(Br)c1]

The title compound was prepared in an analogous manner to Intermediate A using 3,4-difluoroaniline. LC-MS: 314 (M+H)$^+$.

Intermediate D

2-Amino-N-(3-chloro-4-fluorophenyl)isonicotinamide

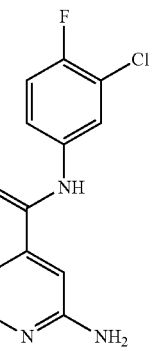

To a stirring solution of 2-aminoisonicotinic acid (5.00 g, 36.2 mmol) in anhydrous DMF (100 mL) was added HATU (16.5 g, 35.64 mmol), 3-chloro-4-fluoroaniline (5.27 g, 36.2 mmol), diisopropylethylamine (19 mL, 110 mmol) and dimethylaminopyridine (750 mg, 6.1 mmol). The resulting mixture was stirred at RT for 16 hrs then diluted with EtOAc and saturated aqueous NaHCO$_3$. The organics were then washed with brine, dried over MgSO$_4$ and partially concentrated in vacuo. The resulting solid that crashed out was filtered and found to be pure title compound. The filtrate was concentrated and purified by c18 silica gel chromatography, eluting with a gradient of 5% to 100% MeCN in water containing 0.5% formic acid. Product containing fractions were concentrated, diluted with saturated aqueous NaHCO$_3$ and extracted with EtOAc. The organics were then dried over MgSO$_4$ and concentrated in vacuo to afford additional title compound. LC-MS: 266 (M+H)$^+$.

Intermediate E

2-Amino-N-(3,4-difluorophenyl)isonicotinamide

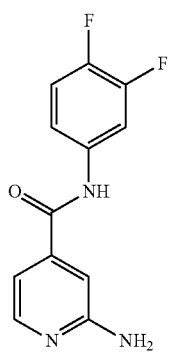 [SMILES: Nc1cc(C(=O)Nc2ccc(F)c(F)c2)ccn1]

Prepared in analogous fashion to Intermediate D using 3,4-difluoroaniline.

Intermediate F 2-(Cyclopropanesulfonamido)isonicotinic acid

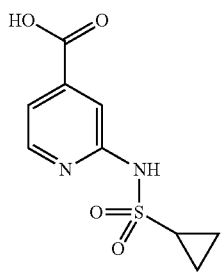

Step 1; To a solution of methyl 2-aminoisonicotinate (0.408 g, 2.68 mmol) in anhydrous pyridine (10 mL) was added dimethylaminopyridine (0.01 g, 0.08 mmol) and cyclopropanesulfonyl chloride (0.27 mL, 2.7 mmol). The resulting mixture was heated to 60° C. for 16 hrs. Volatiles were removed in vacuo and the residue was diluted with EtOAc and 1N HCl. The organics were washed with 1N HCl (2×), brine, dried over MgSO$_4$, filtered and concentrated in vacuo. The resulting crude material was purified on silica gel eluting with a solvent gradient of 0% to 100% EtOAc in hexanes to afford methyl 2-(cyclopropanesulfonamido) isonicotinate.

Step 2; To a solution of methyl 2-(cyclopropanesulfonamido)isonicotinate (0.400 g, 1.56 mmol) in methanol (10 mL) and tetrahydrofuran (20 mL) was added 3N NaOH (10 mL) and the resulting mixture was stirred for 1 h. The reaction mixture was acidified with 1N HCl and extracted with EtOAc (2×). The combined organics were washed with brine, dried over MgSO$_4$ and the volatiles were removed in vacuo to provide the title compound. LC-MS: 243 (M+H)$^+$.

Intermediate G 5-(Cyclopropanesulfonamido)nicotinic acid

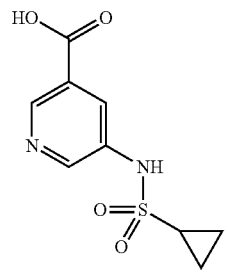 [SMILES: O=C(O)c1cncc(NS(=O)(=O)C2CC2)c1]

The title compound was prepared in an analogous manner to Intermediate F using methyl 5-aminonicotinate as a starting material. LC-MS: 243 (M+H)$^+$.

Intermediate H 6-(Cyclopropanesulfonamido)picolinic acid

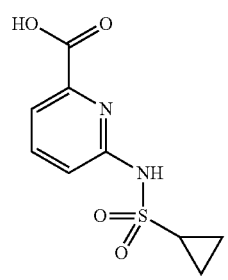 [SMILES: O=C(O)c1cccc(NS(=O)(=O)C2CC2)n1]

The title compound was prepared in an analogous manner to Intermediate F using methyl 6-aminopicolinate as a starting material. LC-MS: 243 (M+H)$^+$.

Intermediate I 3-amino-N-(3-chloro-4-fluorophenyl)benzamide

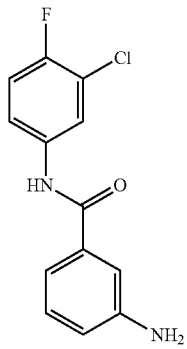 [SMILES: Nc1cccc(C(=O)Nc2ccc(F)c(Cl)c2)c1]

To a solution of 3-((tert-butoxycarbonyl)amino)benzoic acid (1 g, 4.21 mmol) in DMF (10 mL) was added 3-chloro-4-fluoroaniline (613 mg, 4.21 mmol), N,N-diisopropylethylamine (1.47 mL, 8.42 mmol) and HATU (1.76 g, 4.63 mmol). Catalytic DMAP was added (~20 mg) and the reaction mixture stirred at room temperature for 16 hrs. The solution was diluted with EtOAc and washed with 1N HCl, brine and the organic phase separated, dried (MgSO$_4$), filtered and evaporated in vacuo. The isolated solid was purified using silica gel chromatography eluting with 0 to 40% EtOAc in hexanes to afford the intermediate tert-butyl (3-((3-chloro-4-fluorophenyl)carbamoyl)phenyl)carbamate as a colorless solid. This was dissolved in dichloromethane (15 mL) to which was added TFA (5 mL) and the reaction mixture stirred at room temperature until LCMS analysis determined complete reaction. The solution was then diluted with EtOAc, quenched with the addition of saturated aqueous NaHCO$_3$, the organic phase separated, dried (MgSO$_4$), filtered and evaporated in vacuo to afford the title compound.

Compound 1

N-(3-Chloro-4-fluorophenyl)-6-(cyclopropanesulfonamido)picolinamide

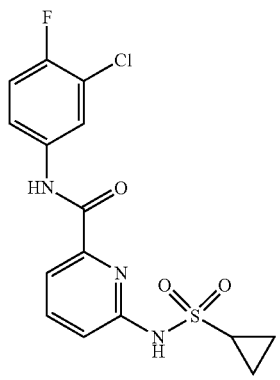 [SMILES: O=C(Nc1ccc(F)c(Cl)c1)c1cccc(NS(=O)(=O)C2CC2)n1]

The title compound was prepared in an analogous manner to Compound 2 using Intermediate H as a starting material. LC-MS: 370 (M+H)$^+$.

Compound 2

N-(3-Chloro-4-fluorophenyl)-2-(cyclopropanesulfonamido)isonicotinamide

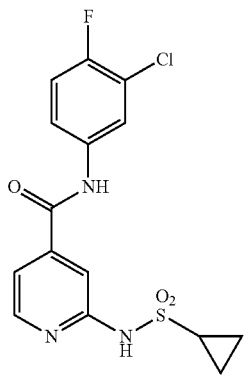 [SMILES: O=C(Nc1ccc(F)c(Cl)c1)c1ccnc(NS(=O)(=O)C2CC2)c1]

To a mixture of copper(I) iodide (0.23 g, 1.21 mmol), potassium carbonate (1.68 g, 12.14 mmol) and cyclopropylsulfonamide (0.809 g, 6.67 mmol) in a RBF under nitrogen atmosphere was added DMF (60 mL), trans-(1R,2R)—N,N'-bismethyl-1,2-cyclohexanediamine (0.344 g, 2.42 mmol) and 2-bromo-N-(3-chloro-4-fluorophenyl)isonicotinamide (Intermediate A) (2.00 g, 6.07 mmol). The resulting mixture was sub-surface purged with nitrogen gas for 10 minutes before heating to 100° C. for 16 h. The reaction was cooled to RT and diluted with EtOAc and 0.5M HCl. The organics were washed twice with 0.5M HCl, water (2×) and concentrated in vacuo. The resulting crude solid was suspended in DCM, stirred for 1 hr and filtered. The resulting solid afforded the title compound in pure form. LC-MS: 370 (M+H)$^+$.

Compound 3

N-(3-Chloro-4-fluorophenyl)-5-(cyclopropanesulfonamido)nicotinamide

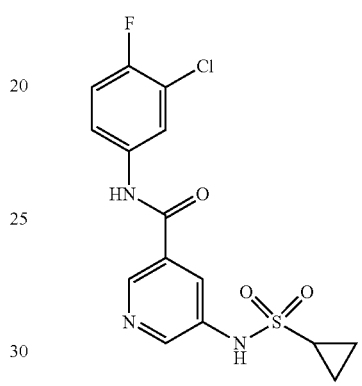

To a stirring solution of Intermediate G (0.077 g, 0.32 mmol) in anhydrous DMF (3 mL) was added HATU (0.150 g, 0.38 mmol), 3-chloro-4-fluoroaniline (0.046 g, 0.32 mmol), diisopropylethylamine (0.17 mL, 0.95 mmol) and dimethylaminopyridine (0.01 g, 0.08 mmol). The resulting mixture was stirred at RT for 4 h then diluted with EtOAc and water. The organic layer was washed with brine, dried over MgSO$_4$ and concentrated in vacuo. The residue was purified by silica gel chromatography eluting with a gradient of 0% to 100% EtOAc in hexanes to provide the title compound. LC-MS: 370 (M+H)$^+$.

Compound 4

N-(3-Chloro-4-fluorophenyl)-4-(cyclopropanesulfonamido)picolinamide

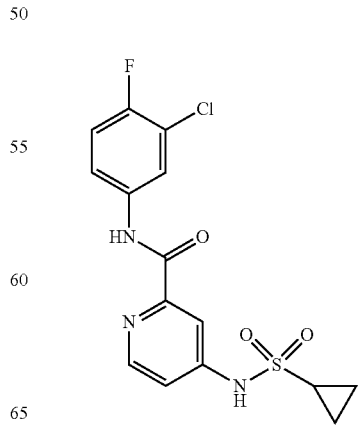

The title compound was prepared in an analogous manner to Compound 14 using 2-bromopyridin-4-amine as a starting material. LC-MS: 370 (M+H)⁺.

Compound 5

2-(Cyclopropanesulfonamido)-N-(3,4,5-trifluorophenyl)isonicotinamide

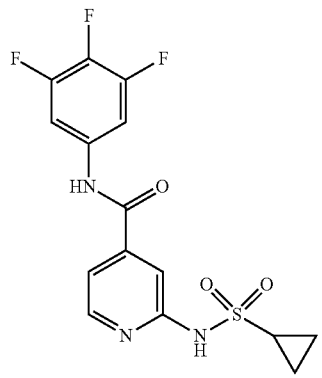 [SMILES: O=C(Nc1cc(F)c(F)c(F)c1)c1ccnc(NS(=O)(=O)C2CC2)c1]

The title compound was prepared in an analogous manner to Compound 3 using 3,4,5-trifluoroaniline and Intermediate F as a starting materials. LC-MS: 372 (M+H)⁺.

Compound 6

2-(Cyclopropanesulfonamido)-N-(3,4-difluorophenyl)isonicotinamide

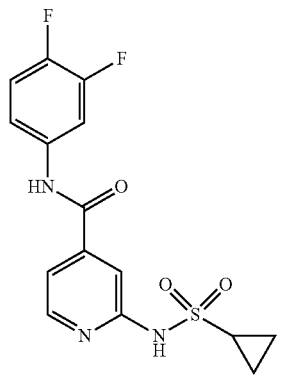 [SMILES: O=C(Nc1ccc(F)c(F)c1)c1ccnc(NS(=O)(=O)C2CC2)c1]

The title compound was prepared in an analogous manner to Compound 3 using 3,4-difluoroaniline and Intermediate F as a starting materials. LC-MS: 354 (M+H)⁺.

Compound 7

N-(3-Cyano-4-fluorophenyl)-2-(cyclopropanesulfonamido)isonicotinamide

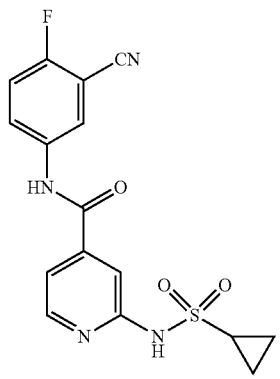 [SMILES: N#Cc1cc(NC(=O)c2ccnc(NS(=O)(=O)C3CC3)c2)ccc1F]

The title compound was prepared in an analogous manner to Compound 3 using 5-amino-2-fluorobenzonitrile and Intermediate F as starting materials. LC-MS: 361 (M+H)⁺.

Compound 8

N-(3-Chloro-4-fluorophenyl)-2-(1-methylcyclopropanesulfonamido)isonicotinamide

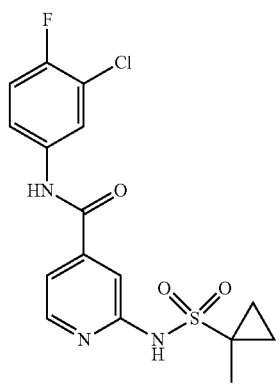 [SMILES: CC1(S(=O)(=O)Nc2cc(C(=O)Nc3ccc(F)c(Cl)c3)ccn2)CC1]

To a solution of Intermediate D (0.150 g, 0.57 mmol) in anhydrous pyridine (5 mL) was added dimethylaminopyridine (0.01 g, 0.08 mmol) and 1-methylcyclopropane-1-sulfonyl chloride (0.081 mL, 0.68 mmol). The resulting mixture was heated to 60° C. for 16 hrs. Volatiles were removed in vacuo and the residue was diluted with EtOAc and 1N HCl. The organics were washed with 1N HCl (2×), brine, dried over MgSO₄, filtered and concentrated in vacuo. The resulting crude material was purified on silica gel eluting with a solvent gradient of 0% to 100% EtOAc in hexanes to provide the title compound. LC-MS: 384 (M+H)⁺.

Compound 9

N-(3-Chloro-4-fluorophenyl)-2-(1-methylcyclopropanesulfonamido)isonicotinamide

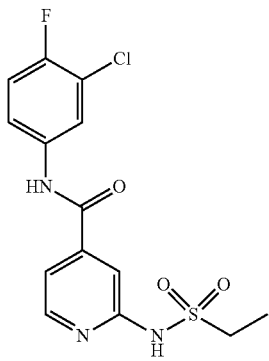 [SMILES: CCS(=O)(=O)Nc1cc(C(=O)Nc2ccc(F)c(Cl)c2)ccn1]

The title compound was prepared in an analogous manner to Compound 8 using ethanesulfonyl chloride as a starting material. LC-MS: 358 (M+H)⁺.

Compound 10

N-(3-Chloro-4-fluorophenyl)-2-(3,3,3-trifluoropropylsulfonamido)isonicotinamide

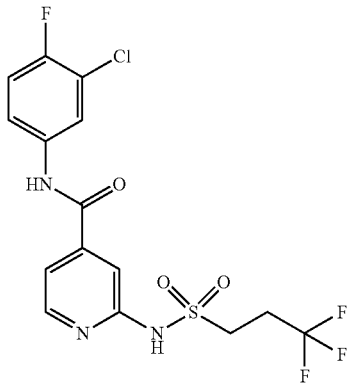 [SMILES: O=C(Nc1ccc(F)c(Cl)c1)c1ccnc(NS(=O)(=O)CCC(F)(F)F)c1]

The title compound was prepared in an analogous manner to Compound 8 using 3,3,3-trifluoropropane-1-sulfonyl chloride as a starting material. LC-MS: 426 (M+H)⁺.

Compound 11

N-(3-Chloro-4-fluorophenyl)-2-(propylsulfonamido)isonicotinamide

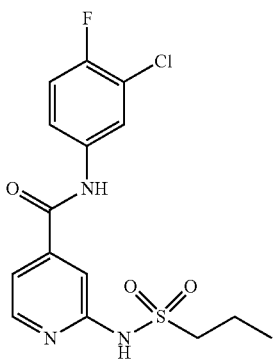 [SMILES: CCCS(=O)(=O)Nc1cc(C(=O)Nc2ccc(F)c(Cl)c2)ccn1]

The title compound was prepared in an analogous manner to Compound 8 using propane-1-sulfonyl chloride as a starting material. LC-MS: 372 (M+H)⁺.

Compound 12

N-(3-Chloro-4-fluorophenyl)-2-(cyclohexanesulfonamido)isonicotinamide

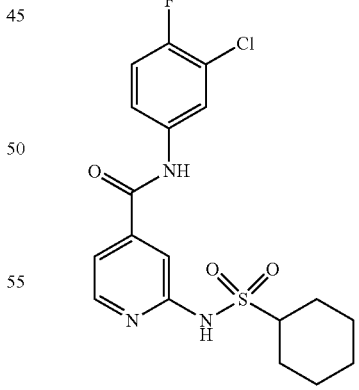

The title compound was prepared in an analogous manner to Compound 8 using cyclohexanesulfonyl chloride as a starting material. LC-MS: 412 (M+H)⁺.

Compound 13

N-(3-Chloro-4-fluorophenyl)-2-(4-methylphenylsulfonamido)isonicotinamide

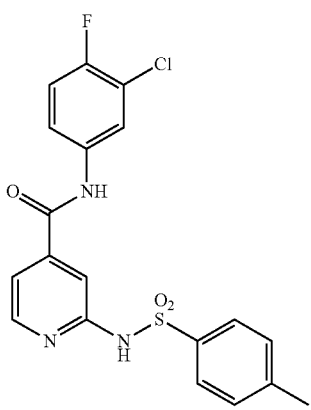 [SMILES: Cc1ccc(S(=O)(=O)Nc2cc(C(=O)Nc3ccc(F)c(Cl)c3)ccn2)cc1]

The title compound was prepared in an analogous manner to Compound 8 using p-toluenesulfonyl chloride as a starting material. LC-MS: 420 (M+H)+.

Compound 14

N-(3-Chloro-4-fluorophenyl)-2-(cyclopropanesulfonamido)-6-methylisonicotinamide

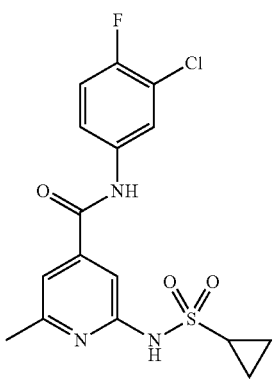 [SMILES: Cc1cc(C(=O)Nc2ccc(F)c(Cl)c2)cc(NS(=O)(=O)C2CC2)n1]

Step 1; To a solution of 4-chloro-6-methylpyridin-2-amine (0.33 g, 2.34 mmol) in anhydrous pyridine (6 mL) at 0° C. was added dimethylaminopyridine (0.029 g, 0.23 mmol) and cyclopropanesulfonyl chloride (0.41 mL, 3.97 mmol). The resulting mixture was stirred cold for 5 minutes then heated to 60° C. for 16 h. The reaction was cooled to RT and diluted with EtOAc and 1:1 1M HCl brine. The organics were washed twice with 1M HCl, brine (2×), dried over Na2SO4, filtered and concentrated in vacuo. The resulting crude material was purified on silica gel eluting with a solvent gradient of 0% to 70% EtOAc in hexanes to afford N-(4-chloro-6-methylpyridin-2-yl)cyclopropanesulfonamide.

Step 2; Combined N-(4-chloro-6-methylpyridin-2-yl)cyclopropanesulfonamide (0.18 g, 0.73 mmol), sodium carbonate (0.15 g, 1.46 mmol), 3-chloro-4-fluoroaniline (0.16 g, 1.10 mmol), toluene (10 mL), xantphos (0.018 g, 0.03 mmol), and Pd(OAc)2 (0.007 g, 0.03 mmol) in a RBF which was stirred and purged with carbon monoxide gas. The resulting mixture was stirred under a carbon monoxide atmosphere and heated to 90° C. for 16 h. The reaction was cooled to RT and diluted with EtOAc and brine. The organics were washed with water, dried over Na2SO4, filtered and concentrated in vacuo. The resulting crude material was purified on silica gel eluting with a solvent gradient of 10% to 100% EtOAc in hexanes to afford the title compound with impurities. The residue thus obtained was further purified using a preparatory TLC plate using 7% methanol in DCM as eluent to afford the title compound. LC-MS: 384 (M+H)+.

Compound 15

N-(3-Chloro-4-fluorophenyl)-2-(cyclopropanesulfonamido)-6-fluoroisonicotinamide

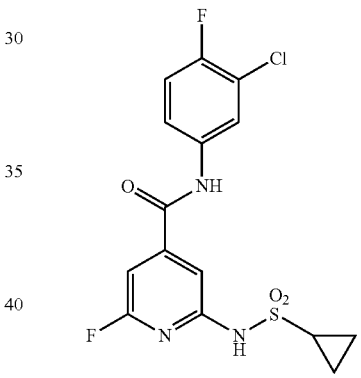

Step 1; To a solution of 2,6-difluoroisonicotinic acid (1.0 g, 6.3 mmol) in DMF (15 mL) was added HATU (2.87 g, 7.5 mmol) followed by N,N-diisopropylethylamine (3.3 mL, 18.9 mmol). After stirring at room temperature for 18 hrs, the reaction mixture was quenched with sat'd. aq. NH4Cl solution, extracted with EtOAc, washed with water, dried (MgSO4), filtered and evaporated in vacuo. The resulting material was triturated from a mixture of EtOAc and hexanes to afford a colorless solid isolated via filtration, dried in vacuo and used without further purification.

Step 2; To a solution of the isolated N-(3-chloro-4-fluorophenyl)-2,6-difluoroisonicotinamide (400 mg, 1.40 mmol) in anhydrous DMSO (5 mL) was added K2CO3 (400 mg, 2.9 mmol) in a sealable vial which was then closed and heated at 110° C. for 18 hrs. After cooling, the mixture was diluted with sat'd. aq NH4Cl solution, extracted with EtOAc, the organic phase separated, washed with water, dried (MgSO4), filtered and evaporated in vacuo. Purification via silica gel chromatography afforded the title compound as a colorless solid. LC-MS: 388 (M+H)+.

Compound 16

N-(3-Chloro-4-fluorophenyl)-2-fluoro-6-(phenylsulfonamido)isonicotinamide

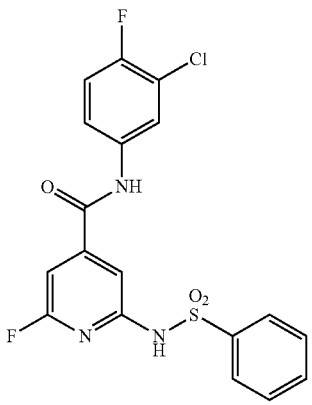 [SMILES: O=C(Nc1ccc(F)c(Cl)c1)c1cc(F)nc(NS(=O)(=O)c2ccccc2)c1]

Prepared in an analogous fashion to Compound 15 using benzenesulfonamide in step 2. LC-MS: 388 (M+H)+ 424.

Compound 17

N-(3-Chloro-4-fluorophenyl)-2-(phenylmethylsulfonamido)isonicotinamide

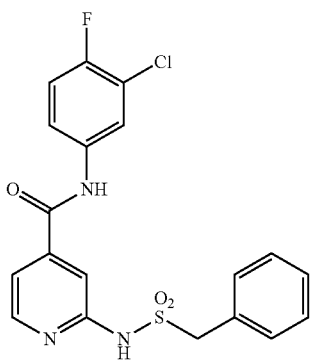 [SMILES: O=C(Nc1ccc(F)c(Cl)c1)c1ccnc(NS(=O)(=O)Cc2ccccc2)c1]

The title compound was prepared in an analogous manner to Compound 8 using phenylmethanesulfonyl chloride as a starting material. LC-MS: 420 (M+H)+.

Compound 18

N-(3-Chloro-4-fluorophenyl)-2-(2-methoxyethylsulfonamido)isonicotinamide

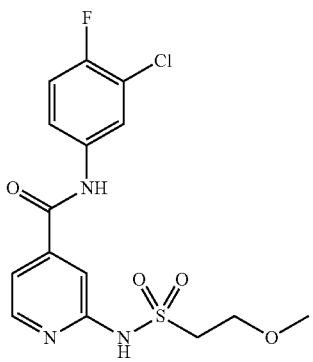 [SMILES: COCCS(=O)(=O)Nc1cc(C(=O)Nc2ccc(F)c(Cl)c2)ccn1]

To a solution of 2-amino-N-(3-chloro-4-fluorophenyl)isonicotinamide (Intermediate D) (0.15 g, 0.57 mmol) in anhydrous dioxane (5 mL) was added triethylamine (0.16 mL, 1.13 mmol) and 2-methoxyethanesulfonyl chloride (0.11 mL, 0.903 mmol). The resulting mixture was stirred and heated to 80 C for 48 h. The reaction was cooled to RT and evaporated in vacuo. The organics were washed twice with 1M HCl, brine (2×), dried over $Na_2SO_4$, filtered and concentrated in vacuo. The resulting crude material was purified on silica gel eluting with a solvent gradient of 10% to 100% EtOAc in hexanes to afford the title compound. LC-MS: 386 (M+H)+.

Compound 19

N-(3-Chloro-4-fluorophenyl)-2-(thiophene-2-sulfonamido)isonicotinamide

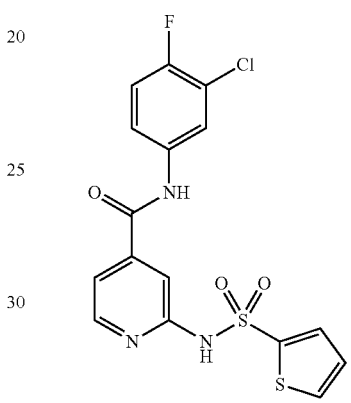

To a solution of 2-amino-N-(3-chloro-4-fluorophenyl)isonicotinamide (Intermediate D) (0.15 g, 0.57 mmol) in anhydrous pyridine (5 mL) was added thiophene-2-sulfonyl chloride (0.17 g, 0.903 mmol). The resulting mixture was stirred at RT for 16 h. The reaction was diluted with EtOAc and 1M HCl. The organics were washed twice with brine, water, coevaporated with heptanes and concentrated in vacuo. The product was crashed out of 10% MeOH/DCM. The resulting filtered solid afforded the title compound. LC-MS: 412 (M+H)+.

Compound 20

N-(3-Chloro-4-fluorophenyl)-2-(cyclohexylmethylsulfonamido)isonicotinamide

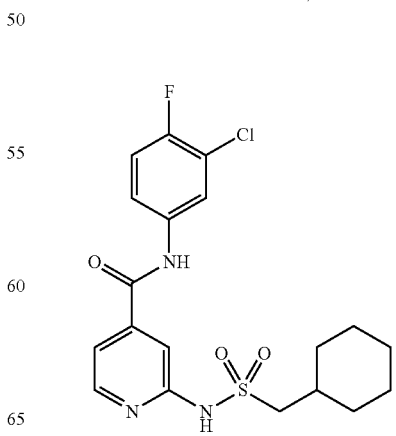

To a solution of 2-amino-N-(3-chloro-4-fluorophenyl) isonicotinamide (Intermediate D) (0.15 g, 0.57 mmol) in anhydrous pyridine (5 mL) and cyclohexylmethanesulfonyl chloride (0.13 g, 0.79 mmol). The resulting mixture was stirred at RT for 16 h. The reaction was diluted with EtOAc and 1M HCl. The organics were washed twice with brine, water, and concentrated in vacuo. The resulting crude material was purified on silica gel eluting with a solvent gradient of 10% to 100% EtOAc in hexanes to afford the title compound. LC-MS: 426 (M+H)$^+$.

Compound 21

N-(3-Chloro-4-fluorophenyl)-2-(2-phenylethylsulfonamido)isonicotinamide

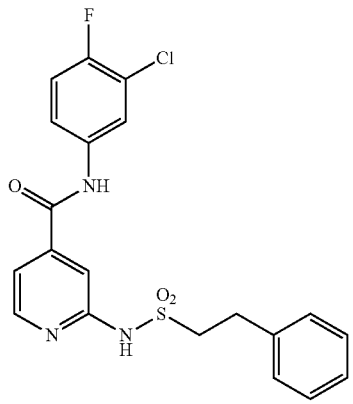 [SMILES: O=C(Nc1ccc(F)c(Cl)c1)c1ccnc(NS(=O)(=O)CCc2ccccc2)c1]

The title compound was prepared in an analogous manner to Compound 8 using 2-phenylethanesulfonyl chloride. LC-MS: 434 (M+H)$^+$.

Compound 22

N-(3-Chloro-4-fluorophenyl)-2-(cyclopropanesulfonamido)-5-fluoroisonicotinamide

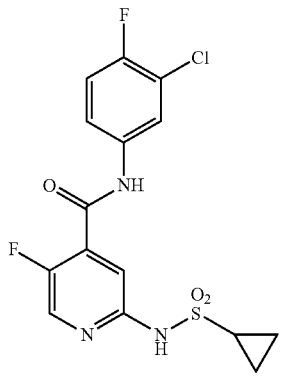 [SMILES: O=C(Nc1ccc(F)c(Cl)c1)c1cc(NS(=O)(=O)C2CC2)ncc1F]

Step 1: To a solution of 2-bromo-5-fluoroisonicotinic acid (3.0 g, 13.6 mmol) in a mixture of MeOH (10 mL) and benzene (20 mL) cooled to 0° C. was added (trimethylsilyl)diazomethane (2.0M solution in hexanes; 14 mL, 28 mmol) over a 10 minute period. After stirring at room temperature for 1.5 hrs, the solution was evaporated to dryness and the residue purified on silica gel eluting with a gradient of 0 to 40% EtOAc in hexanes to afford methyl 2-bromo-5-fluoroisonicotinate as a colorless solid.

Step 2: Cyclopropanesulfonamide (310 mg, 2.56 mmol), cesium carbonate (1.1 g, 3.38 mmol), Pd$_2$(dba)$_3$ (40 mg, 0.044 mmol), Xantphos (51 mg, 0.09 mmol) and methyl 2-bromo-5-fluoroisonicotinate (500 mg, 2.14 mmol) were mixed in a sealable vial. To this mixture was added p-dioxane (10 mL) and the suspension degassed via sub-surface sparging with nitrogen gas for 5 minutes. The vial was then sealed and heated at 100° C. for 3 hours after which point the reaction mixture turned green to red. After cooling, the solution was partitioned between water and EtOAc, the aqueous acidified with 1N HCl and extracted with EtOAc (2×). The organic phases were combined, dried (MgSO$_4$), filtered and evaporated in vacuo. $^1$H NMR analysis confirmed isolation of methyl 2-(cyclopropanesulfonamido)-5-fluoroisonicotinate as a colorless solid.

Step 3: The title compound was prepared according to the same procedure outlined for Compound 3 using the previously isolated acid and purifying the resultant amide through trituration from acetone/hexanes. LC-MS: 388 (M+H)$^+$.

Compound 23

N-(3-Chloro-4-fluorophenyl)-2-(2-cyclopropylethylsulfonamido)isonicotinamide

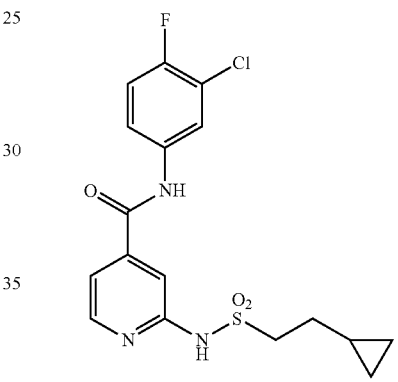

The title compound was prepared in an analogous manner to Compound 8 using 2-cyclopropylethanesulfonyl chloride as a starting material. LC-MS: 398 (M+H)$^+$.

Compound 24

N-(3-Chloro-4-fluorophenyl)-2-((1-cyanocyclopropyl)methylsulfonamido)isonicotinamide

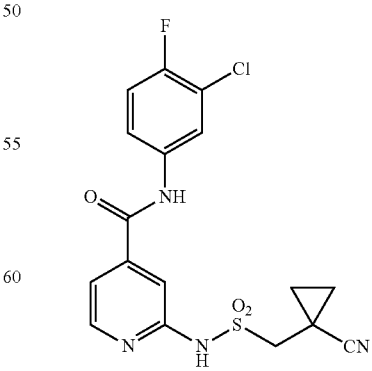

The title compound was prepared in an analogous manner to Compound 8 using (1-cyanocyclopropyl)methanesulfonyl chloride as a starting material. LC-MS: 409 (M+H)$^+$.

Compound 25

N-(3-Chloro-4-fluorophenyl)-2-(3-methylbutylsulfonamido)isonicotinamide

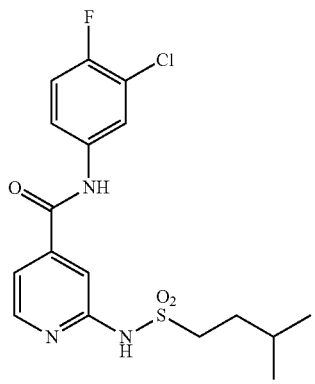 [SMILES: CC(C)CCS(=O)(=O)Nc1cc(C(=O)Nc2ccc(F)c(Cl)c2)ccn1]

The title compound was prepared in an analogous manner to Compound 8 using 3-methylbutane-1-sulfonyl chloride as a starting material. LC-MS: 400 (M+H)$^+$.

Compound 26

N-(3-Chloro-4-fluorophenyl)-2-(cyclopropanesulfonamido)-5-methoxyisonicotinamide

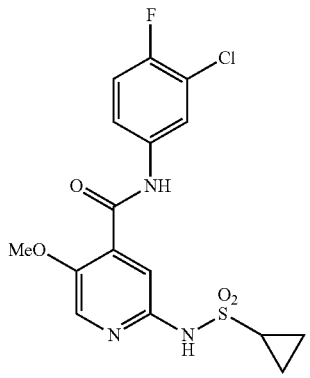 [SMILES: COc1cnc(NS(=O)(=O)C2CC2)cc1C(=O)Nc1ccc(F)c(Cl)c1]

Step 1: To a solution of the methyl ester isolated from Compound 22 Step 1 (1.0 g, 4.27 mmol) in MeOH (10 mL) was added NaOMe (25% wt solution: 5 mL). After stirring at rt for 1.5 hrs, the reaction was quenched by addition of sat'd. aq. NH$_4$Cl solution. The resulting mixture was extracted with EtOAc, the organic phase separated, dried (MgSO$_4$), filtered and evaporated in vacuo. Purification via silica gel chromatography afforded methyl 2-bromo-5-methoxyisonicotinate as a colorless solid.

Step 2: tert-Butyl carbamate (300 mg, 2.56 mmol), cesium carbonate (1.1 g, 3.38 mmol), Pd$_2$(dba)$_3$ (40 mg, 0.044 mmol), Xantphos (51 mg, 0.09 mmol) and methyl 2-bromo-5-methoxyisonicotinate (527 mg, 2.14 mmol) were mixed in a sealable vial. To this mixture was added p-dioxane (10 mL) and the suspension degassed via sub-surface sparging with nitrogen gas for 5 minutes. The vial was then sealed and heated at 100° C. for 5 hours after which point the reaction mixture turned green to red. After cooling, the solution was partitioned between water and EtOAc, the aqueous acidified with 1N HCl and extracted with EtOAc (2×). The organic phases were combined, dried (MgSO$_4$), filtered and evaporated in vacuo. Purification of the isolated residue on silica gel eluting with 0 to 40% EtOAc in hexanes afforded methyl 2-((tert-butoxycarbonyl)amino)-5-methoxyisonicotinate as a colorless solid Step 3: Methyl 2-((tert-butoxycarbonyl)amino)-5-methoxyisonicotinate (300 mg; 1.06 mmol) was dissolved in 8 mL of 4N HCl in dioxane and stirred at rt for 18 hrs. The reaction mixture was evaporated to dryness in vacuo to afford methyl 2-amino-5-methoxyisonicotinate, used without further analysis or purification.

Step 4: To a solution of the isolated methyl 2-amino-5-methoxyisonicotinate (1.06 mmol) in pyridine (4 mL) was added cyclopropanesulfonyl chloride (110 µL, 1.07 mmol) and the mixture stirred for 18 hrs. The mixture was diluted with EtOAc, washed with water, dried (MgSO$_4$), filtered and evaporated in vacuo. Purification of the residue on silica gel afforded methyl 2-(cyclopropanesulfonamido)-5-methoxyisonicotinate as a colorless solid.

Step 5: Methyl 2-(cyclopropanesulfonamido)-5-methoxyisonicotinate (190 mg, 0.66 mmol) was dissolved in a mixture of THF (3 mL) and water (1 mL) to which was added LiOH.H$_2$O (80 mg, 1.9 mmol). After stirring at rt for 12 hrs, the solution was acidified with 1N HCl, extracted with EtOAc, the organic phase separated, dried (MgSO$_4$), filtered and evaporated in vacuo. The afforded 2-(cyclopropanesulfonamido)-5-methoxyisonicotinic acid was used in the final step without further purification.

Step 6: 2-(Cyclopropanesulfonamido)-5-methoxyisonicotinic acid (80.0 mg, 0.294 mmol) was dissolved in DMF (3 mL) to which was added HATU (125.0 mg, 0.324 mmol) followed by Hünigs base (0.3 mL, 1.7 mmol). After stirring for 1 hr, 3-chloro-4-fluoroaniline (52 mg, 0.357 mmol) was added and the reaction mixture maintained at rt for 18 hrs. The solution was then diluted with EtOAc and 1N HCl, the organic phase separated, washed with water, dried (MgSO$_4$), filtered and evaporated in vacuo. The residue was triturated with a mixture of EtOAc and hexanes to afford the title compound as a colorless solid. LC-MS: 400 (M+H)$^+$.

Compound 27

5-Chloro-N-(3-chloro-4-fluorophenyl)-2-(cyclopropanesulfonamido)isonicotinamide

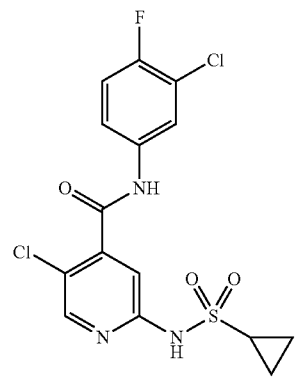 [SMILES: O=C(Nc1ccc(F)c(Cl)c1)c1cc(NS(=O)(=O)C2CC2)ncc1Cl]

Step 1; To a solution of methyl 2-amino-5-chloroisonicotinate (0.50 g, 2.68 mmol) in anhydrous pyridine (10 mL) at 0° C. was added catalytic dimethylaminopyridine and cyclopropanesulfonyl chloride (0.44 mL, 4.29 mmol). The resulting mixture was heated to 35° C. for 16 h. The reaction was cooled to RT and diluted with EtOAc and brine. The organics were washed with 1M HCl, brine, and water, coevaporated with heptanes and concentrated in vacuo. The resulting crude material was purified on C$_{18}$ column eluting with a solvent gradient of 20% to 100% acetonitrile in water to afford methyl 5-chloro-2-(cyclopropanesulfonamido) isonicotinate.

Step 2; Combined methyl 5-chloro-2-(cyclopropanesulfonamido)isonicotinate (0.23 g, 0.77 mmol), THF (6.2 mL), MeOH (6.2 mL) and 1 M LiOH (6.19 mL, 6.19 mmol) and stirred at RT for 16 h. The reaction was concentrated and diluted with EtOAc and 1M HCl. The organics were washed with water and concentrated in vacuo. The resulting crude material containing 5-chloro-2-(cyclopropanesulfonamido) isonicotinic acid was used as is in the next step.

Step 3; The title compound was prepared in an analogous manner to Intermediate A using HATU coupling conditions and 5-chloro-2-(cyclopropanesulfonamido)isonicotinic acid. LC-MS: 405 (M+H)$^+$.

Compound 28

N-(3-Chloro-4-fluorophenyl)-2-(cyclopentylmethyl-sulfonamido)isonicotinamide

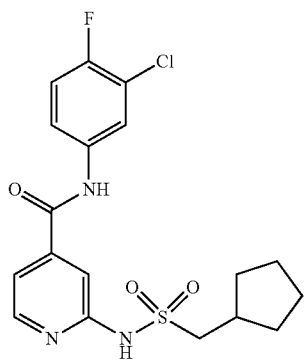 [SMILES: O=C(Nc1ccc(F)c(Cl)c1)c1ccnc(NS(=O)(=O)CC2CCCC2)c1]

The title compound was prepared in an analogous manner to Compound 8 using cyclopentylmethanesulfonyl chloride. LC-MS: 412 (M+H)$^+$.

Compound 29

N-(3-Chloro-4-fluorophenyl)-2-((4-fluorophenyl)methylsulfonamido)isonicotinamide

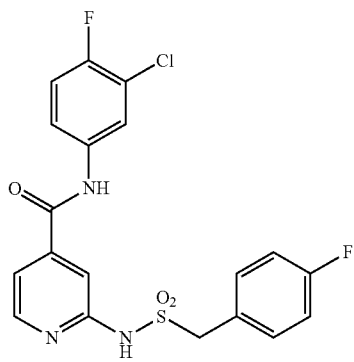 [SMILES: O=C(Nc1ccc(F)c(Cl)c1)c1ccnc(NS(=O)(=O)Cc2ccc(F)cc2)c1]

The title compound was prepared in an analogous manner to Compound 8 using (4-fluorophenyl)methanesulfonyl chloride as a starting material. LC-MS: 438 (M+H)$^+$.

Compound 30

N-(3-Chloro-4-fluorophenyl)-2-(p-tolylmethylsulfonamido)isonicotinamide

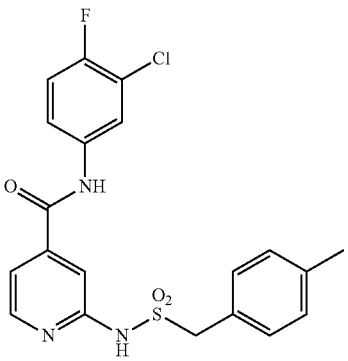 [SMILES: Cc1ccc(CS(=O)(=O)Nc2cc(C(=O)Nc3ccc(F)c(Cl)c3)ccn2)cc1]

The title compound was prepared in an analogous manner to Compound 8 using (p-tolylmethanesulfonyl chloride as a starting material. LC-MS: 434 (M+H)$^+$.

Compound 31

N-(3,4-Difluorophenyl)-2-((4-fluorophenyl)methyl-sulfonamido)isonicotinamide

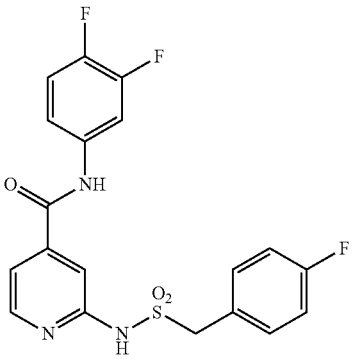 [SMILES: O=C(Nc1ccc(F)c(F)c1)c1ccnc(NS(=O)(=O)Cc2ccc(F)cc2)c1]

The title compound was prepared in an analogous manner to Compound 8 using (p-tolylmethanesulfonyl chloride and Intermediate D as a starting material. LC-MS: 434 (M+H)$^+$.

Compound 32

N-(3-Chloro-4-fluorophenyl)-2-(1,1-dimethylethyl-sulfonamido)isonicotinamide

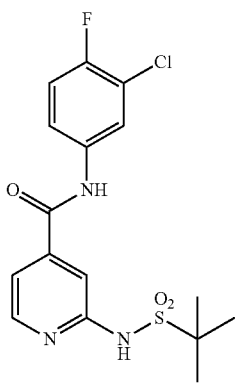

The title compound was prepared in an analogous manner to Compound 2 using 2-methylpropane-2-sulfonamide as a starting material. LC-MS: 386 (M+H)$^+$.

Compound 33

N-(3-Chloro-4-fluorophenyl)-2-((1-hydroxycyclobu-tyl)methylsulfonamido) isonicotinamide

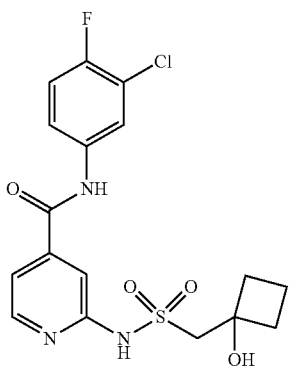 [SMILES: O=C(Nc1ccc(F)c(Cl)c1)c1ccnc(NS(=O)(=O)CC2(O)CCC2)c1]

Step 1; To a solution of benzylamine (4.00 g, 37.33 mmol) in DCM (50 mL) at 0° C. was added methanesulfonyl chloride (1.44 mL, 18.66 mmol) dropwise. The resulting mixture was stirred cold for 10 minutes then diluted with water. The organics were washed with water, 1M HCl, dried over Na$_2$SO$_4$, filtered and concentrated in vacuo. The resulting crude material containing N-benzylmethanesulfonamide was used as is in the next step.

Step 2; To a solution of N-benzylmethanesulfonamide (1.00 g, 5.39 mmol) in anhydrous THF (10 mL) at −78° C. under a nitrogen atmosphere was added nBuLi (2.5M in hexanes, 4.32 mL, 10.78 mmol) dropwise. After 5 minutes of stirring at −78° C., cyclobutanone (1.92 mL, 21.56) was added dropwise. The resulting solution was stirred at −78° C. for 2 h, RT 1 hr, and quenched with 1 mL of acetic acid. The reaction was evaporated and the residue was diluted with EtOAc and a saturated solution of NaHCO$_3$. The organics were washed once more with a saturated solution of NaHCO$_3$, brine, and water, and concentrated in vacuo. The resulting crude material was purified on silica gel eluting with a solvent gradient of 0% to 9% MeOH in DCM to afford N-benzyl-1-(1-hydroxycyclobutyl)methanesulfonamide which was contaminated with impurities. The resulting solid was triturated in 1:1 EtOAc/heptanes and filtered to obtain pure material.

Step 3; Combined N-benzyl-1-(1-hydroxycyclobutyl)methanesulfonamide (0.34 g, 1.33 mmol), Pd(OH)$_2$ (70 mg, 20% wt/wt), MeOH (6.2 mL) and stirred under a hydrogen atmosphere at 60° C. for 16 h. The reaction was filtered through a pad of celite and concentrated in vacuo to obtain (1-hydroxycyclobutyl)methanesulfonamide which was used as is in the next step.

Step 4; The title compound was prepared in an analogous manner to Compound 2 using (1-hydroxycyclobutyl)methanesulfonamide and CuI coupling conditions. LC-MS: 414 (M+H)$^+$.

Compound 34

N-(3-Chloro-4-fluorophenyl)-2-(2-hydroxy-2-methylpropylsulfonamido) isonicotinamide

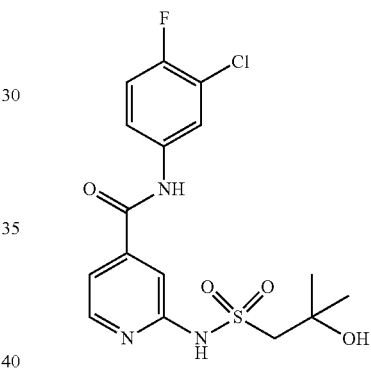

The title compound was prepared in an analogous manner to compound 33 using acetone in step 2. LC-MS: 402 (M+H)$^+$.

Compound 35

N-(3-Chloro-4-fluorophenyl)-2-(methylsulfonamido) isonicotinamide

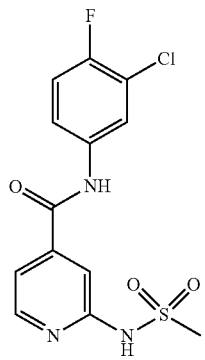 [SMILES: CS(=O)(=O)Nc1cc(C(=O)Nc2ccc(F)c(Cl)c2)ccn1]

The title compound was prepared in an analogous manner to Compound 2 using methanesulfonamide and CuI coupling conditions. LC-MS: 402 (M+H)+.

Compound 36

N-(3-Chloro-4-fluorophenyl)-2-(cyclopropylmethyl-sulfonamido)isonicotinamide

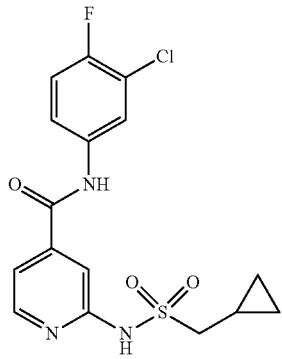 [SMILES: O=C(Nc1ccc(F)c(Cl)c1)c1ccnc(NS(=O)(=O)CC2CC2)c1]

The title compound was prepared in an analogous manner to Compound 8 using cyclopropylmethanesulfonyl chloride. LC-MS: 384 (M+H)+.

Compound 37

N-(3-Chloro-4-fluorophenyl)-2-((3-methyloxetan-3-yl)methylsulfonamido) isonicotinamide

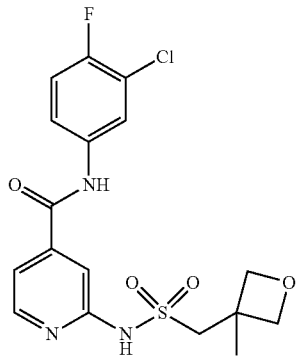 [SMILES: CC1(CS(=O)(=O)Nc2cc(C(=O)Nc3ccc(F)c(Cl)c3)ccn2)COC1]

The title compound was prepared in an analogous manner to Compound 8 using (3-methyloxetan-3-yl)methanesulfonyl chloride. LC-MS: 414 (M+H)+.

Compound 38

N-(3-Chloro-4-fluorophenyl)-2-(tetrahydro-2H-pyran-4-sulfonamido)isonicotinamide

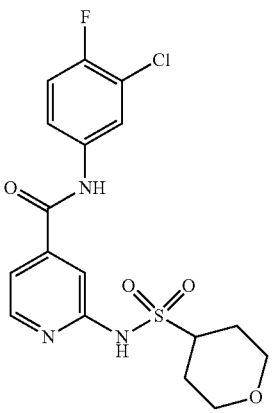 [SMILES: O=C(Nc1ccc(F)c(Cl)c1)c1ccnc(NS(=O)(=O)C2CCOCC2)c1]

The title compound was prepared in an analogous manner to Compound 8 using tetrahydro-2H-pyran-4-sulfonyl chloride. LC-MS: 414 (M+H)+.

Compound 39

(±)-N-(3-Chloro-4-fluorophenyl)-2-(tetrahydrofuran-3-sulfonamido)isonicotinamide

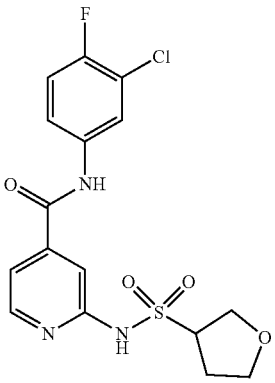 [SMILES: O=C(Nc1ccc(F)c(Cl)c1)c1ccnc(NS(=O)(=O)C2CCOC2)c1]

The title compound was prepared in an analogous manner to Compound 8 using tetrahydrofuran-3-sulfonyl chloride. LC-MS: 400 (M+H)+.

Compound 40

(±)-N-(3-Chloro-4-fluorophenyl)-2-(3-hydroxy-2-methylpropylsulfonamido)isonicotinamide

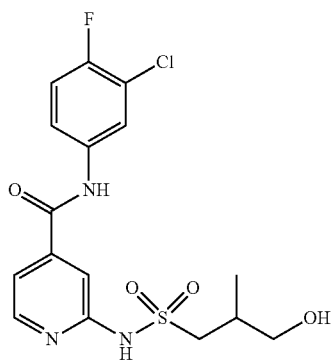 [SMILES: CC(CO)CS(=O)(=O)Nc1cc(C(=O)Nc2ccc(F)c(Cl)c2)ccn1]

The title compound was prepared in an analogous manner to Compound 8 using methyl 3-(chlorosulfonyl)-2-methylpropanoate followed by LiBH$_4$ reduction. LC-MS: 402 (M+H)$^+$.

Compound 41

N-(3-Chloro-4-fluorophenyl)-2-(1-methylethylsulfonamido)isonicotinamide

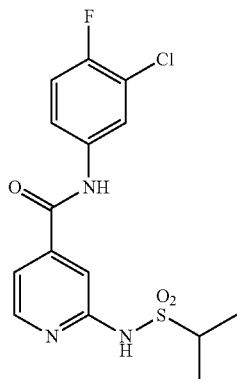

The title compound was prepared in an analogous manner to Compound 2 using propane-2-sulfonamide as a starting material. LC-MS: 372 (M+H)$^+$.

Compound 42

N-(3-Chloro-4-fluorophenyl)-2-(2,2-dimethylpropylsulfonamido)isonicotinamide

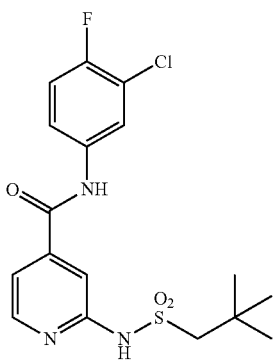

The title compound was prepared in an analogous manner to Compound 2 using 2,2-dimethylpropane-1-sulfonamide as a starting material. LC-MS: 400 (M+H)$^+$.

Compound 43

N-(3,4-Difluorophenyl)-2-(1-methylethylsulfonamido)isonicotinamide

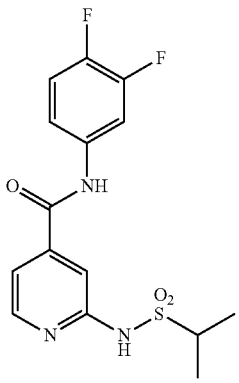 [SMILES: CC(C)S(=O)(=O)Nc1cc(C(=O)Nc2ccc(F)c(Cl)c2)ccn1]

The title compound was prepared in an analogous manner to Compound 2 using propane-2-sulfonamide and Intermediate C as starting materials. LC-MS: 356 (M+H)$^+$.

Compound 44

N-(3,4-Difluorophenyl)-2-(tetrahydro-2H-pyran-4-sulfonamido)isonicotinamide

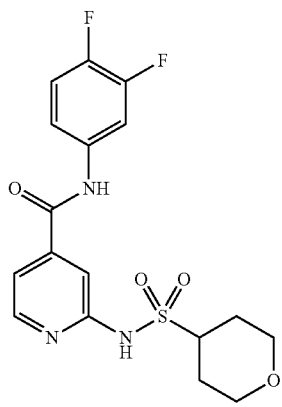 [SMILES: O=C(Nc1ccc(F)c(F)c1)c1ccnc(NS(=O)(=O)C2CCOCC2)c1]

The title compound was prepared in an analogous manner to Compound 8 using tetrahydro-2H-pyran-4-sulfonyl chloride and Intermediate G. LC-MS: 398 (M+H)+.

Compound 45

(±)-N-(3,4-Difluorophenyl)-2-(tetrahydrofuran-3-sulfonamido)isonicotinamide

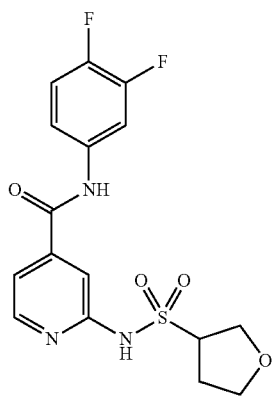 [SMILES: O=C(Nc1ccc(F)c(F)c1)c1ccnc(NS(=O)(=O)C2CCOC2)c1]

The title compound was prepared in an analogous manner to Compound 8 using tetrahydrofuran-3-sulfonyl chloride and Intermediate G. LC-MS: 384 (M+H)+

Compound 46

(±)-N-(3-Chloro-4-fluorophenyl)-2-((tetrahydrofuran-2-yl)methylsulfonamido)isonicotinamide

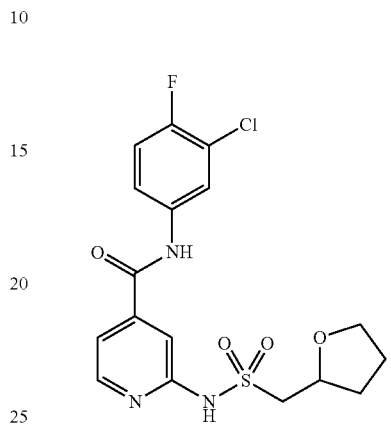

The title compound was prepared in an analogous manner to Compound 8 using (tetrahydrofuran-2-yl)methanesulfonyl chloride. LC-MS: 414 (M+H)+.

Compound 47

(±)-N-(3-Chloro-4-fluorophenyl)-2-((tetrahydro-2H-pyran-2-yl)methylsulfonamido)isonicotinamide

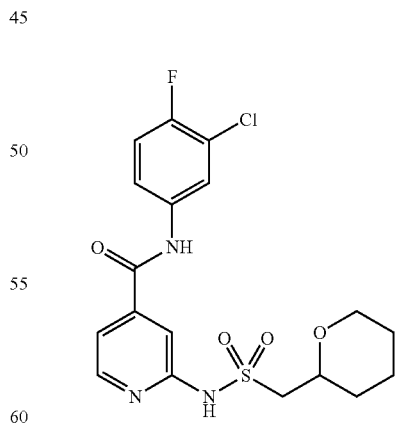

The title compound was prepared in an analogous manner to Compound 8 using (tetrahydro-2H-pyran-2-yl)methanesulfonyl chloride. LC-MS: 428 (M+H)+.

Compound 48

(±)-N-(3-Chloro-4-fluorophenyl)-2-((tetrahydro-2H-pyran-3-yl)methylsulfonamido)isonicotinamide

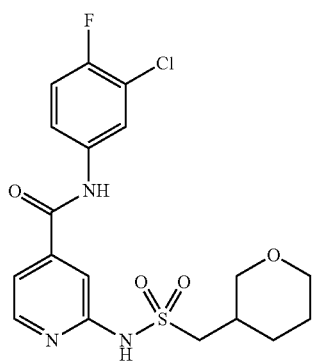

The title compound was prepared in an analogous manner to Compound 2 using (tetrahydro-2H-pyran-3-yl)methanesulfonamide. LC-MS: 428 (M+H)$^+$.

Compound 49

(cis/trans)-N-(3-Chloro-4-fluorophenyl)-2-(4-hydroxycyclohexanesulfonamido)isonicotinamide

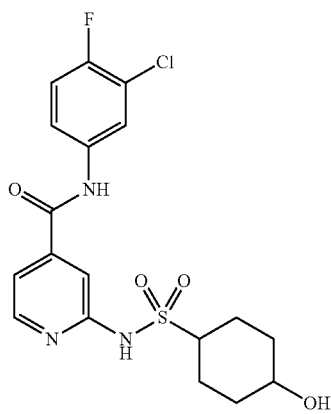 [SMILES: O=C(Nc1ccc(F)c(Cl)c1)c1ccnc(NS(=O)(=O)C2CCC(O)CC2)c1]

Step 1; To a RBF in a 0° C. ice bath was added sodium chlorite (1.03 g, 11.34 mmol) and anhydrous acetonitrile (10 mL) followed by concentrated HCl (2.27 mL) dropwise. To the cold stirring mixture was added 4-mercaptocyclohexanol (0.50 g, 3.78 mmol, dissolved in 3 mL of acetonitrile) dropwise. The ice bath was removed and the resulting mixture was stirred at RT for 2 h then diluted with EtOAc and water. The organics were washed sequentially with water, brine, dried over Na$_2$SO$_4$, filtered and concentrated in vacuo. The resulting crude oil containing 4-hydroxycyclohexane-1-sulfonyl chloride was used as is in the next step.

Step 2; 4-hydroxycyclohexane-1-sulfonyl chloride (0.70 g, crude) was dissolved in DCM (15 mL) and stirred at −78° C. To the cold stirring mixture was condensed liquid ammonia (15 mL) and the resulting mixture was stirred at −78° C. for 2 h, refluxed at 0° C. for 2 h, then allowed to warm to rt for 16 h. The solvents were evaporated in vacuo and the resulting crude solid containing 4-hydroxycyclohexane-1-sulfonamide was used as is in the next step.

Step 3; The title compound was prepared in an analogous manner to Compound 2 using 4-hydroxycyclohexane-1-sulfonamide and CuI coupling conditions. LC-MS: 428 (M+H)$^+$.

Compound 50

N-(3-Chloro-4-fluorophenyl)-2-(2-(pyridin-2-yl)ethylsulfonamido)isonicotinamide

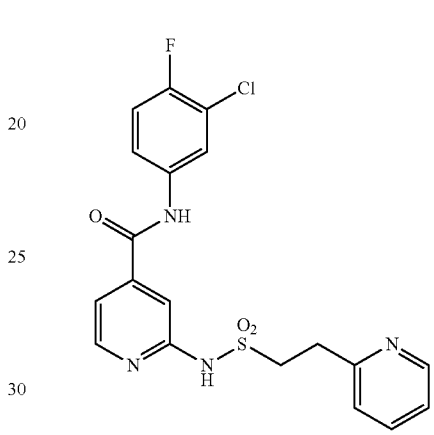

The title compound was prepared in an analogous manner to Compound 8 using 2-(pyridin-2-yl)ethanesulfonyl chloride hydrochloride as starting material. LC-MS: 428 (M+H)$^+$.

Compound 51

N-(3-Chloro-4-fluorophenyl)-2-(2-(4-methoxyphenyl)ethylsulfonamido)isonicotinamide

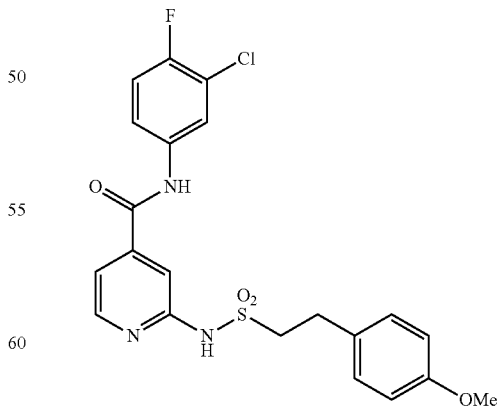

The title compound was prepared in an analogous manner to Compound 8 using 2-(4-methoxyphenyl)ethanesulfonyl chloride as starting material. LC-MS: 464 (M+H)$^+$.

Compound 52

N-(3,4-Difluorophenyl)-2-(2-(pyridin-2-yl)ethylsulfonamido)isonicotinamide

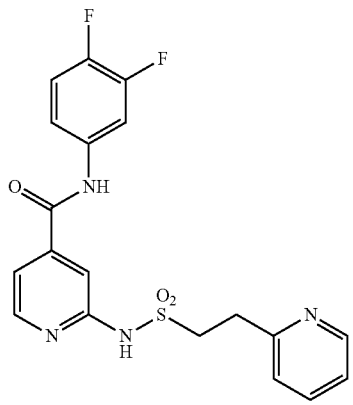 [SMILES: O=C(Nc1ccc(F)c(F)c1)c1ccnc(NS(=O)(=O)CCc2ccccn2)c1]

The title compound was prepared in an analogous manner to Compound 8 using 2-(pyridin-2-yl)ethanesulfonyl chloride hydrochloride and Intermediate E as starting materials. LC-MS: 419 (M+H)$^+$.

Compound 53

N-(3,4-Difluorophenyl)-2-(2-(4-methoxyphenyl)ethylsulfonamido)isonicotinamide

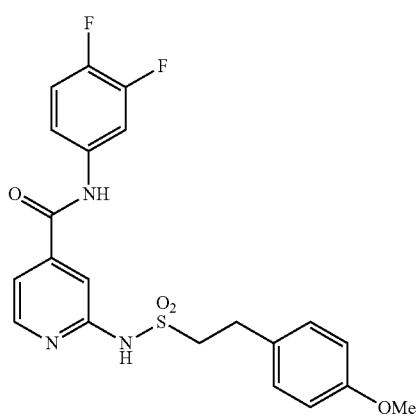 [SMILES: COc1ccc(CCS(=O)(=O)Nc2cc(C(=O)Nc3ccc(F)c(F)c3)ccn2)cc1]

The title compound was prepared in an analogous manner to Compound 8 using 2-(4-methoxyphenyl)ethanesulfonyl chloride and Intermediate E as starting materials. LC-MS: 448 (M+H)$^+$.

Compound 54

N-(3-Chloro-4-fluorophenyl)-2-((4-cyanophenyl)methylsulfonamido)isonicotinamide

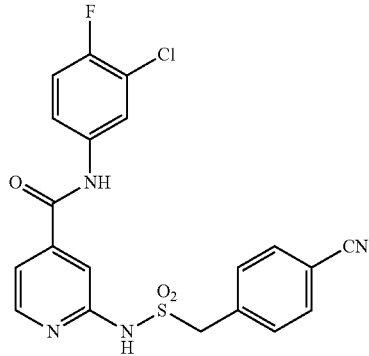 [SMILES: N#Cc1ccc(CS(=O)(=O)Nc2cc(C(=O)Nc3ccc(F)c(Cl)c3)ccn2)cc1]

The title compound was prepared in an analogous manner to Compound 8 using (4-cyanophenyl)methanesulfonyl chloride as starting material. LC-MS: 445 (M+H)$^+$.

Compound 55

2-((4-Cyanophenyl)methylsulfonamido)-N-(3,4-difluorophenyl)isonicotinamide

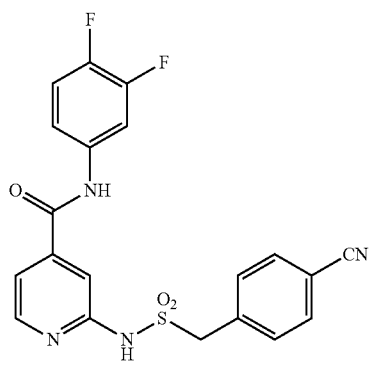 [SMILES: N#Cc1ccc(CS(=O)(=O)Nc2cc(C(=O)Nc3ccc(F)c(F)c3)ccn2)cc1]

The title compound was prepared in an analogous manner to Compound 8 using (4-cyanophenyl)methanesulfonyl chloride and Intermediate E as starting materials. LC-MS: 429 (M+H)$^+$.

Compound 56

N-(3-Chloro-4-fluorophenyl)-2-((tetrahydro-2H-pyran-4-yl)methylsulfonamido)isonicotinamide

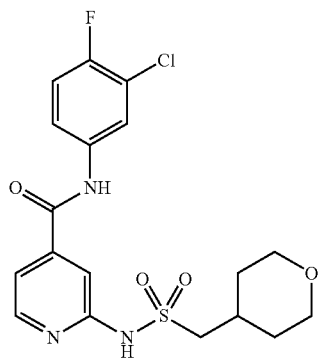 [SMILES: O=C(Nc1ccc(F)c(Cl)c1)c1ccnc(NS(=O)(=O)CC2CCOCC2)c1]

The title compound was prepared in an analogous manner to Compound 2 using (tetrahydro-2H-pyran-4-yl)methanesulfonyamide. LC-MS: 428 (M+H)⁺.

Compound 57

(±)-N-(3-Chloro-4-fluorophenyl)-2-(tetrahydro-2H-pyran-3-sulfonamido)isonicotinamide

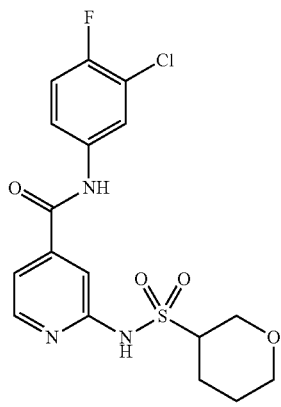 [SMILES: O=C(Nc1ccc(F)c(Cl)c1)c1ccnc(NS(=O)(=O)C2CCCOC2)c1]

The title compound was prepared in an analogous manner to Compound 2 using tetrahydro-2H-pyran-3-sulfonamide. LC-MS: 414 (M+H)⁺.

Compound 58

N-(3-Chloro-4-fluorophenyl)-2-((4-ethylphenyl)methylsulfonamido)isonicotinamide

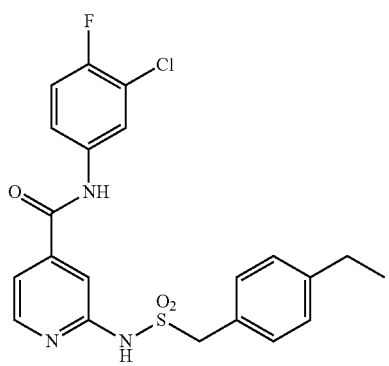 [SMILES: CCc1ccc(CS(=O)(=O)Nc2cc(C(=O)Nc3ccc(F)c(Cl)c3)ccn2)cc1]

The title compound was prepared in an analogous manner to Compound 2 using (4-ethylphenyl)methanesulfonamide. LC-MS: 448 (M+H)⁺.

Compound 59

N-(3,4-Difluorophenyl)-2-((4-ethylphenyl)methylsulfonamido)isonicotinamide

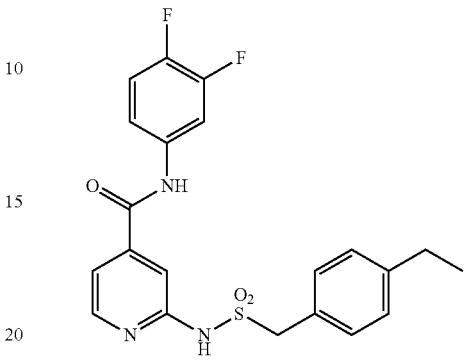

The title compound was prepared in an analogous manner to Compound 2 using (4-ethylphenyl)methanesulfonamide and Intermediate C. LC-MS: 432 (M+H)⁺.

Compound 60

(±)-N-(3-Chloro-4-fluorophenyl)-2-(3-hydroxycyclohexanesulfonamido)isonicotinamide

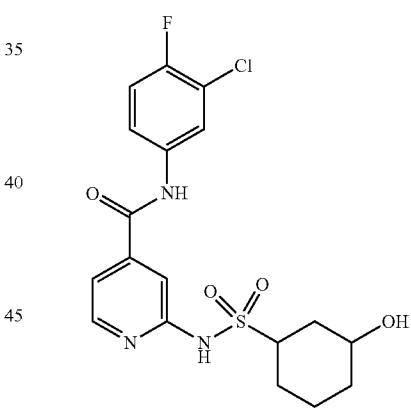

Step 1; To a solution of cyclohex-2-enone (2.00 g, 20.81 mmol) in DCE (100 mL) at RT was added indium chloride (0.23 g, 1.04 mmol) and thioacetic acid (2.38 mL, 31.21 mmol). The resulting mixture was stirred at 60° C. for 16 h then diluted with EtOAc and brine. The organics were washed with water, brine, dried over Na₂SO₄, filtered, and concentrated in vacuo. The resulting crude material was purified on silica gel eluting with a solvent gradient of 0% to 40% EtOAc in hexanes to afford pure S-(3-oxocyclohexyl)ethanethioate as an oil.

Step 2; To a solution of S-(3-oxocyclohexyl)ethanethioate (1.00 g, 5.81 mmol) in MeOH (50 mL) at 0° C. was added NaBH₄ (0.27 g, 6.97 mmol) The resulting mixture was stirred at 0° C. for 1.5 h then diluted with EtOAc and water after reducing the volume of MeOH with a stream of nitrogen gas. The organics were washed with water twice and concentrated in vacuo. The resulting crude material containing S-(3-hydroxycyclohexyl) ethanethioate was carried on as is into the next step.

Step 3; Combined S-(3-hydroxycyclohexyl)ethanethioate (0.36 g, 2.07 mmol), THF (7.5 mL), MeOH (7.5 mL), water (4.2 mL), and 5 M NaOH (3.31 mL, 16.53 mmol) and stirred at RT for 48 h. The reaction was quenched with a 20% aq. solution of citric acid monohydrate, the organics were partially evaporated, and remaining solution was diluted with EtOAc and brine. The organics were washed twice with water and concentrated in vacuo. The resulting crude was coevaporated with EtOAc to afford 3-mercaptocyclohexanol as an oil and was used as is in the next step.

Step 4; To a RBF in a 0° C. ice bath was added sodium chlorite (0.67 g, 7.37 mmol) and anhydrous acetonitrile (10 mL) followed by concentrated HCl (1.50 mL) dropwise. To the cold stirring mixture was added 3-mercaptocyclohexanol (0.33 g, 2.46 mmol, dissolved in 3 mL of acetonitrile) dropwise. The ice bath was removed and the resulting mixture was stirred at RT for 2 h then diluted with EtOAc and water. The organics were washed sequentially with water, brine, dried over $Na_2SO_4$, filtered and concentrated in vacuo. The resulting scentless crude oil containing 3-hydroxycyclohexane-1-sulfonyl chloride was used as is in the next step.

Step 5; 3-Hydroxycyclohexane-1-sulfonyl chloride (~0.40 g, crude) was dissolved in DCM (10 mL) and stirred at −78° C. To the cold stirring mixture was condensed liquid ammonia (10 mL) and the resulting mixture was stirred at −78° C. for 2 h, refluxed at 0° C. for 2 h, then allowed to warm to rt for 16 h. The solvents were evaporated in vacuo, coevaporated with 1:1 MeOH/EtOAc, and the resulting crude solid containing 3-hydroxycyclohexane-1-sulfonamide was used as is in the next step.

Step 6; The title compound was prepared in an analogous manner to Compound 2 using 3-hydroxycyclohexane-1-sulfonamide and CuI coupling conditions. LC-MS: 428 $(M+H)^+$.

Compound 61

(±)-N-(3-Chloro-4-fluorophenyl)-2-(3-hydroxycycloheptanesulfonamido)isonicotinamide

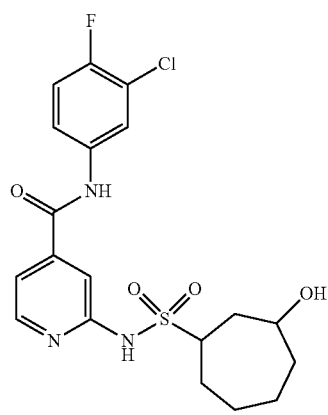 [SMILES: O=C(Nc1ccc(F)c(Cl)c1)c1ccnc(NS(=O)(=O)C2CCCCC(O)C2)c1]

The title compound was prepared in an analogous manner to Compound 61 using cyclohept-2-enone in step 1. LC-MS: 442 $(M+H)^+$.

Compound 62

2-(1-Benzylcyclopropanesulfonamido)-N-(3-chloro-4-fluorophenyl)isonicotinamide

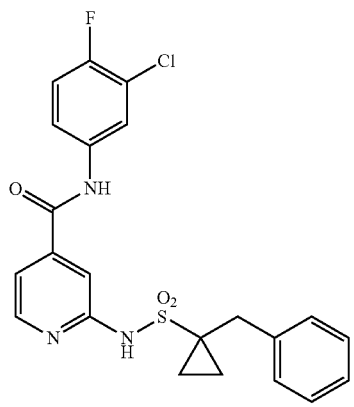 [SMILES: O=C(Nc1ccc(F)c(Cl)c1)c1ccnc(NS(=O)(=O)C2(Cc3ccccc3)CC2)c1]

Step 1: To a solution of tert-butylamine (29.6 mL, 0.282 mol) in anhydrous THF (250 mL), cooled to −20° C. was added 3-chloropropylsulfonylchloride (25 g, 0.141 mol) over a period of 10 minutes. The reaction mixture was stirred vigorously at room temperature for 16 hrs after which it was filtered under vacuum. Concentration of the filtrate afforded a colorless oil which was dissolved in DCM, washed sequentially with 1N HCl then water, the organic phase dried ($MgSO_4$), filtered and evaporated in vacuo. The resulting solid was triturated from a DCM/Hexanes mixture to afford N-(tert-butyl)-3-chloropropane-1-sulfonamide as a colorless solid after filtration and drying in vacuo.

Step 2: To a solution of N-(tert-butyl)-3-chloropropane-1-sulfonamide (2.5 g, 11.7 mmol) in anhydrous THF (100 mL) cooled to −78° C. was added n-butyllithium (2.5M in hexanes; 10 mL, 25.0 mmol). The resulting solution was allowed to warm to room temperature, stirred for 1.5 hrs then re-cooled to −78° C. after which a further addition of n-butyllithium (2.5M in hexanes; 5 mL, 12.5 mmol) was made. After further warming to room temperature, the solution was re-cooled to −78° C. and benzyl bromide (1.5 mL, 12.6 mmol) added. The final solution was stirred at room temperature for 12 hrs after which sat'd. aq. $NH_4Cl$ solution was added and the resulting mixture extracted with EtOAc (2×), the organic phases dried ($MgSO_4$), filtered and evaporated in vacuo. Trituration of the residue with hexanes and filtration afforded 1-benzyl-N-(tert-butyl)cyclopropane-1-sulfonamide as a colorless solid.

Step 3: To 1-benzyl-N-(tert-butyl)cyclopropane-1-sulfonamide (2.0 g, 7.5 mmol) was added trifluoroacetic acid (30 mL). After stirring at room temperature for 16 hrs, the reaction mixture was evaporated to dryness and the resulting solid triturated from a minimum of EtOAc/hexane mixture to afford 1-benzylcyclopropane-1-sulfonamide as a colorless solid.

Step 4: The title compound was prepared in an analogous manner to Compound 2 using the prepared 1-benzylcyclopropane-1-sulfonamide. LC-MS: 460 $(M+H)^+$.

87

Compound 63

2-(1-Benzylcyclopropanesulfonamido)-N-(3,4-difluorophenyl)isonicotinamide

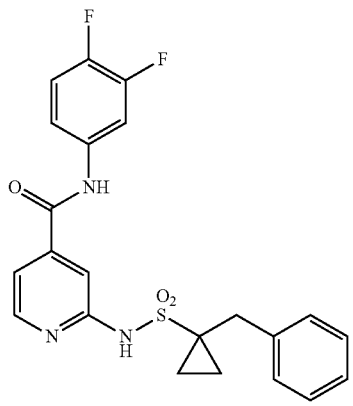 [SMILES: O=C(Nc1ccc(F)c(F)c1)c1ccnc(NS(=O)(=O)C2(Cc3ccccc3)CC2)c1]

The title compound was prepared in an analogous manner to Compound 2 using the prepared 1-benzylcyclopropane-1-sulfonamide and Intermediate C. LC-MS: 444 (M+H)$^+$.

Compound 64

(±)-N-(3-Chloro-4-fluorophenyl)-2-(3-hydroxycyclopentanesulfonamido)isonicotinamide

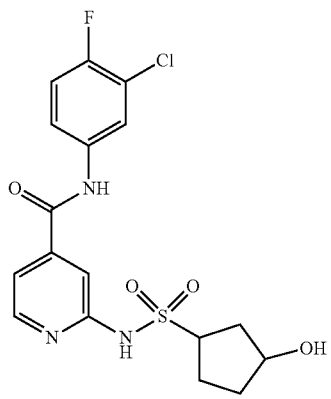 [SMILES: O=C(Nc1ccc(F)c(Cl)c1)c1ccnc(NS(=O)(=O)C2CCC(O)C2)c1]

The title compound was prepared in an analogous manner to Compound 61 using cyclopent-2-enone in step 1. LC-MS: 414 (M+H)$^+$.

88

Compound 65

3-(N-(4-((3-Chloro-4-fluorophenyl)carbamoyl)pyridin-2-yl)sulfamoyl)benzoic acid

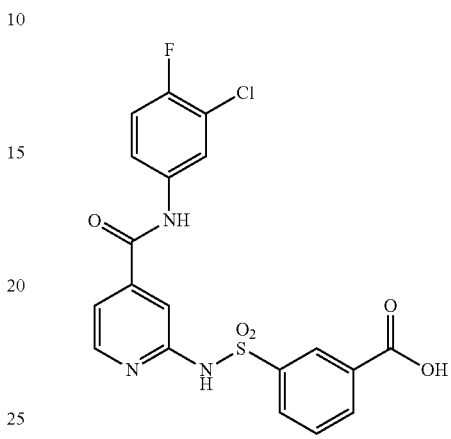

The title compound was prepared in an analogous manner to Compound 8 using (4-cyanophenyl)methanesulfonyl chloride as starting material and then standard ester hydrolysis conditions to afford the acid. LC-MS: 448 (M−H)$^-$.

Compound 66

N-(3-Chloro-4-fluorophenyl)-2-((4-isopropylphenyl)methylsulfonamido)isonicotinamide

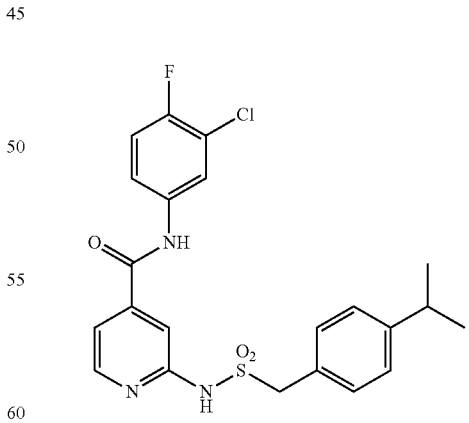

The title compound was prepared in an analogous manner to Compound 2 using (4-isopropylphenyl)methanesulfonamide. LC-MS: 462 (M+H)$^+$.

Compound 67

N-(3,4-Difluorophenyl)-2-((4-isopropylphenyl)methylsulfonamido)isonicotinamide

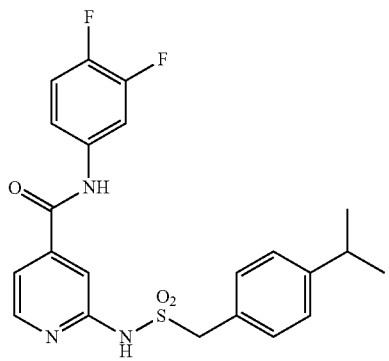

The title compound was prepared in an analogous manner to Compound 2 using (4-isopropylphenyl)methanesulfonamide and Intermediate C as starting materials. LC-MS: 446 (M+H)$^+$.

Compound 68

N-(3-Chloro-4-fluorophenyl)-2-(naphthalen-2-ylmethylsulfonamido)isonicotinamide

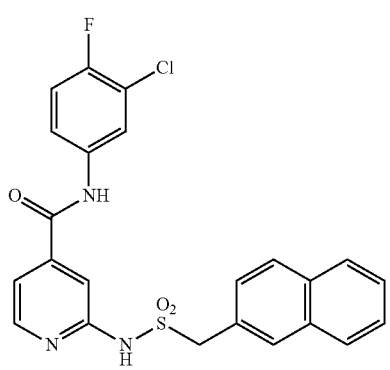 [SMILES: O=C(Nc1ccc(F)c(Cl)c1)c1ccnc(NS(=O)(=O)Cc2ccc3ccccc3c2)c1]

The title compound was prepared in an analogous manner to Compound 8 using naphthalen-2-ylmethanesulfonyl chloride as starting material. LC-MS: 470 (M+H)$^+$.

Compound 69

N-(3,4-Difluorophenyl)-2-(naphthalen-2-ylmethylsulfonamido)isonicotinamide

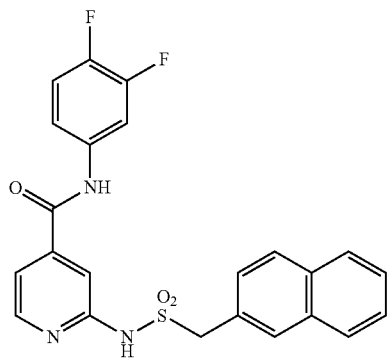 [SMILES: O=C(Nc1ccc(F)c(F)c1)c1ccnc(NS(=O)(=O)Cc2ccc3ccccc3c2)c1]

The title compound was prepared in an analogous manner to Compound 8 using naphthalen-2-ylmethanesulfonyl chloride and Intermediate E as starting materials. LC-MS: 470 (M+H)$^+$.

Compound 70

N-(3-Chloro-4-fluorophenyl)-2-((4-chlorophenyl)methylsulfonamido)isonicotinamide The title compound was prepared in an analogous manner to Compound 8 using (4-chlorophenyl)methanesulfonyl chloride as starting material. LC-MS: 454 (M+H)$^+$.

Compound 71

2-((4-Chlorophenyl)methylsulfonamido)-N-(3,4-difluorophenyl)isonicotinamide

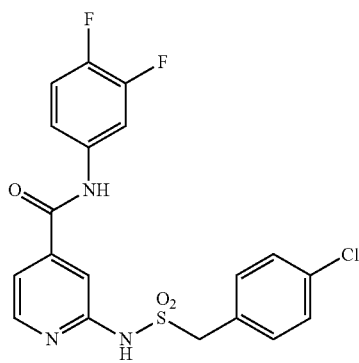 [SMILES: O=C(Nc1ccc(F)c(F)c1)c1ccnc(NS(=O)(=O)Cc2ccc(Cl)cc2)c1]

The title compound was prepared in an analogous manner to Compound 8 using (4-chlorophenyl)methanesulfonyl chloride and Intermediate E as starting materials. LC-MS: 438 (M+H)$^+$.

Compound 72

2-((4-(tert-Butyl)phenyl)methylsulfonamido)-N-(3-chloro-4-fluorophenyl)isonicotinamide

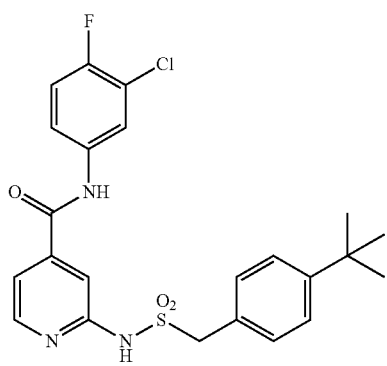 [SMILES: CC(C)(C)c1ccc(CS(=O)(=O)Nc2cc(C(=O)Nc3ccc(F)c(Cl)c3)ccn2)cc1]

Step 1: To a solution of 1-(tert-butyl)-4-(chloromethyl) benzene (1.0 g, 5.47 mmol) in DMSO (10 mL) was added sodium 3-methoxy-3-oxopropane-1-sulfinate (see Baskin, J. M.; Wang, Z. *Tet. Lett.* 2002, 43, 8479; 1.14 g, 6.55 mmol) and stirred vigorously for 18 hrs. NaOMe (25% wt; 1.5 mL) was added and after stirring for 30 min, the solution was cooled in an ice bath and a premixed solution of hydroxylamine-O-sulfonic acid (3.1 g, 27.4 mmol), NaOAc (1.7 g, 20.7 mmol) in water (25 mL) was added. The resulting solution was stirred at room temperature for 18 hrs after which it was extracted with EtOAc, the organic phase separated, dried (MgSO$_4$), filtered and evaporated in vacuo. The residue was then purified using silica gel chromatography to afford (4-(tert-butyl)phenyl)methanesulfonamide as a colorless solid.

Step 2: The title compound was prepared in an analogous manner to Compound 2 using (4-(tert-butyl)phenyl)methanesulfonamide as starting material. LC-MS: 476 (M+H)$^+$.

Compound 73

2-((4-(tert-Butyl)phenyl)methylsulfonamido)-N-(3,4-difluorophenyl)isonicotinamide

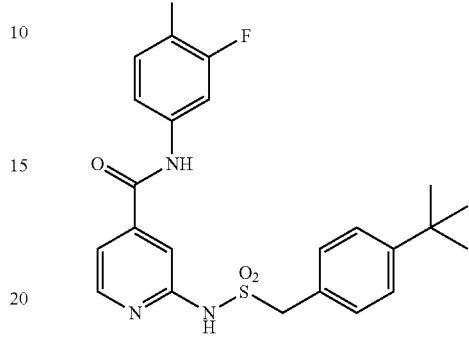

The title compound was prepared in an analogous manner to Compound 2 using (4-(tert-butyl)phenyl)methanesulfonamide and Intermediate C as starting materials. LC-MS: 460 (M+H)$^+$.

Compound 74

N-(3-Chloro-4-fluorophenyl)-2-((4-(2-hydroxypropan-2-yl)phenyl)methylsulfonamido)isonicotinamide

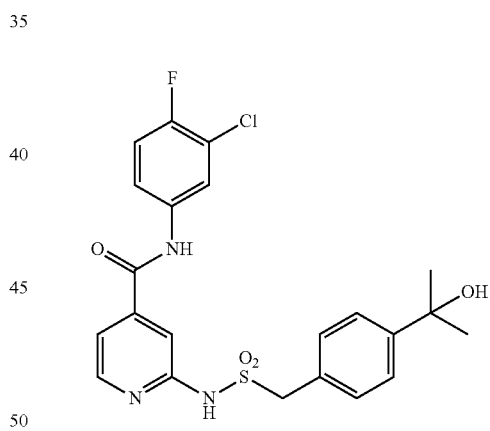

Step 1: 2-(p-Tolyl)propan-2-ol (90% Tech; 3.0 g, 19.9 mmol) was dissolved in CCl$_4$ and N-bromosuccinimide (3.48 g, 19.6 mmol) and benzoylperoxide (100 mg, cat) was added. The reaction mixture was heated to reflux for 4 hrs, cooled and filtered. The filtrate was evaporated and the residue purified on silica gel eluting with 0 to 10% EtOAc in hexanes to afford 2-(4-(bromomethyl)phenyl)propan-2-ol as a colorless oil.

Step 2: (4-(2-hydroxypropan-2-yl)phenyl)methanesulfonamide is prepared in an identical fashion to Step 1 as described for Compound 72.

Step 3: The title compound was prepared in an analogous manner to Compound 2 using (4-(2-hydroxypropan-2-yl) phenyl)methanesulfonamide as starting material. LC-MS: 478 (M+H)$^+$.

Compound 75

4-fluoro-N-(4-fluoro-3-methylphenyl)-3-(1-methyl-1H-pyrazole-3-sulfonamido)benzamide

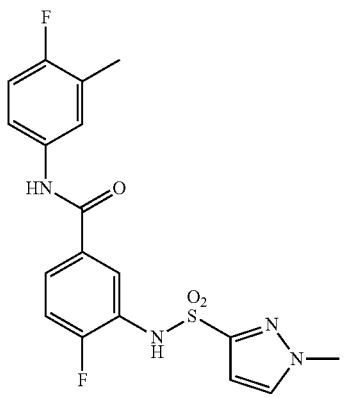 [SMILES: Cc1cc(NC(=O)c2ccc(F)c(NS(=O)(=O)c3ccn(C)n3)c2)ccc1F]

Step 1: To a solution of 3-amino-4-fluorobenzoic acid (2.0 g, 7.7 mmol) in dichloromethane (20 mL) was added 4-fluoro-3-methylaniline (968 mg, 7.7 mmol), diisopropylethylamine (2.68 mL, 15.4 mmol) and HATU (3.22 g, 8.47 mmol). The reaction mixture was maintained at room temperature for 12 hrs after which water was added and diluted with dichloromethane. The resulting suspension was filtered and the solids washed with dichloromethane and dried in vacuo to afford 1.39 g of 3-amino-4-fluoro-N-(4-fluoro-3-methylphenyl)benzamide as a colorless solid. Purification of the filtrate using column chromatography eluting with 0 to 100% EtOAc in hexanes afforded a further 1.0 g of the desired amide.

Step 2: To a solution of 3-Amino-4-fluoro-N-(4-fluoro-3-methylphenyl)benzamide (110 mg, 0.42 mmol) in pyridine (3 mL) cooled to 0° C. was added 1-methyl-1H-pyrazole-3-sulfonyl chloride (90 mg, 0.50 mmol) and catalytic DMAP (10 mg). After stirring at room temperature for 16 hrs, the solution was diluted with EtOAc and water, the organic phase separated, washed with brine, dried (MgSO$_4$), filtered and evaporated in vacuo. Purification of the residue using preparative HPLC afforded the title compound.

Compound 76

N-(3-chloro-4-fluorophenyl)-3-(2-methoxyethylsulfonamido)benzamide

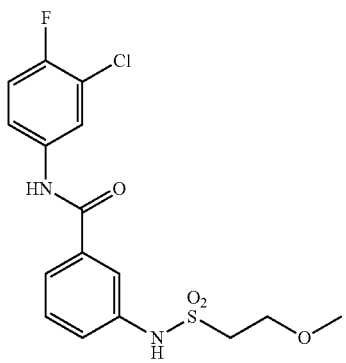 [SMILES: COCCS(=O)(=O)Nc1cccc(C(=O)Nc2ccc(F)c(Cl)c2)c1]

Prepared in an identical manner to Compound 75, step 2 using Intermediate I as starting material and 2-methoxyethanesulfonyl chloride.

Compound 77

N-(3-chloro-4-fluorophenyl)-3-(thiophene-2-sulfonamido)benzamide

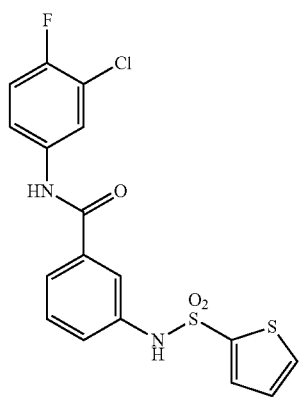 [SMILES: O=C(Nc1ccc(F)c(Cl)c1)c1cccc(NS(=O)(=O)c2cccs2)c1]

Prepared in an identical manner to Compound 75, step 2 using Intermediate I as starting material and thiophene-2-sulfonyl chloride.

Compound 78

N-(3-chloro-4-fluorophenyl)-3-(1H-pyrazole-4-sulfonamido)benzamide

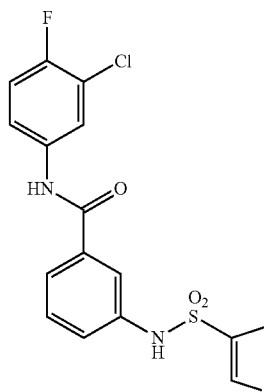

Prepared in an identical manner to Compound 75, step 2 using Intermediate I as starting material and 1H-pyrazole-4-sulfonyl chloride.

Compound 79

N-(3-chloro-4-fluorophenyl)-3-(3,5-dimethyl-1H-pyrazole-4-sulfonamido)benzamide

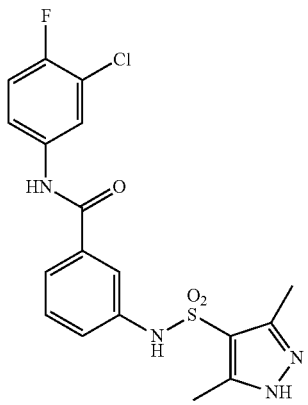 [SMILES: Cc1n[nH]c(C)c1S(=O)(=O)Nc1cccc(C(=O)Nc2ccc(F)c(Cl)c2)c1]

Prepared in an identical manner to Compound 75, step 2 using Intermediate I as starting material and 3,5-dimethyl-1H-pyrazole-4-sulfonyl chloride.

Compound 80

(±)-N-(3-chloro-4-fluorophenyl)-3-(tetrahydrofuran-3-sulfonamido)benzamide

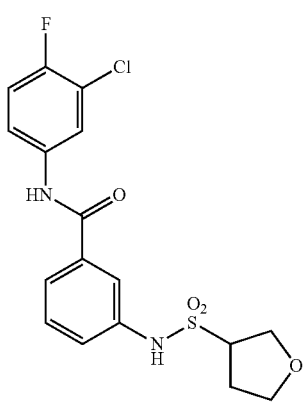 [SMILES: O=C(Nc1ccc(F)c(Cl)c1)c1cccc(NS(=O)(=O)C2CCOC2)c1]

Prepared in an identical manner to Compound 75, step 2 using Intermediate I as starting material and tetrahydrofuran-3-sulfonyl chloride.

Compound 81

(±)-N-(3-chloro-4-fluorophenyl)-3-((tetrahydrofuran-2-yl)methylsulfonamido)benzamide

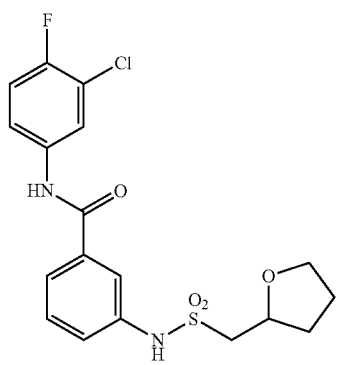 [SMILES: O=C(Nc1ccc(F)c(Cl)c1)c1cccc(NS(=O)(=O)CC2CCCO2)c1]

Prepared in an identical manner to Compound 75, step 2 using Intermediate I as starting material and (tetrahydrofuran-2-yl)methanesulfonyl chloride.

Compound 82

(±)-N-(3-chloro-4-fluorophenyl)-3-(2-methoxy-1-methylethylsulfonamido)benzamide

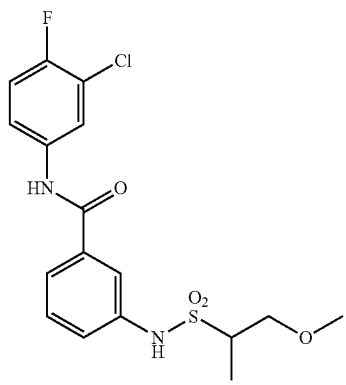 [SMILES: COCC(C)S(=O)(=O)Nc1cccc(C(=O)Nc2ccc(F)c(Cl)c2)c1]

Prepared in an identical manner to Compound 75, step 2 using Intermediate I as starting material and 1-methoxypropane-2-sulfonyl chloride.

Compound 83

(±)-N-(3-chloro-4-fluorophenyl)-3-(2-methyltetrahydrofuran-3-sulfonamido)benzamide

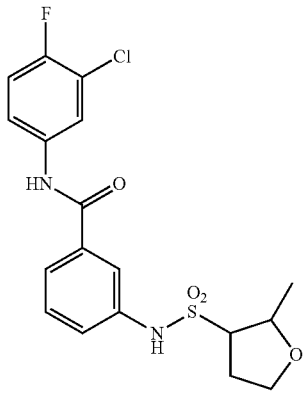 [SMILES: CC1OCCC1S(=O)(=O)Nc1cccc(C(=O)Nc2ccc(F)c(Cl)c2)c1]

Prepared in an identical manner to Compound 75, step 2 using Intermediate I as starting material and 2-methyltetrahydrofuran-3-sulfonyl chloride.

Compound 84

(±)-N-(3-chloro-4-fluorophenyl)-3-(4-hydroxy-1,1-dioxidotetrahydrothiophene-3-sulfonamido)benzamide

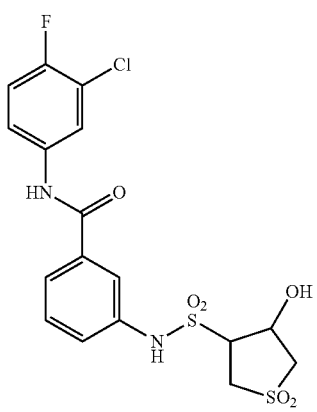 [SMILES: O=C(Nc1ccc(F)c(Cl)c1)c1cccc(NS(=O)(=O)C2CS(=O)(=O)CC2O)c1]

Prepared in an identical manner to Compound 75, step 2 using Intermediate I as starting material and 4-hydroxytetrahydrothiophene-3-sulfonyl chloride 1,1-dioxide.

Compound 85

3-(4-(benzyloxy)piperidine-1-sulfonamido)-N-(3-chloro-4-fluorophenyl)benzamide

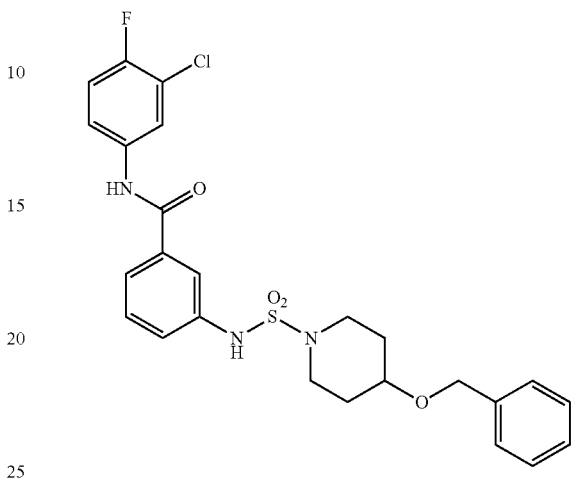

Step 1: Preparation of 4-(benzyloxy)piperidine-1-sulfonyl chloride; To an ice cooled solution of 4-(benzyloxy)piperidine hydrochloride (0.5 g, 2.2 mmol) in DCM (10 mL) was added triethylamine (920 μL, 6.6 mmol) followed by dropwsie addition of chlorosulfonic acid (146 μL, 2.2 mmol). The resulting solution was stirred at room temperature for 16 hrs and concentrated, the residue washed with $Et_2O$ and dried in vacuo. The crude residue was suspended in benzene (7 mL), $PCl_5$ (458 mg, 2.2 mmol) added and heated to reflux for 2 hrs. After cooling, the mixture was diluted in EtOAc and washed with 5% citric acid solution, saturated bicarbonate, and brine. After drying with $MgSO_4$, the crude material was concentrated to afford 4-(benzyloxy)piperidine-1-sulfonyl chloride as an oil used without further purification.

Step 2: Prepared in an identical manner to Compound 75, step 2 using Intermediate I as starting material and 4-(benzyloxy)piperidine-1-sulfonyl chloride.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

Materials:

Unless otherwise noted, all starting materials and resins were obtained from commercial suppliers and used without purification.

Example: Inhibition of HBV Replication Dot-blot Assay

Compounds active in the HBV assembly assay are tested for their activity and toxicity in cellular assay. In the first anti-viral assay, the ability of compounds to inhibit HBV replication in an HBV-producing hepatoma cell line using the dot-blot method is evaluated.

Briefly, confluent monolayers of HepG2-2.2.15 cells are incubated with complete medium containing various concentrations of a test compound. Three days later, the culture medium is replaced with fresh medium containing the appropriately diluted test compound. Six days following the initial administration of the test compound, the cell culture supernatant is collected, and cell lysis is performed. The samples are applied onto Nylos membranes and DNA is immobilized to the membrane by UV cross-linking. After pre-hybridization, the HBV probe is added and the hybridization is performed overnight. The membranes are exposed to the KODAK films; antiviral activity is calculated from the reduction in HBV DNA levels ($EC_{50}$). The $EC_{50}$ for antiviral activity is calculated from the dose response curves of active compounds. Assay performance over time is monitored by the use of the standard positive control compounds ETV, BAY 41-4109, and HAP-1.

Compound cytotoxicity ($TC_{50}$) is measured in this same HepG2-2.2.15 cell line using a CELLTITER BLUE-based cytotoxicity assay employed as recommended by manufacturer (Promega). To confirm and expand these results, a second antiviral assay is carried out on active compounds using the stable HBV cell line HepG2.2.15 and measuring anti-HBV potency by real-time PCR and cytotoxicity by CELLTITER BLUE. In this assay, 24 hours after cell seeding, HepG2-2.2.15 cells are incubated with complete medium containing various concentrations of a test compound with BAY 41-4109 and HAP-1 used as positive controls. After three days, the culture medium is replaced with fresh medium containing the appropriately diluted test compound. The cell culture is collected six days following the initial administration of the test compound, followed by HBV DNA extraction using QIAamp 96 DNA Blood Kit (Qiagen). The extracted HBV DNA is diluted and analyzed by Real-Time PCR. A standard curve is generated by plotting Ct value vs the amount of HBV plasmid standard. Cytotoxicity is determined similarly to the above described method by applying a dye uptake method (CELLTITER BLUE kit, Promega).

Selected compounds are tested for their activity and toxicity in cellular assay. In the first anti-viral assay, the ability of compounds to inhibit HBV replication in an HBV-producing hepatoma cell line using the dot-blot method is evaluated.

Confluent monolayers of HepG2-2.2.15 cells are incubated with complete medium containing various concentrations of a test compound. Three days later, the culture medium is replaced with fresh medium containing the appropriately diluted test compound. Six days following the initial administration of the test compound, the cell culture supernatant is collected, and cell lysis was performed. The samples are applied onto Nylos membranes and DNA is immobilized to the membrane by UV cross-linking. After pre-hybridization, the HBV probe is added and the hybridization is performed overnight. The membranes are exposed to the KODAK films; antiviral activity is calculated from the reduction in HBV DNA levels ($EC_{50}$). The $EC_{50}$ for antiviral activity is calculated from the dose response curves of active compounds. Assay performance over time is monitored by the use of the standard positive control compounds ETV, BAY 41-4109, and HAP-1. Results for selected compounds of the invention are illustrated in Table 2.

Cytotoxicity ($CC_{50}$) is measured in this same HepG2-2.2.15 cell line using a CELLTITER BLUE-based cytotoxicity assay employed as recommended by the manufacturer (Promega).

Example: HBV Replication Inhibition Assay

HBV replication inhibition by the compounds of this invention could be determined in cells infected or transfected with HBV, or cells with stably integrated HBV, such as HepG2.2.15 cells (Sells et al. 1987). In this example, HepG2.2.15 cells are maintained in cell culture medium containing 10% fetal bovine serum (FBS), Geneticin, L-glutamine, penicillin and streptomycin. HepG2.2.15 cells could be seeded in 96-well plates at a density of 40,000 cells/well and be treated with serially diluted compounds at a final DMSO concentration of 0.5% either alone or in combination by adding drugs in a checker box format. Cells are incubated with compounds for three days, after which medium is removed and fresh medium containing compounds is added to cells and incubated for another three days. At day 6, supernatant is removed and treated with DNase at 37° C. for 60 minutes, followed by enzyme inactivation at 75° C. for 15 minutes. Encapsidated HBV DNA is released from the virions and covalently linked HBV polymerase by incubating in lysis buffer (Affymetrix QS0010) containing 2.5 µg proteinase K at 50° C. for 40 minutes. HBV DNA is denatured by addition of 0.2 M NaOH and detected using a branched DNA (bDNA) QuantiGene assay kit according to manufacturer recommendation (Affymetrix).

HBV DNA levels could also be quantified using qPCR, based on amplification of encapsidated HBV DNA extraction with QUICKEXTRACT Solution (Epicentre Biotechnologies) and amplification of HBV DNA using HBV specific PCR probes that can hybridize to HBV DNA and a fluorescently labeled probe for quantitation. In addition, cell viability of HepG2.2.15 cells incubated with test compounds alone or in combination is determined by using CELLTITER-GLO reagent according to the manufacturer protocol (Promega). The mean background signal from wells containing only culture medium is subtracted from all other samples, and percent inhibition at each compound concentration is calculated by normalizing to signals from HepG2.2.15 cells treated with 0.5% DMSO using equation E1.

% inhibition=($DMSO$ave−$Xi$)/$DMSO$ave×100%   E1:

wherein DMSOave is the mean signal calculated from the wells that are treated with DMSO control (0% inhibition control) and Xi is the signal measured from the individual wells. EC50 values, effective concentrations that achieved 50% inhibitory effect, are determined by non-linear fitting using Graphpad Prism software (San Diego, Calif.) and equation E2.

$$Y = Y\min + (Y\max - Y\min)/(1 + 10(\text{Log } EC50 - X) \times \text{Hill-Slope})  \quad \text{E2:}$$

wherein Y represents percent inhibition values and X represents the logarithm of compound concentrations.

Selected compounds of the invention were assayed in the HBV replication assay, as described above and a representative group of these active compounds is shown in Table 3.

TABLE 2

| "Activity" represents activity in Dot-Blot assay ('+' indicates $EC_{50}$ <10 µM) | |
|---|---|
| Compound No. | Activity |
| 1 | + |
| 2 | + |
| 3 | + |
| 5 | + |
| 6 | + |
| 8 | + |
| 9 | + |
| 11 | + |
| 12 | + |
| 15 | + |
| 16 | + |
| 17 | + |
| 19 | + |
| 21 | + |
| 22 | + |
| 23 | + |
| 27 | + |
| 28 | + |
| 30 | + |
| 32 | + |
| 35 | + |
| 36 | + |
| 39 | + |
| 41 | + |
| 42 | + |
| 43 | + |
| 51 | + |
| 57 | + |
| 58 | + |
| 59 | + |
| 64 | + |
| 75 | + |
| 76 | + |
| 77 | + |
| 78 | + |
| 79 | + |
| 80 | + |
| 81 | + |
| 82 | + |
| 83 | + |
| 84 | + |
| 85 | + |

TABLE 3

| HBV Replication Inhibition | |
|---|---|
| Compound No | Extra HBV DNA (µM) |
| 1 | 3 |
| 2 | 0.1 |
| 3 | 2.1 |

TABLE 3-continued

| HBV Replication Inhibition | |
|---|---|
| Compound No | Extra HBV DNA (µM) |
| 4 | 1 |
| 58 | 0.3 |
| 59 | 0.7 |
| 64 | 2.7 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of Formula II:

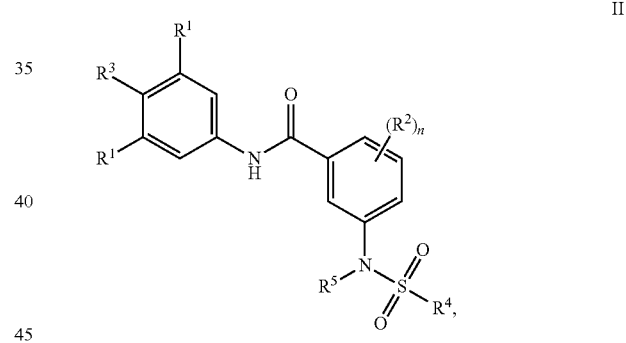

or a pharmaceutically acceptable salt thereof;

wherein one $R^1$ is H and one $R^1$ is selected from halo and $C_{1-6}$-alkyl;

$R^2$ is halo;

$R^3$ is halo;

$R^4$ is $C_{1-6}$-heteroalkyl or heteroaryl, each of which may be independently substituted with one or two of $C_{1-6}$-alkyl;

$R^5$ is H; and n is 0 or 1.

2. The compound of claim 1, or a pharmaceutically acceptable salt thereof, wherein the compound is selected from the group consisting of:

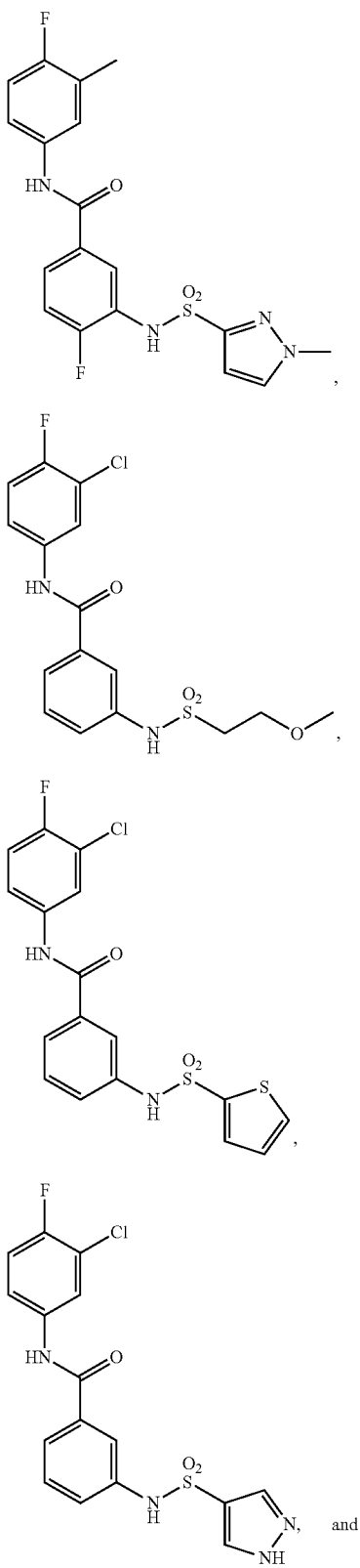

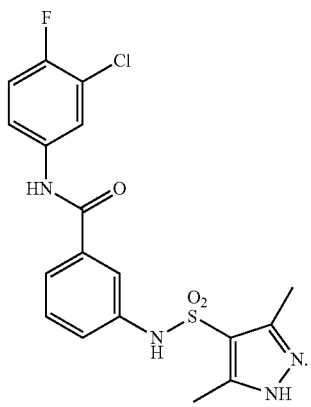

3. A composition comprising a compound according to claim 1, or a pharmaceutically acceptable salt thereof, further comprising at least one pharmaceutically acceptable carrier.

4. A method of treating an HBV infection in an individual having an HBV infection, comprising administering to the individual a therapeutically effective amount of a compound according to claim 1.

5. The method of claim 4, further comprising administering to the individual at least one additional therapeutic agent selected from the group consisting of an HBV vaccine, HBV polymerase inhibitor, interferon, pegylated interferon, viral entry inhibitor, viral maturation inhibitor, BAY 41-4109, reverse transcriptase inhibitor, a TLR-agonist, AT-61 ((E)-N-(1-chloro-3-oxo-1-phenyl-3-(piperidin-1-yl)prop-1-en-2-yl)benzamide), and AT-130 ((E)-N-(1-bromo-1-(2-methoxyphenyl)-3-oxo-3-(piperidin-1-yl)prop-1-en-2-yl)-4-nitrobenzamide), and a combination thereof.

6. The method of claim 5, wherein the pegylated interferon is pegylated interferon alpha (IFN-α), pegylated interferon lambda (IFN-λ), or pegylated interferon gamma (IFN-γ).

7. The method of claim 5, wherein the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

8. The method of claim 5, wherein the TLR-agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}1methyl)phenyl]acetate).

* * * * *